US008329950B2

(12) United States Patent
Caron et al.

(10) Patent No.: US 8,329,950 B2
(45) Date of Patent: Dec. 11, 2012

(54) PROCESS FOR PREPARATION OF TRANS 4-(3,4-DICHLOROPHENYL)-1,2,3,4-TETRAHYDRO-1NAPTHALENAMINE

(75) Inventors: Judy Caron, Westwood, MA (US); Thomas Wessel, Lenox, MA (US); Karim Lalji, West Vancouver, CA (US); Mark Varney, Laguna Niguel, CA (US); Roger P. Bakale, Malvern, PA (US); Surendra P. Singh, Shrewsbury, MA (US); H. Scott Wilkinson, Westborough, MA (US); Xiping Su, Woodbridge, CT (US); Zhengxu Han, Shrewsbury, MA (US); Stefan G. Koenig, Shrewsbury, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

(21) Appl. No.: 13/358,155

(22) Filed: Jan. 25, 2012

(65) Prior Publication Data
US 2012/0123164 A1     May 17, 2012

Related U.S. Application Data

(62) Division of application No. 11/994,644, filed as application No. PCT/US2006/026361 on Jul. 6, 2006, now abandoned.

(60) Provisional application No. 60/697,013, filed on Jul. 6, 2005.

(51) Int. Cl.
C07C 209/62    (2006.01)
(52) U.S. Cl. .......................... 564/308; 564/415
(58) Field of Classification Search .................. None
See application file for complete search history.

(56) References Cited

U.S. PATENT DOCUMENTS

| 4,045,488 A | 8/1977 | Sarge |
| 4,540,690 A | 9/1985 | Szmuszkovicz |
| 4,556,676 A | 12/1985 | Welch, Jr. et al. |
| 4,587,258 A | 5/1986 | Gold et al. |
| 4,608,382 A | 8/1986 | Ferrini et al. |
| 4,634,703 A | 1/1987 | Kurtz et al. |
| 4,687,772 A | 8/1987 | Alderdice |
| 4,738,709 A | 4/1988 | Nielsen |
| 4,751,231 A | 6/1988 | Halczenko et al. |
| 4,981,870 A | 1/1991 | Koe |
| 5,061,728 A | 10/1991 | Koe |
| 5,373,018 A | 12/1994 | Cugola et al. |
| 5,374,649 A | 12/1994 | Cugola et al. |
| 5,468,749 A | 11/1995 | Gawin et al. |
| 5,523,278 A | 6/1996 | Wepplo |
| 5,550,255 A | 8/1996 | Urbach et al. |
| 5,578,627 A | 11/1996 | Takeda et al. |
| 5,620,997 A | 4/1997 | Bolton et al. |
| 5,668,162 A | 9/1997 | Domagala et al. |
| 5,686,461 A | 11/1997 | Cugola et al. |
| 5,786,357 A | 7/1998 | Young |
| 5,788,986 A | 8/1998 | Dodman |
| 5,858,407 A | 1/1999 | Ayer et al. |
| 5,859,042 A | 1/1999 | Lee et al. |
| 5,962,496 A | 10/1999 | Cugola et al. |
| 5,965,591 A | 10/1999 | Kojima et al. |
| 6,096,771 A | 8/2000 | Kojima et al. |
| 6,100,289 A | 8/2000 | Cugola et al. |
| 6,136,824 A | 10/2000 | MacLeod et al. |
| 6,245,782 B1 | 6/2001 | Serebruany et al. |
| 6,319,926 B1 | 11/2001 | Cotrel et al. |
| 6,331,636 B1 | 12/2001 | Romero et al. |
| 6,372,919 B1 | 4/2002 | Lippa et al. |
| 6,399,601 B1 | 6/2002 | Du Bois |
| 6,436,936 B1 | 8/2002 | Young et al. |
| 6,444,673 B1 | 9/2002 | Cotrel et al. |
| 6,451,788 B1 | 9/2002 | Horrobin et al. |
| 6,479,527 B1 | 11/2002 | Barker et al. |
| 6,506,940 B1 | 1/2003 | Jadav et al. |
| 6,576,653 B2 | 6/2003 | Du Bois |
| 6,589,949 B1 | 7/2003 | Moriwaki et al. |
| 6,603,000 B2 | 8/2003 | Yee et al. |
| 6,828,460 B2 | 12/2004 | Browning et al. |
| 6,864,257 B2 | 3/2005 | Cotrel et al. |
| 6,995,144 B2 | 2/2006 | Ozaki et al. |
| 7,087,785 B2 | 8/2006 | Jerussi et al. |
| 7,105,699 B2 | 9/2006 | Jerussi et al. |
| 7,125,874 B2 | 10/2006 | Cotrel et al. |

(Continued)

FOREIGN PATENT DOCUMENTS

BE    616646    5/1962

(Continued)

OTHER PUBLICATIONS

Welch et al. "Nontricyclic Antidepressant Agents Derived From Cis- and Trans-1-Amino-4-Aryltetralins", J. of Medicinal Chemistry, Amer. Chem. Society, vol. 27, No. 11, 1984, pp. 1508-1515.
The ISR and Written Opinion of the ISA from corresponding PCT Application No. PCT/US2010/058831, dated Aug. 30, 2011.
The ISR and Written Opinion of the ISA from corresponding PCT Application No. PCT/US2010/034473, dated Feb. 8, 2010.
Andersen, Peter H., "Biochemical and Pharmacological Characterization of [$^3$H]GBR 12935 Binding In Vitro to Rat Striatal Membranes: Labeling of the Dopamine Uptake Complex", J. Neurochemistry, 48, 1887-1896, (1987).

(Continued)

Primary Examiner — Brian J Davis
(74) Attorney, Agent, or Firm — Heslin Rothenberg Farley & Mesiti P.C.

(57) ABSTRACT

One aspect of the present invention relates to pharmaceutical compositions containing two or more active agents that when taken together can be used to treat, e.g., menopause, mood disorders, anxiety disorders, or cognitive disorders. The first component of the pharmaceutical composition is a sedative eszopiclone. The second component of the pharmaceutical composition is trans 4-(3,4-dichlorophenyl)-1,2,3,4-tetrahydro-N-methyl-1-napthalenamine or trans 4-(3,4-dichlorophenyl)-1,2,3,4-tetrahydro-1-napthalenamine. The present invention also relates to a method of treating menopause, perimenopause, mood disorders, anxiety disorders, and cognitive disorders.

13 Claims, No Drawings

U.S. PATENT DOCUMENTS

| | | |
|---|---|---|
| 7,166,725 B2 | 1/2007 | Fang et al. |
| 7,226,938 B2 | 6/2007 | CM et al. |
| 7,381,724 B2 | 6/2008 | Cotrel et al. |
| 7,423,179 B2 | 9/2008 | Jerussi et al. |
| 7,465,729 B2 | 12/2008 | Wessel et al. |
| 7,488,747 B2 | 2/2009 | Fang et al. |
| 7,579,370 B2 | 8/2009 | Heffernan et al. |
| 7,589,237 B2 | 9/2009 | Jerussi et al. |
| 7,615,572 B2 | 11/2009 | Fang et al. |
| 7,776,858 B2 | 8/2010 | Wessel et al. |
| 7,790,772 B2 | 9/2010 | Jerussi et al. |
| 8,071,599 B2 | 12/2011 | Wessel et al. |
| 8,097,625 B2 | 1/2012 | Lalji et al. |
| 8,097,760 B2 | 1/2012 | Zhao et al. |
| 8,134,029 B2 | 3/2012 | Jerussi et al. |
| 2002/0010198 A1 | 1/2002 | Jerussi et al. |
| 2002/0085976 A1 | 7/2002 | Elomari |
| 2002/0123490 A1 | 9/2002 | Howard, Jr. |
| 2002/0183369 A1 | 12/2002 | Du Bois |
| 2003/0078262 A1 | 4/2003 | Taylor |
| 2003/0087803 A1 | 5/2003 | Yatvin et al. |
| 2003/0171440 A1 | 9/2003 | Senanayake et al. |
| 2003/0195361 A1 | 10/2003 | Du Bois |
| 2003/0215523 A1 | 11/2003 | Ozawa et al. |
| 2004/0048878 A1 | 3/2004 | Cai et al. |
| 2004/0077864 A1 | 4/2004 | Kim et al. |
| 2004/0087661 A1 | 5/2004 | Jerussi et al. |
| 2004/0092605 A1 | 5/2004 | Jerussi et al. |
| 2004/0106681 A1 | 6/2004 | Rao et al. |
| 2004/0220229 A1 | 11/2004 | Bussolotti et al. |
| 2005/0020645 A1 | 1/2005 | Ohta et al. |
| 2005/0089935 A1 | 4/2005 | Cai et al. |
| 2005/0143434 A1 | 6/2005 | Fang et al. |
| 2005/0143443 A1 | 6/2005 | Fang et al. |
| 2005/0176680 A1 | 8/2005 | Lalji et al. |
| 2005/0222157 A1 | 10/2005 | Wessel et al. |
| 2005/0267176 A1 | 12/2005 | Barberich |
| 2006/0019944 A1 | 1/2006 | Wu et al. |
| 2006/0128993 A1 | 6/2006 | Jerussi et al. |
| 2006/0216799 A1 | 9/2006 | Jerussi et al. |
| 2006/0229286 A1 | 10/2006 | Kakigami et al. |
| 2006/0235002 A1 | 10/2006 | Nagai et al. |
| 2007/0100135 A1 | 5/2007 | Riggs et al. |
| 2007/0142452 A1 | 6/2007 | Banner et al. |
| 2007/0197588 A1 | 8/2007 | Shao et al. |
| 2007/0203111 A1 | 8/2007 | Shao et al. |
| 2007/0282007 A1 | 12/2007 | Tarantino et al. |
| 2007/0299055 A1 | 12/2007 | Lalji et al. |
| 2008/0004327 A1 | 1/2008 | Heffernan et al. |
| 2008/0004328 A1 | 1/2008 | Dorsey et al. |
| 2008/0058395 A1 | 3/2008 | Heffernan et al. |
| 2008/0175903 A1 | 7/2008 | Hopkins et al. |
| 2008/0262071 A1 | 10/2008 | Dinan et al. |
| 2008/0280993 A1 | 11/2008 | Jerussi et al. |
| 2009/0005456 A1 | 1/2009 | Shao et al. |
| 2009/0099248 A1 | 4/2009 | Heffernan et al. |
| 2009/0111817 A1 | 4/2009 | Caron et al. |
| 2009/0111818 A1 | 4/2009 | Caron et al. |
| 2009/0149549 A1 | 6/2009 | Zhao et al. |
| 2010/0004251 A1 | 1/2010 | Barberich |
| 2010/0016397 A1 | 1/2010 | Fang et al. |
| 2010/0022612 A1 | 1/2010 | Dorsey et al. |
| 2010/0029737 A1 | 2/2010 | Heffernan et al. |
| 2010/0029741 A1 | 2/2010 | Dorsey et al. |
| 2010/0120740 A1 | 5/2010 | Heffernan et al. |
| 2010/0280038 A1 | 11/2010 | Wessel et al. |
| 2010/0292340 A1 | 11/2010 | Jerussi et al. |
| 2012/0035182 A1 | 2/2012 | Wessel et al. |

FOREIGN PATENT DOCUMENTS

| | | |
|---|---|---|
| CA | 2066593 | 2/1992 |
| CA | 2410077 | 11/2001 |
| CA | 2474451 | 8/2003 |
| CA | 2498152 | 3/2004 |
| CA | 2498175 | 3/2004 |
| CA | 2565852 | 11/2005 |
| CA | 2566094 | 12/2005 |
| CN | 1106386 | 8/1995 |
| CN | 1709871 | 12/2005 |
| CN | 1962656 | 5/2007 |
| DE | 1124485 | 3/1962 |
| DE | 3431541 | 3/1986 |
| EP | 0028901 A1 | 5/1981 |
| EP | 101786 | 3/1984 |
| EP | 0285008 A21 | 10/1988 |
| EP | 396124 | 11/1990 |
| EP | 0442423 A1 | 8/1991 |
| EP | 0497314 A1 | 8/1992 |
| EP | 1136071 | 9/2001 |
| EP | 1219603 | 7/2002 |
| EP | 1262181 | 12/2002 |
| EP | 1262197 A2 | 12/2002 |
| EP | 1362864 | 11/2003 |
| EP | 1088824 | 1/2004 |
| EP | 1391460 | 2/2004 |
| EP | 1420028 | 5/2004 |
| ES | 2081747 | 3/1996 |
| JP | S54-059269 | 5/1979 |
| JP | 58010518 U | 1/1983 |
| JP | H01-016786 | 1/1989 |
| JP | 1101-172388 | 7/1989 |
| JP | 2003246225 A | 11/1991 |
| JP | H04-077476 | 3/1992 |
| JP | 2002020291 A | 1/2002 |
| JP | 2003335678 A | 11/2003 |
| WO | WO 86/00896 | 2/1986 |
| WO | WO 95/17381 | 6/1995 |
| WO | 9731629 | 9/1997 |
| WO | WO 98/42709 | 10/1998 |
| WO | WO 99/10343 | 3/1999 |
| WO | WO 99/18065 | 4/1999 |
| WO | WO 99/40913 | 8/1999 |
| WO | WO 99/40914 | 8/1999 |
| WO | WO 99/48868 | 9/1999 |
| WO | WO 00/25770 | 5/2000 |
| WO | WO 01/02427 | 1/2001 |
| WO | WO 01/27103 | 4/2001 |
| WO | WO 01/79208 | 10/2001 |
| WO | WO 02/12249 | 2/2002 |
| WO | WO 02/20530 | 3/2002 |
| WO | WO 02/31128 | 4/2002 |
| WO | 03007956 A1 | 1/2003 |
| WO | WO 03/016302 | 2/2003 |
| WO | WO 03/039540 | 5/2003 |
| WO | 03065970 A2 | 8/2003 |
| WO | WO 03/063797 | 8/2003 |
| WO | WO 03/074531 | 9/2003 |
| WO | WO 03/074532 | 9/2003 |
| WO | WO 03/091213 | 11/2003 |
| WO | WO 03/092670 | 11/2003 |
| WO | WO 2004/022537 | 3/2004 |
| WO | WO 2004/024130 | 3/2004 |
| WO | WO 2004/024669 | 3/2004 |
| WO | WO 2004/031193 | 4/2004 |
| WO | WO 2004/031194 | 4/2004 |
| WO | WO 2004/039787 | 5/2004 |
| WO | WO 2004/041780 | 5/2004 |
| WO | WO 2004/089470 | 10/2004 |
| WO | WO 2004/113345 | 12/2004 |
| WO | WO 2005/013981 | 2/2005 |
| WO | WO 2005/018637 | 3/2005 |
| WO | WO 2005/020986 | 3/2005 |
| WO | WO 2005/020987 | 3/2005 |
| WO | WO 2005/046575 | 5/2005 |
| WO | 2005060968 | 7/2005 |
| WO | WO 2005/066135 | 7/2005 |
| WO | WO 2005/066143 | 7/2005 |
| WO | 2005079851 | 9/2005 |
| WO | WO 2005/089753 | 9/2005 |
| WO | WO 2005/097132 | 10/2005 |
| WO | WO 2005/123677 | 12/2005 |
| WO | WO 2006/001958 | 1/2006 |
| WO | WO 2006/004040 | 1/2006 |
| WO | WO 2006/021000 | 2/2006 |
| WO | WO 2006/077412 | 7/2006 |
| WO | 2007005940 | 1/2007 |

| | | |
|---|---|---|
| WO | 2007005961 | 1/2007 |
| WO | 2007005962 | 1/2007 |
| WO | WO 2007/006797 | 1/2007 |
| WO | 2007030589 A2 | 3/2007 |
| WO | WO 2007/039773 | 4/2007 |
| WO | WO 2007/068621 | 6/2007 |
| WO | WO 2007/081542 | 7/2007 |
| WO | WO 2007/081857 | 7/2007 |
| WO | 2007115185 | 10/2007 |
| WO | WO 2007/006003 A2 | 11/2007 |
| WO | 2007143267 | 12/2007 |
| WO | WO 2008/005456 | 1/2008 |
| WO | 2008070000 | 6/2008 |
| WO | WO 2008/089453 | 7/2008 |
| WO | WO2008/151156 | 12/2008 |
| WO | WO 2009/020814 | 2/2009 |
| WO | WO 2010/017418 | 2/2010 |
| WO | 2010132521 A1 | 11/2010 |
| WO | 2011069032 A1 | 6/2011 |

OTHER PUBLICATIONS

Childers et al., "Lecozotan Hydrochloride: Cognition Enhancer, Treatment of Alzheimer's Disease, Competitive 5-HT1A Receptor Antagonist", *Drugs of the Future*, 32(5), 339-407 (2007).

Clague et al., "Action of Agonists and Antagonists at Muscarinic Receptors Present on Ileum and Atria In Vitro", *British J Pharmacology*, 86, 163-170 (1985).

Deninno et al., "The Preparation and Intra- and Intermolecular Addition Reactions of Acyclic N-Acylimines: Application to the Synthesis of (±)-Sertraline", *J. Organic Chemistry*, 66, 6988-6993 (2001).

Dews, Peter B., "The Measurement of the Influence of Drugs on Voluntary Activity in Mice", *British J. Pharmacology*, 8, 46-48 (1953).

Emsley, Robin, "Drugs in Development for the Treatment of Schizophrenia," *Expert Opin. Investig. Drugs*, 18(8), 1103-1118 (2009).

Fuller et al., "Comparison of Desmethylsertraline With Sertraline as a Monoamine Uptake Inhibitor In Vivo", *Prog. Neuro-Psychopharmacol. & Biol. Psychiatry*, 19, 135-149 (1995).

Galli et al., "Sodium-Dependent Norepinephrine-Induced Currents in Noreprinephrine-Transporter-Transfected HEK-293 Cells Blocked by Cocaine and Antidepressants", *J. Exper. Biology*, 198, 2197-2212 (1995).

Giros et al., "Cloning, Pharmacological Characterization, and Chromosome Assignment of the Human Dopamine Transporter", *Molecular Pharmacology*, 42, 383-390 (1992).

Gonzalez-Viejo et al., "A Comparative Study of Fibromyalgia Treatment: Ultrasonography and Physiotherapy Versus Sertraline Treatment", *Annales de readaption et de medecine physique*, 48, 610-615 (2005).

Goodnick et al., "Sertraline in Diabetic Neuropathy: Preliminary Results", *Annals of Clin. Psychiatry*, 9(4), 255257 (1997).

Goodnick, Paul J., "Use of Antidepressants in Treatment of Comorbid Diabetes Mellitus and Depression as Well as in Diabetic Neuropathy", *Annals of Clin. Psychiatry*, 13(1), 31-41 (2001).

Gu et al., "Stable Expression of Biogenic Amine Transporters Reveals Differences in Inhibitor Sensitivity, Kinetics, and Ion Dependence", *J. Biol. Chem.*, 269(10), 7124-7130 (1994).

Hamelin et al., "The Disposition of Fluoxetine But Not Sertraline Is Altered in Poor Metabolizers of Debrisoquin", *Clinical Pharmacology & Therapeutics*, 60(5), 512-521 (1996).

Harrison et al., "Compendium of Organic Synthetic Methods", 258-259 (1971).

Janowsky et al., "Characterization of Sodium-Dependent [$^3$H]GBR-12935 Binding in Brain: A Radioligand for Selective Labelling of the Dopamine Transport Complex", *J. Neurochemistry*, 46, 1272-1276 (1986).

Kim & Chung, "An Experimental Model for Peripheral Neuropathy Produced by Segmental Spinal Nerve Litigation in the Rat", 50, 355-363 (1992).

Koe et al., "Sertraline, /S,4S-N-Methyl-4-(3,4-Dichlorophenyl)-1,2,3,4-Tetrahydro-1-Naphthylamine, A New Uptake Inhibitor with Selectivity for Serotonin", *J. Pharmacology & Experimental Therapeutics*, 226(3), 686700 (1983).

Lifschytz et al., "Sex-dependent Effects of Fluoxetine and Triiodothyronine in the Forced Swim Test in Rats", *Euro. Nueropsychopharmacology*, 16, 115-121 (2006).

Maehr, Hubert, "A Proposed New Convention for Graphic Presentation of Molecular Geometry and Topography", *J. Chem. Educ.*, 62, 114-120 (1985).

Mckelvy, J. F., "AV965, A Selective 5-HT1A Silent Antagonist as a Candidate for Adjunctive Treatment of Cognitive Impairment in Schizophrenia," *International Congress of Schizophrenia Research*, Schizophrenia Bulletin, 31(2), 305 (2005).

Pacholczyk et al., "Expression Cloning of a Cocaine- and Antidepressant-Sensitive Human Noradrenalin Transporter", *Letters to Nature*, 350, 350-354 (1991).

Perovic & Muller, "Pharmacological Profile of Hypericum Extract", *A rzneim.-Forsch/Drug Res.*, 45(11), 11451148 (1995).

Porsolt et al., "Behavioural Despair in Mice: a Primary Screening Test for Antidepressants", *Arch Int. Pharmacdoyn*, 229, 327-336 (1977).

Pristupa et al., "Pharmacological Heterogeneity of the Cloned and Native Human Dopamine Transporter: Disassociation of [$^3$H]WIN 35,428 and [$^3$H]GBR 12,935 Binding", *ASPET*, 45, 125-135 (1994).

Ronfeld et al., "Pharmacokinetics of Sertraline and Its N-Demethyl Metabolite in Elderly and Young Male and Female Volunteers", *Clinical Pharmacokinet.*, 32, 22-30 (1997).

Sanchez & Hyttel, "Comparison of the Effects of Antidepressants and Their Metabolites on Reuptake of Biogenic Amines and on Receptor Binding", *Cellular and Molecular Neurobiology*, 19(4), 467-489 (1999).

Semenchuk et al., "Double-Blind, Randomized Trial of Bupropion SR for the Treatment of Neuropathic Pain", *Neurology*, 57, 1583-1588 (2001).

Serebruany et al., "Platelet Inhibition by Sertraline and N-Desmethylsertraline: A Possible Missing Link Between Depression, Coronary Events, and Mortality Benefits of Selective Serotonin Reuptake Inhibitors", *Pharmacological Research*, 43(5), 453-461 (2001).

Tang et al., "An Ortho-Substituted BIPHEP Ligand and Its Applications in Rh-Catalyzed Hydrogenation of Cyclic Enamides", *Organic Letters*, 4(10), 1695-1698 (2002).

Tatsumi et al., "Pharmacological Profile of Antidepressants and Related Compounds at Human Monoamine Transporters", *Euro. J. Pharma.*, 340, 249-258 (1997).

Vazquez-Palacios et al., "Antidepressant-Like Effects of the Acute and Chronic Administration of Nicotine in the Rat Forced Swimming Test and its Interaction with Flouxetine", *Pharmacology, Biochemistry and Behavior*, 78, 165-169 (2004).

Wheeler-Aceto et al., "Standardization of the Rat Paw Formalin Test for the Evaluation of Analgesics", *Psychopharmacology*, 104, 35-44 (1991).

Witchel et al., "Inhibitory Actions of the Selective Serotonin Reuptake Inhibitor Citalopram on HERG and Ventricular L-type Calcium Currents", *FEBS Letters*, 512, 59-66 (2002).

Wong et al., "Norfluoxetine Enantiomers as Inhibitors of Serotonin Uptake in Rat Brain", *Neuropsychopharmacology*, 8(4), 337-344 (1993).

Yaksh et al., "An Automated Flinch Detecting System for Use in the Formalin Nociceptive Bioassay", *J. Appl. Physiol.*, 90, 2386-2402 (2001).

Communication pursuant to Article 96(2) EPC, dated Nov. 30, 2007 from the European Patent Office for European Application No. 03754641.3—2103, cover page and pp. 1-5.

Notice of Allowance for U.S. Appl. No. 11/416,586 dated Apr. 29, 2008.

ISR & WO for International Patent Application No. PCT/US07/65585 dated Oct. 3, 2008.

ISR & WO for International Patent Application No. PCT/US03/29110 dated Mar. 2, 2004.

Search Report and Written Opinion for International Patent Application No. PCT/US06/26361dated May 8, 2008.

European Search Report for corresponding European Patent Application No. EP 06 78 6496 dated Sep. 11, 2009.

Abarbri et al., "Les beta-cetonitriles groupes protecteurs de la fonction amine. Preparation d'aminoalcools", Hely. Chim. Acta 1995, 78(1), 109-121.

Aboul-Enein etal., "Synthesis and Antiemetic Profile of ND-[(diethylamino)methyl]cyclohexyl]amides", Sci. Pharm. 1990, 58(3), 273-280.

Alvaro et al., "Preparation and photolysis of diaryl esters of acetylenedicarboxylic acid", Tetrahedron 1992, 48(16), 3437-3444.

Ando et al., "3-(Arylacetylamino)-N-methylbenzamides: A Novel Class of Selective AntiHelicobacter pylori Agents", J. Med. Chem. 2001, 44(25), 4468-4474.

Arya et al., "Synthesis of New Heterocycles: Part XV. Synthesis of Novel Cyclic and Acyclic Sulfamides", Indian J. Chem., Sec. B, 1976, 14B(10), 766-769.

Ashton et al., "Nonpeptide angiotensin II antagonists derived from 1H-pyrazole-5-carboxylates and 4-aryl-1H-imidazole-5-carboxylates", J. Med. Chem. 1993, 36(23), 3595-3605.

Associated Press, "FDA mulls drug to slow late-stage Alzheimer's", CNN.com, Sep. 24, 2003, URL: <http://www.cnn.com/2003/HEALTH/conditions/09/24/alzheimers.drug.ap/in-dex.html>.

Aubert et al., "New cyclopenta[b]-pyrroles and -pyridines by reaction of 2-azido- and 2-phosphoranylideneaminocyclopent- 1-ene-1-carbaldehydes with aliphatic esters", J. Chem. Soc. Perkin Trans. 1 1989(8), 1369-1373.

Azema et al., "Efficient approach to acyloxymethyl esters of nalidixic acid and in vitro evaluation as intra-ocular prodrugs", Bioorg. Med. Chem. 2006, 14(8), 2569-2580.

Baba et al., "Structure-Based Design of a Highly Selective Catalytic Site-Directed Inhibitor of Ser/Thr Protein Phosphatase 2B (Calcineurin)", J. Am. Chem. Soc. 2003, 125(32), 9740-9749.

Babu et al., "Simple and facile oxidation of aldehydes to carboxylic acids", Org. Prep. Proced. Int. 1994, 26(1), 123-125.

Bagal et al.,"Radicals from Aldehydes: A Convergent Access to Dienes and .delta.-Lactones", Synlett 2006(10), 1485-1490.

Balsamini et al., "(E)-3-(2-(N-phenylcarbamoyl)vinyl)pyrrole-2-carboxylic acid derivatives. A novel class of glycine site antagonists", J. Med. Chem. 1998, 41(6), 808-820.

Balsamini et al., "An improved route to cycloalka[b]pyrrole 2-carboxylates", Org. Prep. Proced. Int. 1997, 29(4), 471-473.

Bambury et al., "Trifluoromethylfurans II", J. Heterocycl. Chem. 1970, 7(2), 269-273.

Banekovich et al., "Synthesis and biological activities of novel dexibuprofen tetraacetylriboflavin conjugates", Bioorg. Med. Chem. Lett. 2007, 17(3), 683-687.

Banfi et al., "Synthesis of New Imidazole Derivatives as Potential Inhibitors of Thromboxane Synthetase", J. Heterocycl. Chem. 1990, 27, 215-219.

Bardakos et al., "Enhydrazine, 10. Einige aliphatische Enhydrazone", Chem. Ber. 1975, 108(7), 2 161-2 170.

Bartlett et al., "Evaluation of alternative approaches for the synthesis of macrocyclic bisindolylmaleimides", Org. Biomol. Chem. 2004, 2(19), 2874-2883.

Basf Corp., "Borane-tetrahydrofuran Complex (BTHF)" Product Bulletin, 2002, pp. 1-14.

Baumes et al., "No. 227.—Recherches sur les enehydrazines. VI.—Condensation de methylhydrazones de cetones sur les esters acetyleniques: synthese de carbomethoxypyrroles", Bull. Soc. Chim. Fr. 1974(5-6), 1147-1150.

Beaumont et al., "Design of Ester Prodrugs to Enhance Oral Absorption of Poorly Permeable Compounds: Challenges to the Discovery Scientist", Curr. Drug Metab. 2003, 4(6), 461-485.

Bedford et al., "Quaternary salts of 2-Rhydroxyimino)methylilmidazole. 2. Preparation and in vitro and in vivo evaluaton of 1-(alkoxymethyl)-2-[(hydroxyimino)methyl]-3-methylimidazolium halides for reactivation of organophosphorus-inhibited acetylcholinesterases", J. Med. Chem. 1989, 32(2), 493-503.

Benson et al., "Aliphatic .beta.-Chlorovinyl Aldoximes", J. Org. Chem. 1965, 30(4), 1126-1129.

Bergauer et al., "Practical ex-chiral-pool methodology for the synthesis of dopaminergic tetrahydroindoles", Tetrahedron 2004, 60(5), 1197-1204.

Bialer et al., "Pharmacokinetic analysis and antiepileptic activity of tetra-methylcyclopropane analogues of valpromide", Pharm. Res. 1996, 13(2), 284-289.

Biggadike et al., "Selective plasma hydrolysis of glucocorticoid gamma-lactones and cyclic carbonates by the enzyme parazonase: an ideal plasma inactivation mechanism." J. Med. Chem. 2000, 43(1), 19-21.

Birkofer et al., "The Use of Silylation in Organic Syntheses", Angew. Chem. Int Ed. 1965, 4(5), 417-429.

Black, D., "Product Class 13: 1H-Pyrroles" in "Science of Synthesis: Houben-Weyl Methods of Molecular Transformations", vol. 9; Maas, G., ed.; Thieme Medical Publishers: Stuttgart, 2001; pp. 441-552.

Blanchfield et al., "The stability of lipidic analogues of GnRH in plasma and kidney preparations: the stereoselective release of the parent peptide", Bioorg. Med. Chem. Lett. 2005, 15(6), 1609-1612.

Boar et al., "Simple synthesis of enamides from ketoximes," Journal of the Chemical Society, Perkin Transactions I: Organic and Bio-Organic Chemistry 1975, (13), 1237-1241.

Bobbitt et al., "Organic Nitrosonium Salts. II. Stability Studies and Oxidations of Some Indole Derivatives", Heterocycles 1990, 30(2), 1131-1140.

Bobosik et al., "Synthesis of N-Phenylsulfonyl Protected Furo[3,2-b]pyrroles", Collect. Czech. Chem. Commun. 1994, 59(2), 499-502.

Boeshagen et al., "Ueber 3-Acylimino-3H-1.2-benzodithiole", Chem. Ber. 1968, 101(7), 2472- 2484.

Borza et al., "Selective NR1/2B N-Methyl-d-aspartate Receptor Antagonists among Indole-2-carboxamides and Benzimidazole-2-carboxamides" J. Med. Chem. 2007, 50(5), 901-914.

Braga et al., "Making crystals from crystals: a green route to crystal engineering and polymorphism", Chem. Commun. 2005(29), 3635-3645.

Bregant et al., "Orthogonally Protected Lanthionines: Synthesis and Use for the Solid-Phase Synthesis of an Analogue of Nisin Ring C", J. Org. Chem. 2005, 70(7), 2430-2438.

Brunner et al., "Asymmetrische Hydrierung von (Z)-.alpha.-(Acetylamino)-zimtsaure mit einem Rh/norphos-Katalysator", Angew. Chem. 1979, 91(8), 655-656.

Brunner-Guenat et al., "Esters of L-dopa: structure-hydrolysis relationships and ability to induce circling behaviour in an experimental model of hemiparkinsonism", J. Pharm. Pharmacol. 1995, 47(10), 861-869.

Bueno et al., "Dipeptides as effective prodrugs of the unnatural amino acid (+)-2-aminobicyclo[3.1.0]hexane-2,6-dicarboxylic acid (LY354740), a selective group II metabotropic glutamate receptor agonist." J. Med. Chem. 2005, 48(16), 5305-5320.

Bundgaard et al., "Esters of N,N-disubstituted 2-hydroxyacetamides as a novel highly biolabile prodrug type for carboxylic acid agents", J. Med. Chem 1987, 30(3), 451-454.

Byrn et al., "Solid-State Chemistry of Drugs", 2nd ed.; SSCI, Inc.: West Lafayette, Indiana, 1999; pp. 232-247.

Cai et al., "Synthesis of 2,4,5-Trisubstituted Oxazoles", Synthesis 2005(10), 1569-1571.

Calderon et al., "Novel 1-Phenylcycloalkanecarboxylic Acid Derivatives Are Potent and Selective .sigma.1 Ligands", J. Med. Chem. 1994, 37(15), 2285-2291.

Callis et al., "A Tandem Horner-Emmons Olefination-Conjugate Addition Approach to the Synthesis of 1,5-Disubstituted-6-azabicyclo[3.2.1]octanes Based on the AE Ring Structure of the Norditerpenoid Alkaloid Methyllycaconitine", J. Org. Chem. 1996, 61(14), 4634-4640.

Cartoon et al., "Lithiation reactions of 1-(2'-bromophenyl)pyrrole and related compounds", J. Organomet. Chem. 1981, 212(1), 1-9.

Chakraborty et al., "Synthesis and characterization of Boc-protected 4-amino- and 5-aminopyrrole-2-carboxylic acid methyl esters", Tetrahedron Lett. 2006, 47(27), 4631-4634.

Chapman et al., "The Analytical Reduction of Porphyrins to Pyrroles", Can. J. Chem. 1971, 49(21), 3544-3564.

Chaubey et al., "Kinetics of the Oxidation of Heterocyclic Aldehydes by Quinolinium Dichromate", Bull. Chem. Soc. Jpn. 2002, 75(10), 2215-2220.

Chen et al., "4,4-Difluoro-4-bora-3a,4a-diaza-s-indacene (BODIPY) Dyes Modified for Extended Conjugation and Restricted Bond Rotations", J. Org. Chem. 2000, 65(10), 2900-2906.

Chen et al., "Studies on the SAR and pharmacophore of mihiacipran derivatives as monoamine transporter inhibitors", Bioorg. Med. Chem. Lett. 2008, 18(4), 1346-1349.

Chimichi et al., "New 5-(2-ethenylsubstituted)-3(2H)-furanones with in vitro antiproliferative activity", Tetrahedron 2003, 59(28), 5215-5223.

Cottineau et al., "Synthesis and hypoglycemic evaluation of substituted pyrazole-4-carboxylic acids", Bioorg. Med. Chem. Lett. 2002, 12(16), 2105-2108.

Crane et al., "A Novel Enantioselective Synthetic Route to Omuralide Analogues with the Potential for Species Selectivity in Proteasome Inhibition", Org. Lett. 2001, 3(9), 1395-1397.

Cuevas-Yanez et al., "Rhodium(II) catalyzed intramolecular insertion of carbenoids derived from 2-pyrrolyl and 3-indolyl .alpha.-diazo-.beta.-ketoesters and .alpha.-diazoketones", Tetrahedron 2004, 60(7), 1505-1511.

Cyranski et al., "Aromaticity of dihetero analogues of pentalene dianion. X-Ray and ab initio studies of eight methyl furo[3,2-b]pyrrole-5-carboxylate derivatives and five methyl furo[2,3- b]pyrrole-5-carboxylate derivatives", Tetrahedon 2001, 57(42), 8867-8873.

Damaslo, A. R., "Alzheimer's Disease and Related Dementias" in "Cecil Textbook of Medicine", 20th ed., vol. 2; W.B. Saunders Co.: Philadelphia, 1996; pp. 1992-1996.

Dandarova et al., "13C NMR spectra of some substituted furo[3,2-b]pyrroles", Magn. Reson. Chem. 1990, 28(9), 830-831.

Das et al., "Synthesis of some N-substituted carbazoles and their larvicidal studies", J. Indian Chem. Soc. 2005, 82, 158-160.

Database Beilstein, Beilstein Institute for Organic Chemistry, Frankfurt-Main, DE; Database Accession No. BRN: 10196160 Abstract; and Eur. J. Org. Chem. 2005(21), 4670-4679.

Database Beilstein, Beilstein Institute for Organic Chemistry, Frankfurt-Main, DE; Database Accession No. BRN: 1074598 Abstract; and Can. J. Chem. 1978, 56(10), 1429-1434.

Database Beilstein, Beilstein Institute for Organic Chemistry, Frankfurt-Main, DE; Database Accession No. BRN: 4185621 Abstract; and Collect. Czech. Chem. Commun. 1986, 51(1), 106-111.

Database Beilstein, Beilstein Institute for Organic Chemistry, Frankfurt-Main, DE; Database Accession No. BRN: 4429388 Abstract; and Collect. Czech. Chem. Commun. 1984, 49(1), 65-70.

Database Beilstein, Beilstein Institute for Organic Chemistry, Frankfurt-Main, DE; Database Accession No. BRN: 7812555 Abstract; and Collect. Czech. Chem. Commun. 1997, 62(10), 1612- 1622.

Database Caplus on STN, Acc. No. 1977:83511, Koe, J. Pharmacol. Exp. Ther. 1976, 199(3), 649-661. [abstract].

De Luca et al., "A New, Simple Procedure for the Synthesis of Formyl Amides", Synlett 2004(14), 2570-2572.

Denmark et al., "Chiral fluoro ketones for catalytic asymmetric epoxidation of alkenes with oxone", J. Org. Chem. 2002, 67(10), 3479-3486.

Denmark et al., "Organocerium additions to SAMP-hydrazones: general synthesis of chiral amines", J. Am. Chem. Soc. 1987, 109(7), 2224-2225.

Dhanak et al., "Studies in the protection of pyrrole and indole derivatives", J. Chem. Soc., Perkin Trans. 1, 1986, 2181-2186.

Durrer et al., "Structure-metabolism relationships in the hydrolysis of nicotinate esters by rat liver and brain subcellular fractions", Pharm. Res. 1991, 8(7), 832-839.

Elghamry, "Synthesis of ethyl pyrrole-2-carboxylates: a regioselective cyclization of enaminones under knorr-type conditions", Synth. Commun. 2002, 32(6), 897-902.

Eliel, "Infelicitous stereochemical nomenclature", Chirality 1997, 9(5-6), 428-430.

El-Nagger et al., "Synthesis and Biological Activity of Some New Aminoacylcarbazole Derivatives. Part I", J. Heterocycl. Chem. 1982, 19, 1025-1028.

English et al., "Orally effective acid prodrugs of the beta-lactamase inhibitor sulbactam", J. Med. Chem. 1990, 33(1), 344-347.

Eras et al., "Reactivity of thienopyrroles. Synthesis of isomeric nitro and bromothienopyrroles", J. Heterocycl. Chem. 1984, 21(1), 215-217.

Estep, "An Efficient Synthesis of 4-Hydroxy-1H-indole-2-carbonitrile and Its Conversion to DPI 201-106", Synth. Commun. 1995, 25(4), 507-514.

Fagan et al., "A new approach to the core of roseophilin", Tetrahedron Lett. 1999, 40(33), 6117-6120.

Ferguson et al., "N-Acetyl-5,6-dihydrofuro[3,2-b]pyrid-2-one, C9H9NO3", Cryst. Struct. Comm. 1976, 5, 911-914.

Fischer et al., "On Benzisothiazolones: A Series with a Wide Range of Bacteriostatic and Fungistatic Activity", Arzneimittel-Forschung 1964, 14(12), 1301-1306.

Fischer et al., "Synthese einiger Pyrrole und lire Umsetzungen", Justus Liebigs Ann. Chem. 1932, 492(1), 128-155.

Fischer et al., "Synthesen der Opso- und Hamopyrrolcarbonsaure. Neue Synthese von Koproporphyrin. II", Justus Liebigs Ann. Chem. 1928, 462(1), 240-250.

Fischer et al., "Synthesen von Koproporphyrin I und II, sowie Mesoporphyrin II, V und XII", Justus Liebigs Ann. Chem. 1928, 466(1), 147-178.

Fisera et al., "Correlation of Kinetic Data of 1,3-Dipolar Cycloadditions of C-Benzoyl-Nphenylnitrones with the Homo Energies of Furan Derivatives", Collect. Czech. Chem. Commun. 1981, 46, 1504-1512.

Fisera et al., "Cycloadditions of C-Benzoyl-N-phenylnitrone with Furocondensed Derivatives", Collect. Czech. Chem. Commun. 1981, 46, 2421-2427.

Flaugh et al., "Synthesis of porphyrins. Deoxophylloerythroetioporphyrin", J. Am. Chem. Soc. 1968, 90(24), 6877-6879.

Foucaud et al., "The [1+4] cycloaddition of isocyanides with 1-aryl-2-nitro-l-propenes. Methyl 2- nitro-3-arylpropenoates and methyl 2-nitro-2,4-pentadienoates. Synthesis of 1-hydroxyindoles and 1-hydroxypyrroles", J. Org. Chem. 1983, 48(21), 3639-3644.

Fraga-Dubreuil et al., "Grafted ionic liquid-phase-supported synthesis of small organic molecules", Tetrahedron Lett. 2001, 42(35), 6097-6100.

Franci et al., "Asymmetric Catalysis with Chiral Phosphane/Phosphoramidite Ligands Derived from Quinoline (QUINAPHOS)", Angew. Chem. Int. Ed. 2000, 39(8), 1428-1430.

Frisell et al., "Flavoenzyme Catalysis. Substrate-Competitive Inhibition of D-Amino Acid Oxidase", J. Biol. Chem. 1956, 223, 75-83.

Fu et al., "Design and synthesis of novel bis(I-amino acid) ester prodrugs of 9[2-(phosphonomethoxy)ethyl]adenine (PMEA) with improved anti-HBV activity", Bioorg. Med. Chem. Lett. 2007, 17(2), 465-470.

Fukuda et al., "Tensidols, New Potentiators of Antifungal Miconazole Activity, Produced by Aspergillus niger FK1-2342", J. Antibiot. 2006, 59(8), 480-485.

Gabbutt et al., "A Facile Synthesis of Some Benzothiopyrano[4,3-b]pyrroles", J. Chem. Res. (S) 1997(3), 102-103.

Gale et al., "Preparation and Reactions of 5-Carbethoxythieno[3,2-b]pyrrole and Some of Its Derivatives", J. Org. Chem. 1964, 29(8), 2160-2165.

Garg et al., "Development of an Enantiodivergent Strategy for the Total Synthesis of (+)- and (-)- Dragmacidin F from a Single Enantiomer of Quinic Acid", J. Am. Chem. Soc. 2005, 127(16), 5970- 5978.

Gelas-Mialhe et al., "Photochemical heterocyclization of functionalized dienamines", J. Org. Chem. 1987, 52(24), 5395-5400.

Gelas-Mialhe et al., "Reactivite des N-vinylaziridines fonctionnalisees. Synthese de derives des .alpha.,.beta.-dehydro .alpha.-amino acides", Can. J. Chem. 1982, 60(22), 2830-2851.

Geraldine et al., "How an increase in the carbon chain length of the ester moiety affects the stability of a homologous series of oxprenolol esters in the presence of biological enzymes", J. Pharm. Sci. 1998, 87(7), 880-885.

Gross et al., "Direct observation of 1-azafulven-6-one and annelated derivatives", J. Chem. Soc., Chem. Commun. 1982(6), 360-361.

Grygorenko et al., "Stereoselective synthesis of 2,4-methanoproline homologues", Tetrahedron Asymmetry 2006, 17(2), 252-258.

Guan et al., "Design and synthesis of aminopropyl tetrahydroindole-based indolin-2-ones as selective and potent inhibitors of Src and Yes tyrosine kinase", Bioorg. Med. Chem. Lett. 2004, 14(1), 187-190.

Haginoya et al., "Synthesis and conformational analysis of a non-amidine factor Xa inhibitor that incorporates 5-methyl-4,5,6,7-tetrahydrothiazolo[5,4-c]pyridine as S4 binding element", J. Med. Chem. 2004, 47(21), 5167-5182.

Haj-Yehia et al., "Pharmacokinetic analysis of the structural requirements for forming "stable" analogues of valpromide", Pharm. Res. 1992, 9(8), 1058-1063.

Haj-Yehia et al., "Structure-pharmacokinetic relationships in a series of valpromide derivatives with antiepileptic activity", Pharm. Res. 1989, 6(8), 683-689.

Harada et al., "A Simple Preparation of Chloromethyl Esters of the Blocked Amino Acids", Synth. Commun. 1994, 24(6), 767-772.

Harrak et al.,"PtCl2-Catalyzed Cycloisomerizations of 5-En- 1 -yn-3-ol Systems", J. Am. Chem. Soc. 2004, 126(28), 8656-8657.

Harrison et al., "Cyclopenta[b]indoles. Part 2. Model studies towards the tremorgenic mycotoxins", J. Chem. Soc. Perkin Trans. 1 1995(9), 1131-1136.

Harwood et al., "Tandem generation and intramolecular trapping of chiral stabilised azomethine ylids with alkyne dipolarophiles", Tetrahedron Lett. 1993, 34(41), 6603-6606.

Hauptmann et al., "Beitrage zum Reaktionsverhalten von 2-Aminovinylcarbonylverbindungen", Journal fur Praktische Chemie 1972, 314(2), 353-364.

Hauptmann et al., "Eine neue Synthese substituierter Thiophene und Pyrrole", Tetrahedron Lett. 1968, 9(11), 1317-1319.

Hemetsberger et al., "Synthese und Thermolyse von .alpha.-Azidoacrylestern", Monatsh. Chem. 1972, 103(1), 194-204.

Hillenweck et al., "Chlorothalonil Biotransformation by Gastrointestinal Microflora: In Vitro Comparative Approach in Rat, Dog, and Human", Pestic. Biochem. Physiol. 1997, 58(1), 34-48.

Hilton et al., "Observations on the reactivity of thiyl radicals derived from 3,6- epidithiodiketopiperazine-2,5-diones and related congeners", Bioorg. Med. Chem. Lett. 2005, 15(9), 2239-2242.

Hoffman, R. V., "Organic Chemistry: An Intermediate Text, Second Edition"; Wiley: Hoboken, 2004; pp. 124 and 138-144.

Holmes et al., "Reactions of N-Benzylthieno[3,2-b]pyrrole. I. Metalation and an Electrophilic Substitution", J. Org. Chem. 1964, 29(8), 2155-2160.

Hori, M., "Syntheses of Analgesics. XIV. Aminocyclohexane Derivatives. 8.", Yakugaku Zasshi 1958, 78, 11-14.

Howarth et al., "Pyrroles and related compounds. Part XXVI. Pyrrole beta-keto-esters", J. Chem. Soc. Perkin Trans., 490-501, (1974).

Hu et al., "Synthesis of a Porphyrin with Fused Five- and Seven-membered Exocyclic Rings from a Cross-conjugated Tetracydic Dipyrrole", Synlett 1994(11), 909-910.

Ilyin et al., "Synthesis of Annelated Azaheterocycles Containing a 5-Carbamoylpyrazin-3-one Fragment by a Modification of the Four-Component Ugi Reaction", Eur. J. Org. Chem. 2005(21), 4670-4679.

Ingram et al., "Investigation of enzyme activity by SERRS using poly-functionalised benzotriazole derivatives as enzyme substrates", Org. Biomol. Chem. 2006, 4(15), 2869-2873.

Inukai et al., "ortho-Disubstituted F-Benzenes. III. Preparation of (F-Benzo)heterocyclic Compounds from F-Benzoic Acid and F-Phenol, and the Reactions of Some Intermediary F-Benzoyland F-Phenoxy Compounds", Bull. Chem. Soc. Jpn. 1981, 54(11), 3447-3452.

Iranpoor et al., "A Rapid and Facile Conversion of Primary Amides and Aldoximes to Nitriles and Ketoximes to Amides with Triphenylphosphine and N-Chlorosuccinimide", Synth. Commun. 2002, 32(16), 2535-2541.

Isoherranen et al., "New CNS-active drugs which are second-generation valproic acid: can they lead to the development of a magic bullet?", Curr. Opin. Neurol. 2003, 16(2), 203-211.

Jacob et al., "gamma-Aminobutyric acid esters. 2. Synthesis, brain uptake, and pharmacological properties of lipid esters of gamma-aminobutyric acid", J. Med. Chem. 1985, 28(1), 106-110.

Java et al., "Chimie Organique.—Synthese de selenolo, furo et pyrrolopyrroles", C. R. Acad. Sc. Paris 1975, 281 Serie C (19), 793-795.

Jolicoeur et al., "Pyrrole protection", Tetrahedron 2006, 62(0), 11531-11563.

Katritzky et al., "Efficient Conversion of Carboxylic Acids into N-Acylbenzotriazoles", Synthesis 2003(18), 2795-2798.

Katritzky et al., "Novel Synthesis of Bicycles with Fused Pyrrole, Indole, Oxazole, and Imidazole Rings", J. Org. Chem. 2004, 69(26), 9313-9315.

Katritzky et al., "Regiospecific C-Acylation of Pyrroles and Indoles Using N-Acylbenzotriazoles", J. Org. Chem. 2003, 68(14), 5720-5723.

Katterle et al., "A Heck-Type Coupling for the Synthesis of Novel Bridged MetallochlorinFullerene C60 Dyads", European J. Org. Chem. 2006(2), 414-422.

Keener etal., "Synthesis of 6-substituted thieno[3,2-b]pyrroles", J. Org. Chem. 1968, 33(4), 1355-1359.

Kesel, "Synthesis of Novel Test Compounds for Antiviral Chemotherapy of Severe Acute Respiratory Syndrome (SARS)", Curr. Med. Chem. 2005, 12(18), 2095-2162.

Khanna et al., "Evaluation of glycolamide esters of indomethacin as potential cyclooxygenase-2 (COX-2) inhibitors", Bioorg. Med. Chem. 2006, 14(14), 4820-4833.

Kittredge et al., "alpha-Helical Polypeptide Films Grown From Sulfide or Thiol Linkers on Gold Surfaces", Hely. Chim. Acta 2002, 85(3), 788-798.

Kleinspehn et al., "The Synthesis of Some .beta., .beta.-Dipyrrylpropionic Esters", J. Am. Chem. Soc. 1954, 76(22), 5641-5646.

Koe, "Molecular geometry of inhibitors of the uptake of catecholamines and serotonin in synaptosomal preparations of rat brain", J. Pharmacol. Exp. Ther. 1976, 199(3), 649-661.

Kralovicova et al., "Electrophilic Substitution Reactions of Furo[3,2-b]pyrrole Derivatives", Collect. Czech. Chem. Commun. 1986, 51(1), 106-111.

Krayushkin et al., "Synthesis of Photochromic 1,2-Dihetarylethene Using Regioselective Acylation of Thienopyrroles", Org. Lett. 2002, 4(22), 3879-3881.

Kren et al., "Clustered ergot alkaloids modulate cell-mediated cytotoxicity", Bioorg. Med. Chem. 2002, 10(2), 415-424.

Krutosikova et al., "Addition and Cycloaddition Reactions of Furo[3,2-b]pyrroles and Their Benzo[b] Analogues: An NMR Study of Structure of Products", Collect. Czech. Chem. Commun. 1988, 53(5), 1770-1778.

Krutosikova et al., "Effect of microwave irradiation on reaction of furo[3,2-b]pyrrole and furo[2,3-b]pyrrole-2-carbaldehydes with some active methylene compounds", ARKIVOC 2000(iii), 409-420.

Krutosikova et al., "Reactions of Ethyl 2-(4-chlorophenyl)-4H-furo[3,2-b]pyrrole-5-carboxylate", Collect. Czech. Chem. Commun. 1980, 45(111), 2949-2957.

Krutosikova etal., "Reactions of furo[3,2-b]pyrroles and their benzo[b] analogues", Chem. Papers 1988, 42(1), 89-95.

Krutosikova et al., "Reactions of Methyl 2-Formylfuro[3,2-b]pyrrole-5-carboxylates", Chem. Papers 1996, 50(2), 72-76.

Krutosikova etal., "Substituted 4-Benzylfuro[3,2-b]pyrroles", Collect. Czech. Chem. Commun. 1992, 57(5), 1487-1494.

Krutosikova et al., "Substituted Vinyl Azides in the Synthesis of Condensed Nitrogen Heterocycles", Chem. Papers 1994, 48(4), 268-273.

Krutosikova etal., "Synthesis and Reactions of 4-Oxiranylmethylfuro[3,2-b]pyrroles and Their Benzo Derivatives", Chemistry of Heterocyclic Compounds 2001, 37(12), 1511-1517.

Krutosikova etal., "Synthesis and Reactions of 8-Hydrazinofuro[2¹,3':4,5]pyrrolo-[1,2-d][1,2,4]triazines", Collect. Czech. Chem. Commun. 1997, 62(10), 1612-1622.

Krutosikova etal., "Synthesis and Reactions of Furo[2,3-b]pyrroles", Molecules 1997, 2(4), 69-79.

Krutosikova et al., "Synthesis and Reactions of Furocondensed Derivatives", Collect. Czech. Chem. Commun. 1984, 49(1), 65-70.

Krutosikova etal., "Synthesis and Reactions of Substituted Furo[3,2-b]pyrrole Derivatives", Collect. Czech. Chem. Commun. 1981, 46, 2564-2572.

Kukolja et al., "Orally absorbable cephalosporin antibiotics. 2. Structure-activity studies of bicyclic glycine derivatives of 7-aminodeacetoxycephalosporanic acid", J. Med. Chem. 1985, 28(12), 1896- 1903.

Kumar et al., "Synthesis and biological evaluation of thiophene [3,2-b] pyrrole derivatives as potential anti-inflammatory agents", Bioorg. Med. Chem. 2004, 12(5), 1221-1230.

Kuo et al., "G-protein coupled receptors: SAR analyses of neurotransmitters and antagonists", J. Clin. Pharm. Ther. 2004, 29(3), 279-298.

Lamboley et al., "Synthesis and Properties of Conformationally Constrained Analogues of Floral-Type Odorants", Helv. Chim. Acta 2004, 87(7), 1767-1793.

Lash et al., "Influence of carbocyclic rings on porphyrin cyclizations: synthesis of geochemically significant cycloalkanoporphyrins", Energy Fuels 1990, 4(6), 668-674.

Lash et al., "Normal and Abnormal Heme Biosynthesis. 2.1 Synthesis and Metabolism of Type-III Pentacarboxylic Porphyrinogens: Further Experimental Evidence for the Enzymic Clockwise Decarboxylation of Uroporphyrinogen-III", J. Org. Chem. 1999, 64(2), 478-487.

Lash et al., "Porphyrins with exocyclic rings. 1. Chemistry of 4,5,6,7-tetrahydro-1H-indoles: synthesis of acetoxy derivatives, dihydroindoles, and novel porphyrins with four exocyclic rings", J. Org. Chem. 1992, 57(18), 4809-4820.

Lash et al., "Porphyrins with exocyclic rings. Part 3. A reassessment on the utility of cyclopenta[b]pyrroles in the synthesis of porphyrin molecular fossils. Preparation of three type II porphyrins related to deoxophylloerythroetioporphyrin (DPEP)", Tetrahedron 1993, 49(20), 4159- 4172.

Lash et al., "Recent advances in the synthesis of porphyrins with five-membered exocyclic rings", Energy Fuels 1993, 7(2), 172-178.

Law et al., "The synthesis and chemistry of azolenines. Part 2. A general synthesis of pyrrole-2-carboxylic acid derivatives by the reaction of 2H-azirines with enamines, and the crystal and molecular structure of ethyl 3-phenyl-4,5,6,7-tetrahydroindole-2-carboxylate", J. Chem. Soc. Perkin Trans. 1 1984, 111-118.

Layzer, R. B., "Section Five—Degenerative Diseases of the Nervous System" in "Cecil Textbook of Medicine", 20th ed., vol. 2; W.B. Saunders Co.: Philadelphia, 1996; pp. 2050-2057.

Lee at al., "Amphiphilic amino acid copolymers as stabilizers for the preparation of nanocrystal dispersion", Eur. J. Pharm. Sci. 2005, 24(5), 441-449.

Lee et al., "An Effective and Convenient Esterification of Cephalosporin Derivatives by Using Quartemary Ammonium Salts as Catalysts", Synth. Commun. 1998, 28(23), 4345-4354.

Lerche et al., "Umsetzungen mit Monohydrazonen von Dicarbonylverbindungen, V: Umsetzungen von Hydrazonoethylidenammonium-Salzen and Hydrazonoaldehyden mit Grignard-Verbindungen", Chem. Ber. 1978, 111(3), 1195-1209.

Li et al., "Synthesis of deoxophylloerythroetioporphyrin (DPEP) and three ring homologs by an improved b-bilene methodology", Tetrahedron Left. 1998, 39(47), 8571-8574.

Liederer et al., "Enzymes involved in the bioconversion of ester-based prodrugs", J. Pharm. Sci. 2006, 95(6), 1177-1195.

Liederer et al., "Stability of oxymethyl-modified coumarinic acid cyclic prodrugs of diastereomeric opioid peptides in biological media from various animal species including human", J. Pharm. Sci. 2005, 94(10), 2198-2206.

Liu et al., "Facile construction of the pentacyclic framework of subincanadine B. Synthesis of 20-deethylenylated subincanadine B and 19,20-dihydrosubincanadine B", Org. Lett. 2006, 8(1), 115-118.

Liu et al., "Indole-5-phenylcarbamate derivatives as human non-pancreatic secretory phospholipase A2 inhibitor", Bioorg. Med. Chem. Lett. 2005, 15(20), 4540-4542.

Liu et al., "The synthesis of camostat intermediate", Huaxue Shiji, 2006, 28(6), 371-372.

Lkegami et al., "Synthesis and pharmacological activity of 0-(5-isoxazoly1)-L-serine", Chem. Pharm. Bull. 2000, 48(2), 278-280.

Ma et al., "Hydrolysis of angiotensin II receptor blocker prodrug olmesartan medoxomil by human serum albumin and identification of its catalytic active sites", Drug Metab. Dispos. 2005, 33(12), 1911-1919.

Majumdar et al., ".alpha.-(1H-Imidazol-1-yDalkyl (IMIDA) carboxylic acid esters as prodrugs of carboxylic acid containing drugs", Tetrahedron Lett. 2007, 48(26), 4609-4611.

Mal et al., "Regioselective synthesis of 1-hydroxycarbazoles via anionic [4+2] cycloaddition of furoindolones: a short synthesis of murrayafoline-A", Tetrahedron Lett. 2006, 47(7), 1071-1075.

Mamber et al., "Tubulin polymerization by paclitaxel (taxol) phosphate prodrugs after metabolic activation with alkaline phosphatase", J. Pharmacol. Exp. Ther. 1995, 274(2), 877-883.

Mandel et al., "Neuroprotective Strategies in Parkinson's Disease: An Update on Progress", CNS Drugs 2003, 17(10), 729-762.

Marrel et al., "L-Dopa esters as potential prodrugs 1. Physicochemical properties", Eur. J. Med. Chem. 1985, 20(5), 459-465.

Marrel et al., "L-Dopa esters as potential prodrugs 2. Chemical and enzymatic-hydrolysis", Eur. J. Med. Chem. 1985, 20(5), 467-470.

Martin et al., "Das Diazo-chinon von PQQ als mogliches Reagenz fur die Kartierung von Chinoproteinen mittels Photoaffmitatsmarkierung", Helv. Chim. Acta 1993, 76(4), 1674-1677.

Martin et al., "Do structurally similar molecules have similar biological activity?", J. Med. Chem. 2002, 45(19), 4350-4358.

McConnaughie et al., "Novel Acridine-Triazenes as Prototype Combilexins: Synthesis, DNA Binding, and Biological Activity" J. Med. Chem. 1995, 38(18), 3488-3501.

Mclaughlin, "Suzuki-Miyaura Cross-Coupling of Benzylic Phosphates with Arylboronic Acids", Org. Lett. 2005, 7(22), 4875-4878.

Medforth et al., "Nonplanar distortion modes for highly substituted porphyrins", J. Am. Chem. Soc. 1992, 114(25), 9859-9869 deethylenylated subincanadine B and 19,20-dihydrosubincanadine B, Org. Lett. 2006, 8(1), 115-118.

Meltzer et al., "The synthesis of bivalent 2.beta.-carbomethoxy-3.beta.-(3,4-dichlorophenyI)-8-heterobicyclo[3.2.1]o- ctanes as probes for proximal binding sites on the dopamine and serotonin transporters", Bioorg. Med. Chem. 2008, 16(4), 1832-1841.

Mergen et al., "Antiepileptic activity of 1,3-dihexadecanoylamino-2-valproyl-propan-2-ol, a prodnig of valproic acid endowed with a tropism for the central nervous system", J. Pharm. Pharmacol. 1991, 43(11), 815-816.

Merisor et al., "Synthesis of New Derivatives in the lzoxazole Class with Potential Antimicrobial Activity", Rev. Chim. (Bucharest, Romania) 2001, 52(4), 206-209.

Miao et al., "Benzamide derivatives as blockers of Kv1.3 ion channel", Bioorg. Med. Chem. Lett. 2003, 13(6), 1161-1164.

Mikhaleva et al., "Expedient synthesis of 1-vinylpyrrole-2-carbaldehydes", Tetrahedron Lett. 2006, 47(22), 3693-3696.

Miki et al., "Synthesis of 3-Methoxyellipticine and Ellipticine by Friedel-Crafts Reaction of Indole2,3-dicarboxylic Anhydride and Selective Demethylation", Heterocycles 2005, 65(11), 2693-2703.

Milkiewicz et al., "Synthesis of a novel series of tetra-substituted furan[3,2-b]pyrroles", Tetrahedron Lett. 2003, 44(22), 4257-4260.

Mishra et al., "Synthesis, characterization and pharmacological evaluation of amide prodnigs of ketorolac", Eur. J. Med. Chem. 2008, 43(11), 2464-2472.

Mokhallalati et al., "A single-pot synthesis of 1,1,2-trisubstituted 1,2-dihydronaphthalenes in high enantiomeric purity", Tetrahedron Lett. 1994, 35(25), 4267-4270.

Montero et al., "Solid-Phase Combinatorial Synthesis of Peptide-Biphenyl Hybrids as Calpain Inhibitors", Org. Lett. 2004, 6(22), 4089-4092.

Morgan et al., "Synthesis of hydrocarbon-strapped porphyrins containing quinone and phenolic groups", J. Org. Chem. 1987, 52(24), 5364-5374.

Morissette et al., "High-throughput crystallization: polymorphs, salts, co-crystals and solvates of pharmaceutical solids", Adv. Drug Deliv. Rev. 2004, 56(3), 275-300.

Mork et al., "Stereoselective enzymatic hydrolysis of various ester prodrugs of ibuprofen and flurbiprofen in human plasma", Pharm. Res. 1992, 9(4), 492-496.

Muchowski et al., "Protecting groups for the pyrrole and indole nitrogen atom. The [2-(trimethylsilypethoxy]methyl moiety. Lithiation of 14[2-(trimethylsilypethoxy]methylipyrrole", J. Org. Chem. 1984, 49(1), 203-205.

Murakami et al., "The Friedel-Crafts Acylation of Ethyl Pyrrole-2-carboxylate. Scope, Limitations, and Application to Synthesis of 7-Substituted Indoles", Heterocycles 1988, 27(8), 1855-1860.

Nacci et al., "Polycondensed Heterocycles. I. Synthesis of 11-0xo-5H,11H-pyrrolo[2,1-c][1,4]benzothiazepine, Derivative of a Novel Ring System", J. Heterocycl. Chem. 1985, 22(2), 259-263.

Nacci et al., "Polycondensed Heterocycles. II. A New Preparative Route to 11-0xo-5H,11Hpyrrolo[2,1-c][1,4]benzothiazepine", J. Heterocycl. Chem. 1986, 23(3), 769-773.

Nagarathnam et al., "Design and Synthesis of Novel .alpha. 1 a Adrenoceptor-Selective Dihydropyridine Antagonists for the Treatment of Benign Prostatic Hyperplasia", J. Med. Chem. 1998, 41(26), 5320-5333.

Nagel et al., "Enantioselektive Katalyse, 4. Synthese N-substituierter (R,R)-3,4- Bis(diphenylphosphino)-pyrrolidine und Anwendung ihrer Rhodiumkomplexe zur asymmetrischen Hydrierung von .alpha.- (Acylamino)acrylsaure-Derivaten", Chem. Ber. 1986, 119(11), 3326-3343.

Narasimhan et al., "A QSAR approach for the prediction of stability of benzoglycolamide ester prodrugs", Chem. Pharm. Bull. 2006, 54(8), 1067-1071.

Nelson et al., "Stereoselective Synthesis of a Potent Thrombin Inhibitor by a Novel P2-P3 Lactone Ring Opening", J. Org. Chem. 2004, 69(11), 3620-3627.

New et al., "The thieno[3,2-c]pyridine and furo[3,2-c]pyridine rings: new pharmacophores with potential antipsychotic activity", J. Med. Chem. 1989, 32(6), 1147-1156.

Newman-Evans et al., "The influence of intramolecular dynamics on branching ratios in thermal rearrangements", J. Org. Chem. 1990, 55(2), 695-711.

Nielsen et al., "Bioreversible quaternary N-acyloxymethyl derivatives of the tertiary amines bupivacaine and lidocaine—synthesis, aqueous solubility and stability in buffer, human plasma and simulated intestinal fluid", Eur. J. Pharm. Sci. 2005, 24(5), 433-440.

Nielsen et al., "Glycolamide esters as biolabile prodrugs of carboxylic acid agents: Synthesis, stability, bioconversion, and physicochemical properties", J. Pharm. Sci. 1988, 77(4), 285-298.

Nudelman et al., "Novel anticancer prodrugs of butyric acid. 2.", J. Med. Chem. 1992, 35(4), 687-694.

Nudelman et al., "The role of intracellularly released formaldehyde and butyric acid in the anticancer activity of acyloxyallcyl esters." J. Med. Chem. 2005, 48(4), 1042-1054.

Ogawa et al "Preparation of oxygen-bridged aza[15]- and aza[17]annulene dicarboxylates by intramolecular azide cyclization", Tetrahedron Lett. 1988, 29(2), 219-222.

Ojida et al., "Highly Enantioselective Reformatslcy Reaction of Ketones: Chelation-Assisted Enantioface Discrimination", Org. Leff 2002, 4(18), 3051-3054.

Ouyang et al., "Steric hindrance is a key factor in the coupling reaction of (acyloxy) alkyl-.alpha.halides with phenols to make a new promoiety for prodrugs", Tetrahedron Lett. 2002, 43(4), 577-579.

Pane et al., "Regioselectivity of pyrrole synthesis from diethyl aminomalonate and 1,3-diketones: further observations", J. Org. Chem. 1987, 52(18), 3986-3993.

Parikh et al., "The Use of Amino Acid Oxidases for the Small-scale Preparation of the Optical Isomers of Amino Acids", J. Am. Chem. Soc. 1958, 80(4), 953-958.

Paxeus et al., "Screening for non-regulated organic compounds in municipal wastewater in Goteborg, Sweden", Water Sci. Technol. 1996, 33(6), 9-15.

Perez-Balderas et al., "Synthesis of multivalent neoglycoconjugates by 1,3 dipolar cycloaddition of nitrile oxides and alkynes and evaluation of their lectin-binding affinities", Tetrahedron 2005, 61(39), 9338-9348.

Pfeiffer et al., "Synthesen and Eigenschaften von Pyrrolindigo-Verbindungen", Liebigs Ann. Chem. 1980(4), 564-589.

Poszavacz et al., "New Synthesis of Naratriptan", Heterocycles 2006, 68(4), 713-719.

Puterova et al., "Reaction of Substituted Furan-2-carboxaldehydes and Furo[b]pyrrole Type Aldehydes with Hippuric Acid", Molecules 2004, 9(1), 11-21.

Puterova et al., "Reactions of Substituted Furan-2-carboxaldehydes and Furo[b]pyrrole Type Aldehydes with Benzothiazolium Salts", Molecules 2004, 9(4), 241-255.

Quizon-Colquitt et al., "Porphyrins with exocyclic rings. Part 4. An improved one step synthesis of cyclopenta[b]pyrroles", J. Heterocycl. Chem. 1993, 30(2), 477-482.

Rautio et al., "Synthesis and in Vitro Evaluation of Novel Morpholinyl- and Methylpiperazinylacyloxyalkyl Prodrugs of 2-(6-Methoxy-2-naphthyl)propionic Acid (Naproxen) for Topical Drug Delivery", J. Med. Chem. 2000, 43(8), 1489-1494.

Rodriguez et al., "Conformational and molecular study of the 4-(2-carboniethyl)-1,2,3,4-tetrahydrocyclopent[b]indole", Tetrahedron 1985, 41(18), 3813-3823.

Romanova et al., "DC Polarographic and UV Spectrometric Studies of Substituted Furo[3,2-b]- and Furo[2,3-b]pyrroles", Collect. Czech. Chem. Commun. 2001, 66(11), 1615-1622.

Rosati et al., "Cephalosporins to carbapenems: 1-oxygenated carbapenems and carbapenams.", J. Med. Chem. 1990, 33(1), 291-297.

Rose et al., "Preclinical antitumor activity of water-soluble paclitaxel derivatives", Cancer Chemother. Pharmacol. 1997, 39(6), 486-492.

Salim et al., "Pharmacokinetic analysis of esteric prodrugs of valproic acid", Pharm. Res. 1990, 7(9), S222.

Sambasivarao etal., "Synthetic approach to pentaleno[2,1-b:5,4-bldiindoles", J. Org. Chem. 1990, 55(12), 3858-3866.

Sandham et al., "Synthesis and biological properties of novel glucocorticoid androstene C-17 furoate esters", Bioorg. Med. Chem. 2004, 12(19), 5213-5224.

Sandler et al., "Organic Functional Group Preparations", vol. 3; Academic Press: New York, 1972; pp. 372-381.

Satake et al., "The Reaction of Electron Excess Aromatic Heterocycle, 1,4-Dihydropyrrolo[3,2- b]pyrrole and Some Related Compounds with Chlorosulfonyl Isocyanate (CSI)", Heterocycles 1996, 43(11), 2361-2365.

Scott etal., "Preparation and Reductive Cyclization of Some Carbon-Alkylated Derivatives of Ethyl 3-Nitro-2-thienylpyruvate", J. Org. Chem. 1964, 29(8), 2165-2168.

Sergievskaya et al., "N-Bis(chloroethyl)amines with Alicyclic and Aromatic Radicals in the Molecules. II.", Zhurnal Obshchei Khimii 1958, 28, 1845-1849. [translation].

Severin et al., "Umsetzungen von Ketonen mit azavinylogen Saureamiden", Chem. Ber. 1975, 108(5), 1756-1767.

Sewald et al., "Synthesis of homochiral camphor annulated pyrrole derivatives", Tetrahedron Asymmetry 1996, 7(5), 1269-1272.

Sha et al., "Synthesis of 2,4-Dihydropyrrolo[3,4-b]pyrroles and 4,6-Dihydro-2H-dipyrrolo[3,4- b:3',4'-d]pyrroles", Heterocycles 1990, 31(4), 603-609.

Shaaya et al., "Anhydride prodrugs for nonsteroidal anti-inflammatory drugs", Pharm. Res. 2003, 20(2), 205-211.

Shek, "Chemical delivery systems and prodnigs of anticonvulsive drugs", Adv. Drug Deliv. Rev. 1994, 14(2-3), 227-241.

Shirai et al., "Reduction of 1-(m-methoxyphenyl)-4-oxocycloalkanecarbonitriles with lithium aluminum hydride", Nagoya-shiritsu Daigaku Yakugakubu Kenlcyu Nenpo 1969, 17, 33-37.

Shirai et al., "Synthesis of spiro[4-hydroxycyclohexane-1,4,2',3'-dihydro-6'-methoxy-1'-substituted2'—methyl-1'Hisoquinoline]", Chem. Pharm. Bull. 1972, 20(1), 41-46.

Shvedov et al., "Monoarylhydrazones of di- and tricarbonyl compounds in the Knorr synthesis of pyrroles", Khimiya Geterotsiklicheskikh Soedinenii 1972(3), 342-344. [translation].

Silvestri et al., "Simple, short peptide derivatives of a sulfonylindolecarboxamide (L-737,126) active in vitro against HIV-1 wild type and variants carrying non-nucleoside reverse transcriptase inhibitor resistance mutations.", J. Med. Chem. 2004, 47(15), 3892-3896.

Sivy et al., "Structure of a furo[3,2-b]pyrrole derivative", Acta Crystallogr. 1988, C44(11), 2032- 2033.

Skolnick et al., "Antidepressant-like actions of DOV 21,947: a "triple" reuptake inhibitor", Eur. J. Pharmacol. 2003, 461(23), 99-104.

Slawik et al., "Lipophilicity of a series of 1,2-benzisothiazol-3(2H)-ones determined by reversed-phase thin-layer chromatography", J. Chromatogr. A 2002, 952(1-2), 295-299.

Sleath et al., "Synthesis of 7,9-didecarboxymethoxatin (4,5-dihydro-4,5-dioxo-1H-pyrrolo[2,3-f]quinoline-2-carboxylic acid) and comparison of its chemical properties with those of methoxatin and analogous o-quinones. Model studies directed toward the action of PQQ requiring bacterial oxidoreductases and mammalian plasma amine oxidase", J. Am. Chem. Soc. 1985, 107(11), 3328-3338.

Sleziak et al., "Furo[2,3-b]pyrrole Derivatives. Syntheses and Reactions in the Furan and Pyrrole Ring", Pol. J. Chem. 2000, 74(2), 207-217.

Sleziak et al., "Reactions of Furo[2,3-b]pyrrole and Furo[3,2-b]pyrrole-Type Aldehydes", Collect. Czech. Chem. Commun. 1999, 64(7), 1135-1146.

Smith et al., "Deacylation and deformylation of pyrroles", J. Org. Chem. 1983, 48(24), 4779-4781.

Snyder et al., "Synthesis of the Thieno [3,2-b]pyrrole System", J. Am. Chem. Soc. 1957, 79(10), 2556-2559.

Sohma et al., "Controlled Drug Release: Design and Application of New Water-soluble Prodrugs" in "Peptide Science 2001"; Aoyagi, H., Ed.; the Japanese Peptide Society, 2002; pp. 249-252.

Sorotskaya et al., "The Series of Substituted Butanolides and Butenolides. IV. 4-Arylidene(heteroarylidene)-2-butenolides", Zhurnal Organicheskoi Khimii 1989, 25(1), 175-182. [translation].

Soth et al., "Recherches en serie heterocyclique. XXIX. Sur des voies d'acces a des thieno, selenolo, furo et pyrrolopyrroles", Can. J. Chem. 1978, 56(10), 1429-1434.

Sparey et al., "The discovery of fused pyrrole carboxylic acids as novel, potent d-amino acid oxidase (DAO) inhibitors", Bioorg. Med. Chem. Lett. 2008, 18(11), 3386-3391.

STN Registry File No. 67268-37-5. Registry File. Retrieved from STN Mar. 17, 2008. One page.

Stuart et al., "Cobalt-mediated Alkylation of Siloxy Furans", Heterocycles 1991, 32(5), 949-963.

Svahn et al., "Tranexamic acid derivatives with enhanced absorption", J. Med. Chem. 1986, 29(4), 448-453.

Takahashi et al., "Asymmetric .alpha.-Substituted Phenethylamines. I. Synthesis of Optically Pure 1-Aryl-N-(2'-hydroxy-l'isopropylethyl)-2-phenylethylamines", Chem. Pharm. Bull. 1982, 30(9), 3160-3166.

Tammara et al., "Morpholinoalkyl ester prochugs of diclofenac: synthesis, in vitro and in vivo evaluation", J. Pharm. Sci. 1994, 83(5), 644-648.

Treibs et al., "Uber einige Pyrrolderivate mit angegliedertem isocyclischem Ring. Bz-Tetrahydrindole and Cyclopentenopyrrole", Justus Liebigs Ann. Chem. 1935, 517, 152-169.

Trost et al., "Palladium-Catalyzed Enantioselective C-3 Allylation of 3-Substituted-1H-Indoles Using Trialkylboranes", J. Am. Chem. Soc. 2006, 128(19), 6314-6315.

Ueda et al., "Novel water soluble phosphate prodrugs of taxol.RTM. possessing in vivo antitumor activity", Bioorg. Med. Chem. Lett. 1993, 3(8), 1761-1766.

Ueda et al., "Novel, water-soluble phosphate derivatives of 2'-ethoxy carbonylpaclitaxel as potential prodrugs of paclitaxel: Synthesis and antitumor evaluation", Bioorg. Med. Chem. Lett. 1995, 5(3), 247-252.

Urbach et al., "Eine einfache diastereoselektive Synthese von (1SR,3SR,5SR)-2-Azabicyclo [3.3.0] octan-3-carbonsaure", Tetrahedron Lett. 1985, 26(15), 1839-1842.

Van Herk et al., "Pyrazole Derivatives as Partial Agonists for the Nicotinic Acid Receptor", J. Med. Chem. 2003, 46(18), 3945-3951.

Vicini et al., "Biological studies on 1,2-benzisothiazole derivatives. I. Evaluation of antibacterial, antifungal and DNA-damaging activity", Farmaco 1989, 44(5), 511-517.

Vicini etal., "Sintesi e proprieta antiflogistiche antipiretiche ed analgesiche di 5-(1,2-benzisotiazolil)tetrazoli", Farmaco Sci. 1986, 41(2), 111-118.

Vicini et al., "Sintesi e proprieta antiflogistiche antipiretiche ed analgesiche di acidi 5-benzisotiazolilalcanoici e di loro derivati funzionali", Fannaco Sci. 1984, 39(10), 817-829.

Vippagunta etal., "Crystalline solids", Adv. Drug Deliv. Rev. 2001, 48(1), 3-26.

Viswanathan et al., "Free Radical-Mediated Aryl Amination and its use in a Convergent [3+2] Strategy for Enantioselective Indoline .alpha.-Amino Acid Synthesis", J. Am. Chem. Soc. 2003, 125(1), 163-168.

Vitali et al., "Ricerche nella classe dei fitocidi 3-benzisotiazolacetici", Farmaco Sci. 1973, 28(1), 8-18.

Vogel et al., "Cycloalkano-2H-pyrrole als stabile Zwischenstufen bei der Umwandlung von .beta.-Cycloalkenykalpha.-azidoacrylestern in Cycloalkano-1H-pyrrole", Angew. Chem. 1993, 105(7), 1116-1117.

Vogel et al., "Cycloalkano-2H-pyrrole as a Stable Intermediate in the Conversion of betaCycloalkenyl-alpha-azidoacrylates to Cycloalkano-1H pyrroles", Angew. Chem. Int. Ed. Engl. 1993, 32(7), 1051-1052. [Translation of Angew. Chem. 1993, 105(7), 1116-1117.].

Walter et al., "Synthesis and Central Nervous System Activity of 1,2,3,4-Tetrahydro- 1 -amino-4- phenyl-naphtalenes," Journal of Medicinal Chemistry, 1974, 17(4), 459-463.

Wang et al., "Synthesis of ethyl cyclopenteno- or cyclohexeno[b]pyrrolyl-2-carboxylates", Youji Huaxue 1997, 17(6), 524-528.

Watanabe et al., "Enantioselective addition of chirally modified allylboranes to N-(trimethylsilyObenzaldehyde imine", Tetrahedron Asymmetry 1995, 6(7), 1531-1534.

Welch etal., "Improved Syntheses of [3,2-b]- and [2,3-b]-fused Selenolo- and Thienopyrroles, and of Furo[3,2-b]pyrrole", Heterocycl. Comm. 1999, 5(4), 305-310.

Wen etal., "Cell differentiation enhancement by hydrophilic derivatives of 4,8-Dihydrobenzo[1,2- b:5,4-bldithiophene-4,8-diones in HL-60 leukemia cells", Bioorg. Med. Chem. Lett. 2007, 17(10), 2908-2912.

Wensbo etal., "Indole-3-Acetic Acids and Hetero Analogues by One Pot Synthesis including Heck Cyclisation", Tetrahedron 1995, 51(37), 10323-10342.

Wensbo et al., "Indole-3-pyruvic acid oxime ethers and thieno analogues by Heck cyclisation. Application to the synthesis of thiatryptophans", Tetrahedron 1996, 52(47), 14975-14988.

Wernly-Chung et al., "Structure-reactivity relationships in the chemical hydrolysis of prodrug esters of nicotinic acid", Int. J. Pharm. 1990, 63(2), 129-134.

West, A. R., "Solid State Chemistry and its Applications"; Wiley: New York, 1988; pp. 358 and 365.

Wright et al., "Derivatives of 11-(1-piperazinyl)-5H-pyrrolo[2,1-c][1,4]benzodiazepine as central nervous system agents", J. Med. Chem. 1980, 23(4), 462-465.

Xue et al., "An Efficient Synthesis of Glycoprotein llb/IIIa Inhibitor DMP728. A Novel Synthesis of N.alpha.-Methylarginine-Containing Peptide", J. Org. Chem. 1995, 60(4), 946-952.

Yardley et al., "2-Phenyl-2-(1-hydroxycycloalkyDethylamine derivatives: synthesis and antidepressant activity", J. Med. Chem. 1990, 33(10), 2899-2905.

Yarovenko et al., "Regioselective acylation of methyl 2-methy1-4H-thieno[3,2-b]pyrrole-5-carboxylate", Russ. Chem. Bull., Int. Ed., 2003, 52(2), 451-456.

Yasuhara et al., "Prodrugs of 3-(3,4-dichlorobenzyloxy)-2-amino-6-fluorobicyclo[3.1.0]hexane2,6-dicarb- oxylic acid (MGS0039): a potent and orally active group II mGluR antagonist with antidepressant-like potential", Bioorg. Med. Chem. 2006, 14(12), 4193-4207.

Yevich et al., "Synthesis and biological evaluation of 1-(1,2-benzisothiazol-3-y1)- and (1,2- benzisoxazol-3-yDpiperazine derivatives as potential antipsychotic agents", J. Med. Chem. 1986, 29(3), 359-369.

Yu et al., "The regiospecific C-4 lithiation of 2-(tert-butyldimethylsilyl)-3-furoic acid", J. Chem. Soc., Perkin Trans. 1, 1991(10), 2600-2601.

Yudina et al., "Synthesis and alkylation of indolo[3,2-b]carbazoles", Tetrahedron 2003, 59(8), 1265-1275.

Zani et al., "Biological studies on 1,2-benzisothiazole derivatives. VI. Antimicrobial activity of 1,2-benzisothiazole and 1,2-benzisothiazolin-3-one derivatives and of some corresponding 1,2-benzisoxazoles", Farmaco 1996, 51(11), 707-713.

Zaragoza Dorwald, F., "Side Reactions in Organic Synthesis"; Wiley-VCH: Weinheim, 2005; pp. IX and 41.

Zhang et al., "Synthesize the china 3-pyridyl ester analogs of anaddicted analgesic Epibatidine", Journal of Shangqiu Teachers College (Shangqiu Shifan Xueyuan Xuebao) 2004, 20(5), 90-94.

Zhang et al., "Total synthesis of the porphyrin mineral abelsonite and related petroporphyrins with five-membered exocyclic rings", Tetrahedron Lett. 2003, 44(39), 7253-7256.

Zinoune et al., "Aminoalkylation of Aldehydes with Glyoxal N,N-Dimethlmonohydrazone Yields Stable 4-Substituted Pyrrolin-3-ones", Heterocycles 1989, 28(2), 1077-1084.

Zong et al., "A new and efficient synthetic route toward 3,4-alkylenedioxypyrrole (XDOP) derivatives via Mitsunobu chemistry", Tetrahedron Lett. 2006, 47(21), 3521-3523.

PROCESS FOR PREPARATION OF TRANS 4-(3,4-DICHLOROPHENYL)-1,2,3,4-TETRAHYDRO-1NAPTHALENAMINE

CROSS REFERENCE TO RELATED APPLICATIONS

This application is a divisional of copending U.S. application Ser. No. 11/994,644, which is a National Phase filing under 35 USC §371 of PCT International Application PCT/US2006/026361, filed Jul. 6, 2006, and published under PCT Article 21(2) in English as WO 2007/006003 on Jan. 11, 2007. PCT/US2006/026361 claimed priority from U.S. Provisional Application No. 60/697,013 filed on Jul. 6, 2005. The entire contents of each of the prior applications are incorporated herein by reference.

FIELD OF THE INVENTION

The present invention relates to compositions and methods for the treatment of menopause and mood, anxiety, and cognitive disorders.

BACKGROUND OF THE INVENTION

Menopause, which is caused by a lowering of the production of female sex hormones that typically occurs at around age 50, but can occur at much earlier or later ages, can generate disorders such as edema, hot flushes (or flashes), attacks of sweating, muscle and possibly joint pain, sleep disturbances, dysphoria, nervousness, mood swings, headache, palpitations (enhanced frequency of heart rate), dry mucous membranes, pain during intercourse and urinary disturbances. Hot flashes or flushing are characterized by a sudden onset of warmth in the face and neck, often progressing to the chest. Episodes generally last several minutes and are evidenced by a visible flushing of the skin. Often such episodes are accompanied by sweating, dizziness, nausea, palpitations and diaphoresis. Such symptoms can disrupt sleep and interfere with quality of life.

Although the cause of hot flashes is not completely understood, they are thought to be a disorder of thermoregulation within the hypothalamus that is a consequence of declining estrogen levels. The administration of female sex hormones, such as estrogen, is effective in palliating these symptoms, but hormone therapy is fraught with undesirable side effects. Four out of five women have disturbing menopause disorders for at least one year and 25% of women have menopause disorders for more than 5 years. Half of all women have severe disorders. Men may also have hot flashes following androgen deprivation therapy (from bilateral orchiectomy or treatment with a gonadotrophin-releasing-hormone agonist) for metastatic prostate cancer. Menopause and perimenopause may also be associated with mood disorders such as depression and anxiety.

Clinicians recognize a distinction among central nervous system illnesses, and there have been many schemes for categorizing mental disorders. The *Diagnostic and Statistical Manual of Mental Disorders, Fourth Ed., Text Revision*, (hereinafter, the "DSM-IV-TR™"), published by the American Psychiatric Association, and incorporated herein by reference, provides a standard diagnostic system upon which persons of skill rely. According to the framework of the DSM-IV-TR™, the CNS disorders of Axis I include: disorders diagnosed in childhood (such as, for example, attention deficit disorder or "ADD" and attention deficit/hyperactivity disorder or "ADHD") and disorders diagnosed in adulthood. CNS disorders diagnosed in adulthood include (1) schizophrenia and psychotic disorders; (2) cognitive disorders; (3) mood disorders; (4) anxiety related disorders; (5) eating disorders; (6) substance related disorders; (7) personality disorders; and (8) "disorders not yet included" in the scheme.

Mood disorders are a group of heterogeneous, typically recurrent illnesses including unipolar (depressive) and bipolar (manic-depressive) disorders that are characterized by pervasive mood disturbances, psychomotor dysfunction, and vegetative symptoms.

In its full syndromal expression, clinical depression manifests as major depressive disorder, with episodic course and varying degrees of residual manifestations between episodes. The mood is typically depressed, irritable, and/or anxious. The patient may appear miserable, with furrowed brows, downturned corners of the mouth, slumped posture, poor eye contact, and monosyllabic (or absent) speech. The morbid mood may be accompanied by preoccupation with guilt, self-denigrating ideas, decreased ability to concentrate, indecisiveness, diminished interest in usual activities, social withdrawal, helplessness, hopelessness, and recurrent thoughts of death and suicide. Sleep disorders are common. In some, the morbid mood is so deep that tears dry up; the patient complains of an inability to experience usual emotions—including grief, joy, and pleasure—and of a feeling that the world has become colorless, lifeless, and dead.

Melancholia (formerly endogenous depression) is characterized by marked psychomotor slowing (of thinking and activity) or agitation (eg, restlessness, wringing of the hands, pressure of speech), weight loss, irrational guilt, and loss of the capacity to experience pleasure. Mood and activity vary diurnally, with a nadir in the morning. Most melancholic patients complain of difficulty falling asleep, multiple arousals, and insomnia in the middle of the night or early morning. Sexual desire is often diminished or lost. Amenorrhea can occur. Anorexia and weight loss may lead to emaciation and secondary disturbances in electrolyte balance.

In atypical depression, reverse vegetative features dominate the clinical presentation; they include anxious-phobic symptoms, evening worsening, initial insomnia, hypersomnia that often extends into the day, and hyperphagia with weight gain. Unlike patients with melancholia, those with atypical depression show mood brightening to potentially positive events but often crash into a paralyzing depression with the slightest adversity. Atypical depressive and bipolar II disorders overlap considerably.

In dysthymic disorder, depressive symptoms typically begin insidiously in childhood or adolescence and pursue an intermittent or low-grade course over many years or decades; major depressive episodes may complicate it (double depression). In pure dysthymia, depressive manifestations occur at a subthreshold level and overlap considerably with those of a depressive temperament: habitually gloomy, pessimistic, humorless, or incapable of fun; passive and lethargic; introverted; skeptical, hypercritical, or complaining; self-critical, self-reproaching, and self-derogatory; and preoccupied with inadequacy, failure, and negative events.

Thorough evaluation of many persons with depression reveals bipolar traits, and as many as one in five patients with a depressive disorder also develops frank hypomania or mania. Most switches from unipolar to bipolar disorder occur within 5 years of the onset of depressive manifestations. Predictors of a switch include early onset of depression (<25 years old), postpartum depression, frequent episodes of depression, quick brightening of mood with somatic treatments (eg, antidepressants, phototherapy, sleep deprivation, electroconvulsive therapy), and a family history of mood disorders for three consecutive generations.

Between episodes, patients with bipolar disorder exhibit depressive moodiness and sometimes high-energy activity; disruption in developmental and social functioning is more common than in unipolar disorder. In bipolar disorder, episodes are shorter (3 to 6 months), age of onset is younger, onset of episodes is more abrupt, and cycles (time from onset of one episode to that of the next) are shorter than in unipolar disorder. Cyclicity is particularly accentuated in rapid-cycling forms of bipolar disorder (usually defined as >=4 episodes/year).

In bipolar I disorder, full-fledged manic and major depressive episodes alternate. Bipolar I disorder commonly begins with depression and is characterized by at least one manic or excited period during its course. The depressive phase can be an immediate prelude or aftermath of mania, or depression and mania can be separated by months or years.

In bipolar II disorder, depressive episodes alternate with hypomanias (relatively mild, nonpsychotic periods of usually <1 week). During the hypomanic period, mood brightens, the need for sleep decreases, and psychomotor activity accelerates beyond the patient's usual level. Often, the switch is induced by circadian factors (eg, going to bed depressed and waking early in the morning in a hypomanic state). Hypersomnia and overeating are characteristic and may recur seasonally (eg, in autumn or winter); insomnia and poor appetite occur during the depressive phase. For some persons, hypomanic periods are adaptive because they are associated with high energy, confidence, and supernormal social functioning. Many patients who experience pleasant elevation of mood, usually at the end of a depression, do not report it unless specifically questioned.

Patients with major depressive episodes and a family history of bipolar disorders (unofficially called bipolar III) often exhibit subtle hypomanic tendencies; their temperament is termed hyperthymic (ie, driven, ambitious, and achievement-oriented).

In cyclothymic disorder, less severe hypomanic and mini-depressive periods follow an irregular course, with each period lasting a few days. Cyclothymic disorder is commonly a precursor of bipolar II disorder. But it can also occur as extreme moodiness without being complicated by major mood disorders. In such cases, brief cycles of retarded depression accompanied by low self-confidence and increased sleep alternate with elation or increased enthusiasm and shortened sleep. In another form, low-grade depressive features predominate; the bipolar tendency is shown primarily by how easily elation or irritability is induced by antidepressants. In chronic hypomania, a form rarely seen clinically, elated periods predominate, with habitual reduction of sleep to <6 hours. Persons with this form are constantly overcheerful, self-assured, overenergetic, full of plans, improvident, overinvolved, and meddlesome; they rush off with restless impulses and accost people.

Anxiety disorders are more common than any other class of psychiatric disorder. Panic attacks are common, affecting >⅓ of the population in a single year. Most persons recover without treatment; a few develop panic disorder. Panic disorder is uncommon, affecting <1% of the population in a 6-month period. Panic disorder usually begins in late adolescence or early adulthood and affects women two to three times more often than men. Phobic disorders involve persistent, unrealistic, yet intense anxiety that, unlike the free-floating anxiety of panic disorder, is attached to external situations or stimuli. Persons who have a phobia avoid such situations or stimuli or endure them only with great distress. However, they retain insight and recognize the excessiveness of their anxiety. In agoraphobia, anxiety about or avoidance of being trapped in situations or places with no way to escape easily if panic develops. Agoraphobia is more common than panic disorder. It affects 3.8% of women and 1.8% of men during any 6-month period. Peak age of onset is the early 20s; first appearance after age 40 is unusual. In specific phobias, clinically significant anxiety is induced by exposure to a specific situation or object, often resulting in avoidance. Specific phobias are the most common anxiety disorders but are often less troubling than other anxiety disorders. They affect 7% of women and 4.3% of men during any 6-month period.

One form of anxiety disorder is social phobia, which is a clinically significant anxiety induced by exposure to certain social or performance situations, often resulting in avoidance. Social phobias affect 1.7% of women and 1.3% of men during any 6-month period. However, more recent epidemiologic studies suggest a substantially higher lifetime prevalence of about 13%. Men are more likely than women to have the most severe form of social anxiety, avoidant personality disorder.

Yet another anxiety disorder is Obsessive-Compulsive Disorder (OCD), a disorder characterized by recurrent, unwanted, intrusive ideas, images, or impulses that seem silly, weird, nasty, or horrible (obsessions) and by urges to do something that will lessen the discomfort due to the obsessions (compulsions). Obsessive-compulsive disorder occurs about equally in men and women and affects 1.6% of the population during any 6-month period.

Posttraumatic Stress Disorder is another anxiety disorder. It is a disorder in which an overwhelming traumatic event is reexperienced, causing intense fear, helplessness, horror, and avoidance of stimuli associated with the trauma. The stressful event involves serious injury or threatened death to the person or others or actual death of others; during the event, the person experiences intense fear, helplessness, or horror. Lifetime prevalence is at least 1%, and in high-risk populations, such as combat veterans or victims of criminal violence, prevalence is reported to be between 3% and 58%.

Acute stress disorder resembles posttraumatic stress disorder in that the person has been traumatized, reexperiences the trauma, avoids stimuli that remind him of the trauma, and has increased arousal. However, by definition, acute stress disorder begins within 4 weeks of the traumatic event and lasts a minimum of 2 days but no more than 4 weeks. A person with this disorder has three or more of the following dissociative symptoms: a sense of numbing, detachment, or absence of emotional responsiveness; reduced awareness of surroundings (eg, being dazed); a feeling that things are not real; a feeling that he is not real; and amnesia for an important part of the trauma. The prevalence of acute stress disorder is unknown but is presumably proportionate to the severity of the trauma and the extent of exposure to the trauma.

Generalized Anxiety Disorder is an excessive, almost daily, anxiety and worry for ≧6 months about a number of activities or events. Generalized anxiety disorder is common, affecting 3 to 5% of the population within a 1-year period. Women are twice as likely to be affected as men. The disorder often begins in childhood or adolescence but may begin at any age.

Anxiety may be secondary to physical disorders, such as neurologic disorders (eg, brain trauma, infections, inner ear disorders), cardiovascular disorders (eg, heart failure, arrhythmias), endocrine disorders (eg, overactive adrenal or thyroid glands), and respiratory disorders (eg, asthma, chronic obstructive pulmonary disease). Anxiety may be caused by use of drugs, such as alcohol, stimulants, caffeine, cocaine, and many prescription drugs. Also, drug withdrawal is commonly associated with anxiety.

An estimated 4 to 5 million Americans (about 2% of all ages and 15% of those >age 65) have some form and degree of cognitive failure (cognitive disorder). Cognitive failure (dysfunction or loss of cognitive functions—the processes by which knowledge is acquired, retained, and used) is most commonly due to delirium (sometimes called acute confusional state) or dementia. It may also occur in association with disorders of affect, such as depression.

Delirium (Acute Confusional State) is a clinical state characterized by fluctuating disturbances in cognition, mood, attention, arousal, and self-awareness, which arises acutely, either without prior intellectual impairment or superimposed on chronic intellectual impairment. Some practitioners use the terms delirium and acute confusional state synonymously; others use delirium to refer to a subset of confused people with hyperactivity. Still others use delirium to refer to full-blown confusion and confusional state to refer to mild disorientation.

Dementia is a chronic deterioration of intellectual function and other cognitive skills severe enough to interfere with the ability to perform activities of daily living. Dementia may occur at any age and can affect young people as the result of injury or hypoxia. However, it is mostly a disease of the elderly, affecting >15% of persons >65 years old and as many as 40% of persons >80 years old. It accounts for more than half of nursing home admissions and is the condition most feared by aging adults.

Alzheimer's Disease is a progressive, inexorable loss of cognitive function associated with an excessive number of senile plaques in the cerebral cortex and subcortical gray matter, which also contains β-amyloid and neurofibrillary tangles consisting of tau protein.

Lewy body dementia may be the second most common dementia after Alzheimer's disease. Lewy bodies are hallmark lesions of degenerating neurons in Parkinson's disease and occur in dementia with or without features of Parkinson's disease. In Lewy body dementia, Lewy bodies may predominate markedly or be intermixed with classic pathologic changes of Alzheimer's disease. Symptoms, signs, and course of Lewy body dementia resemble those of Alzheimer's disease, except hallucinations (mainly visual) are more common and patients appear to have an exquisite sensitivity to antipsychotic-induced extrapyramidal adverse effects.

Cerebrovascular disease can destroy enough brain tissue to impair function. Vascular dementia, which includes impairment due to single, strategically located infarcts or to multiple small infarcts from small or medium-sized vessel disease, is more common in men and generally begins after age 70. It occurs more often in persons who have hypertension and/or diabetes mellitus or who abuse tobacco. Progressive vascular dementia can generally be slowed by controlling blood pressure, regulating blood sugar (90 to 150 mg/dL), and stopping smoking. Some degree of vascular damage is found in up to 20% of autopsies of patients with dementia.

Binswanger's dementia (subcortical arteriosclerotic encephalopathy) is uncommon and involves multiple infarcts in deep hemispheric white matter associated with severe hypertension and systemic vascular disease. Although clinically similar to vascular dementia, Binswanger's dementia may be characterized by more focal neurologic symptoms associated with acute strokes and a more rapid course of deterioration. MRI and CT show areas of leukoencephalopathy in the cerebrum semiovale adjacent to the cortex.

More than 25% of patients with Parkinson's disease have dementia; some estimates are as high as 80% (see Ch. 179). At autopsy, patients with Parkinson's disease may have some of the neuropathologic brain findings and many of the biochemical changes seen in patients with Alzheimer's disease. A less severe subcortical dementia is also associated with Parkinson's disease.

The dementia associated with progressive supranuclear palsy is commonly preceded by other neurologic symptoms, eg, multiple falls, dystonic axial rigidity, retrocollis, supranuclear ophthalmoplegia, dysphagia, and dysarthria.

Patients with Huntington's disease (chorea) may also present with symptoms of dementia, but the diagnosis is usually clarified by the family history, younger age at onset, and the disease's characteristic motor abnormalities. In case of doubt, genetic analysis can be diagnostic.

Pick's disease is a less common form of dementia, affecting the frontal and temporal regions of the cortex. Patients have prominent apathy and memory disturbances; they may show increased carelessness, poor personal hygiene, and decreased attention span. Although the clinical presentation and CT findings in Pick's disease can be quite distinctive, definitive diagnosis is possible only at autopsy. The Klüver-Bucy syndrome can occur early in the course of Pick's disease, with emotional blunting, hypersexual activity, hyperorality (bulimia and sucking and smacking of lips), and visual agnosias.

Frontal lobe dementia syndromes may result from intrinsic pathology, a primary or metastatic tumor, previous surgical manipulation, irradiation to the brain, or severe head trauma. The repeated head trauma in dementia pugilistica, which occurs in professional fighters, appears to link genetically to the 4 allele of apo E.

Normal-pressure hydrocephalus is characterized by a triad of progressive dementia, incontinence, and an unsteady, slow, and wide-based gait. Onset is usually insidious and occurs mostly in late middle or old age. The disease is more common in men and occasionally is related to prior meningitis, subarachnoid hemorrhage, head injury, or neurosurgical interventions. In most cases, evidence of precedent injury is lacking. Normal-pressure hydrocephalus may result from scarring of arachnoid villi over convexities of the brain, which results in slowed absorption of CSF (ceresbrospinal fluid), ventricular dilatation, and frontal lobe motor abnormalities. The laboratory diagnosis is based on high-normal CSF pressure (150 to 200 mm Hg) and CT evidence of ventricular dilatation and narrowed cerebral sulci at the brain's apex without widening of the subarachnoid space. The results of treatment with CSF shunting are inconsistent. The dementia is sometimes reversible; some experts recommend a therapeutic lumbar puncture to remove about 30 mL of CSF. Improvement in gait and cognition for hours or several days suggests the value of shunt placement.

Subdural hematoma can cause a change in mental status, producing coma, delirium, or a dementia syndrome. Cognitive changes may begin any time after blood begins to accumulate and can progress rapidly or slowly, according to the size and location of the hematoma. This chronic syndrome may resemble vascular dementia, with focal neurologic signs and cognitive changes. Removing the hematoma may restore function or prevent further loss of intellectual function. However, some experts believe that after hematomas have exerted pressure on the brain for a long time (perhaps a year or more), removing them does little to improve cognitive function.

The most well-known infectious cause of dementia is Creutzfeldt-Jakob disease, in which memory deficits, electroencephalographic changes, myoclonus, and sometimes ataxia are prominent. The infectious agent is a corrupted protein called a prion that can be acquired genetically, by tissue transplantation, by cannibalism, and apparently by eating products from infected cattle (with mad-cow disease).

Most cases occur sporadically. It produces a characteristic spongiform encephalopathy quite different from the changes of Alzheimer's disease. The course is more rapid than that of Alzheimer's disease and usually lasts from 6 to 12 months.

Patients with Gerstmann-Sträussler-Scheinker disease, another dementia with a prion-related cause, typically present with ataxia, followed later by cognitive decline. This syndrome affects younger persons and has a longer duration than Creutzfeldt-Jakob disease.

General paresis, a form of neurosyphilis, was once a common cause of dementia in Western societies. It is still prevalent in developing countries. In addition to intellectual decline, tremors and pupillary changes can occur. The CSF is tested using the fluorescent treponemal antibody (FTA) test. A positive FTA test for syphilis establishes the diagnosis.

AIDS dementia can complicate the later stages of HIV infection. Dementia may be caused by HIV, by the JC virus that causes progressive multifocal leukoencephalopathy, or by a variety of other opportunistic infectious agents, including fungi, bacteria, viruses, or protozoa that can be identified at autopsy. Early manifestations include slowed thinking and expression, difficulty in concentration, and apathy, with preserved insight and few manifestations of depression. Motor movements are slowed; ataxia and weakness may be evident. Reflexes, including the extensor plantar responses, become abnormal. Treatment with zidovudine often induces improvement sometimes verging on the dramatic.

Therefore, there exists a need to develop effective and minimally adverse therapies for the above listed disorders.

SUMMARY OF THE INVENTION

The present invention generally relates to pharmaceutical compositions comprising eszopiclone or a pharmaceutically acceptable salt, solvate, clathrate, polymorph, or co-crystal thereof, and trans 4-(3,4-dichlorophenyl)-1,2,3,4-tetrahydro-N-methyl-1-napthalenamine or trans 4-(3,4-dichlorophenyl)-1,2,3,4-tetrahydro-1-napthalenamine. The pharmaceutical compositions of the invention are useful in the treatment of menopause, perimenopause, mood disorders, anxiety disorders, and cognitive disorders.

In addition, the present invention relates to a method for augmentation of antidepressant therapy in a patient comprising administering to the patient a therapeutically effective amount of eszopiclone, or a pharmaceutically acceptable salt, solvate, clathrate, polymorph, or co-crystal thereof. The present invention also relates to a method for eliciting a dose-sparing effect in a patient undergoing treatment with trans 4-(3,4-dichlorophenyl)-1,2,3,4-tetrahydro-N-methyl-1-napthalenamine or trans 4-(3,4-dichlorophenyl)-1,2,3,4-tetrahydro-1-napthalenamine comprising administering to the patient a therapeutically effective amount of eszopiclone, or a pharmaceutically acceptable salt, solvate, clathrate, polymorph, or co-crystal thereof.

Furthermore, the present invention relates to a method for reducing depression relapse in a patient who received trans 4-(3,4-dichlorophenyl)-1,2,3,4-tetrahydro-N-methyl-1-napthalenamine or trans 4-(3,4-dichlorophenyl)-1,2,3,4-tetrahydro-1-napthalenamine treatment comprising administering to the patient a therapeutically effective amount eszopiclone, or a pharmaceutically acceptable salt, solvate, clathrate, polymorph, or co-crystal thereof.

Co-administration of eszopiclone, a sedative agent, together with an trans 4-(3,4-dichlorophenyl)-1,2,3,4-tetrahydro-N-methyl-1-napthalenamine or trans 4-(3,4-dichlorophenyl)-1,2,3,4-tetrahydro-1-napthalenamine is beneficial in treatment of such disorders as menopause, perimenopause, mood disorders, anxiety disorders, and cognitive disorders.

DETAILED DESCRIPTION OF THE INVENTION

The present invention relates generally to pharmaceutical compositions containing two or more active agents that when taken together have benefit in treatment of menopause, perimenopause, mood disorder, anxiety disorder, or cognitive disorder. In certain embodiments, the present invention relates to a pharmaceutical composition comprising eszopiclone and trans 4-(3,4-dichlorophenyl)-1,2,3,4-tetrahydro-N-methyl-1-napthalenamine or trans 4-(3,4-dichlorophenyl)-1,2,3,4-tetrahydro-1-napthalenamine. In one embodiment, eszopiclone of the above listed embodiments is present as a pharmaceutically acceptable salt, solvate, clathrate, polymorph, or co-crystal thereof. In another embodiment, trans 4-(3,4-dichlorophenyl)-1,2,3,4-tetrahydro-N-methyl-1-napthalenamine or trans 4-(3,4-dichlorophenyl)-1,2,3,4-tetrahydro-1-napthalenamine is present as a pharmaceutically acceptable salt, solvate, clathrate, polymorph, or co-crystal thereof.

Another aspect of the present invention relates to a method of treating a patient suffering from menopause, perimenopause, mood disorder, anxiety disorder, or cognitive disorder comprising the step of administering to said patient a therapeutically effective dose of a pharmaceutical composition containing two or more active agents that when taken together improve the quality of sleep or sleep disorders for said patient.

Further aspect of the present invention relates to a method of treating a patient suffering from menopause, perimenopause, mood disorder, anxiety disorder, or cognitive disorder comprising the step of administering to said patient a therapeutically effective dose of a pharmaceutical composition containing two or more active agents that when taken together improve the treatment of the patient.

In another embodiment, the present invention relates to a method for augmentation of trans 4-(3,4-dichlorophenyl)-1,2,3,4-tetrahydro-N-methyl-1-napthalenamine or trans 4-(3,4-dichlorophenyl)-1,2,3,4-tetrahydro-1-napthalenamine therapy in a patient comprising administering to the patient a therapeutically effective amount of eszopiclone, or a pharmaceutically acceptable salt, solvate, clathrate, polymorph, or co-crystal thereof.

The present invention also relates to a method for eliciting a dose-sparing effect in a patient undergoing treatment with trans 4-(3,4-dichlorophenyl)-1,2,3,4-tetrahydro-N-methyl-1-napthalenamine or trans 4-(3,4-dichlorophenyl)-1,2,3,4-tetrahydro-1-napthalenamine comprising administering to the patient a therapeutically effective amount of eszopiclone, or a pharmaceutically acceptable salt, solvate, clathrate, polymorph, or co-crystal thereof.

Furthermore, the present invention relates to a method for reducing depression relapse in a patient who received trans 4-(3,4-dichlorophenyl)-1,2,3,4-tetrahydro-N-methyl-1-napthalenamine or trans 4-(3,4-dichlorophenyl)-1,2,3,4-tetrahydro-1-napthalenamine treatment comprising administering to the patient a therapeutically effective amount of eszopiclone, or a pharmaceutically acceptable salt, solvate, clathrate, polymorph, or co-crystal thereof.

Eszopiclone

Eszopiclone is a cyclopyrrolone that has the chemical name (+) 6-(5-chloropyrid-2-yl)-5-(4-methylpiperazin-1-yl) carbonyloxy-7-oxo-6,7-dihydro-5H-pyrrolo[3-4-b]pyrazine or (+) 6-(5-chloro-2-pyridinyl)-6,7-dihydro-7-oxo-5H-pyrrolo[3,4-b]pyrazin-5-yl-4-methylpiperazine-1-carboxylate. The chemical structure of eszopiclone is shown below:

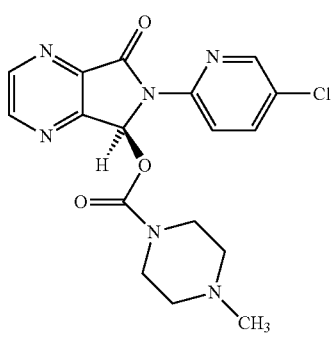

Eszopiclone is the S-(+)-optical isomer of the compound zopiclone, which is described in U.S. Pat. Nos. 6,319,926 and 6,444,673. Racemic zopiclone is described in Goa and Heel, [Drugs, 32:48-65 (1986)] and in U.S. Pat. Nos. 3,862,149 and 4,220,646. S-(+)-zopiclone, which will hereinafter be referred to by its USAN-approved generic name, eszopiclone, includes the optically pure and the substantially optically pure (e.g., 90%, 95% or 99% optical purity) S-(+)-zopiclone isomer.

Zopiclone was the first of a chemically distinct class of hypnotic and anxiolytic compounds that offers a psychotherapeutic profile of efficacy and side effects similar to the benzodiazepines. Some members of this class of compounds, the cyclopyrrolones, appear to cause less residual sedation and less slowing of reaction times than the benzodiazepines, and it offers the promise of an improved therapeutic index over benzodiazepines. Recently, the USFDA approved use of eszopiclone (LUNESTA™) for the treatment of insomnia.

Eszopiclone possesses potent activity in treating sleep disorders such as insomnia. Eszopiclone also possess potent activity in treating sleep disorders while avoiding the usual adverse effects including but not limited to drowsiness, next day effects tiredness in the morning, inability to concentrate and headache. U.S. Pat. No. 5,786,357 relates to methods of using eszopiclone also to treat convulsive disorders such as epilepsy.

The size of a prophylactic or therapeutic dose of eszopiclone in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.25 mg to about 10 mg. Preferably, a daily dose range should be between about 0.5 mg to about 5 mg. Most preferably, a daily dose range should be between about 0.5 mg to about 3.0 mg. In one embodiment, the daily dose is 0.5 mg, 1.0 mg, 1.5 mg, 2.0 mg, 2.5 mg, or 3.0 mg. In managing the patient, the therapy may be initiated at a lower dose, perhaps about 0.5 mg to about 2 mg and increased depending-on the patient's global response. It is further recommended that children and patients over 65 years, and those with impaired renal or hepatic function, initially receive low doses, and that they be titrated based on global response and blood level. It may be necessary to use dosages outside these ranges in some cases.

In the case where an oral composition is employed, a suitable dosage range for use is from about 0.25 mg to about 10.0 mg with, in the usual case, the lower doses serving more common insomnia, and the higher doses, presented in divided dosing, reserved for control of psychiatric disorders. Preferably, a dose range of between about 0.5 mg to about 5 mg is given as a once daily administration or in divided doses if required; most preferably, a dose range of from about 0.5 mg to about 3 mg is given, either as a once daily administration or in divided doses if required. Patients may be upward titrated from below to within this dose range to a satisfactory control of symptoms as appropriate.

trans 4-(3,4-dichlorophenyl)-1,2,3,4-tetrahydro-N-methyl-1-napthalenamine

Sertraline, whose chemical name is (1S,4S)-cis 4-(3,4-dichlorophenyl)-1,2,3,4-tetrahydro-N-methyl-1-napthalenamine, is approved for the treatment of depression by the United States Food and Drug Administration, and is available under the trade name ZOLOFT® (Pfizer Inc., NY, N.Y., USA). The use of sertraline, (1R,4S)-trans 4-(3,4-dichlorophenyl)-1,2,3,4-tetrahydro-N-methyl-1-napthalenamine and (1S,4R)-trans 4-(3,4-dichlorophenyl)-1,2,3,4-tetrahydro-N-methyl-1-napthalenamine for the treatment of psychoses, psoriasis, rheumatoid arthritis and inflammation are disclosed in U.S. Pat. No. 4,981,870. The receptor pharmacology of the individual (1S,4R) and (1R,4S) enantiomers of trans 4-(3,4-dichlorophenyl)-1,2,3,4-tetrahydro-N-methyl-1-napthalenamine, is described by Welch et al., J. Med. Chem., 27:1508-1515 (1984).

The present invention utilizes (1R,4S)-trans 4-(3,4-dichlorophenyl)-1,2,3,4-tetrahydro-N-methyl-1-napthalenamine (A); and (1S,4R)-trans 4-(3,4-dichlorophenyl)-1,2,3,4-tetrahydro-N-methyl-1-napthalenamine (B):

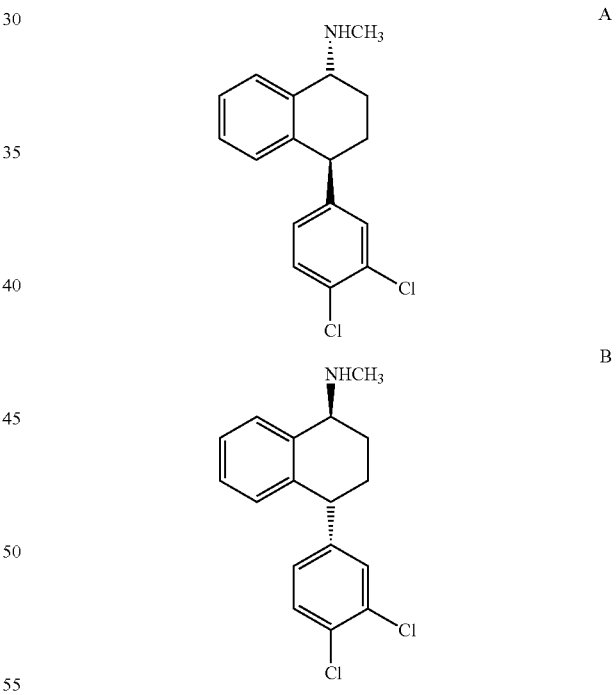

Compounds A or B are useful in treatment of menopause, perimenopause, and mood, anxiety, and cognitive disorders. The magnitude of a prophylactic or therapeutic dose of A or B will vary with the nature and severity of the condition to be treated and the route of administration. The dose, and perhaps the dose frequency, will also vary according to the age, body weight and response of the individual patient. In general, the total daily dose ranges of A and B are from about 25 mg per day to about 1000 mg per day, preferably about 100 mg per day to about 600 mg per day, in single or divided doses.

Preparation of the compounds A and B is illustrated below in Scheme 1 and its accompanying narrative.

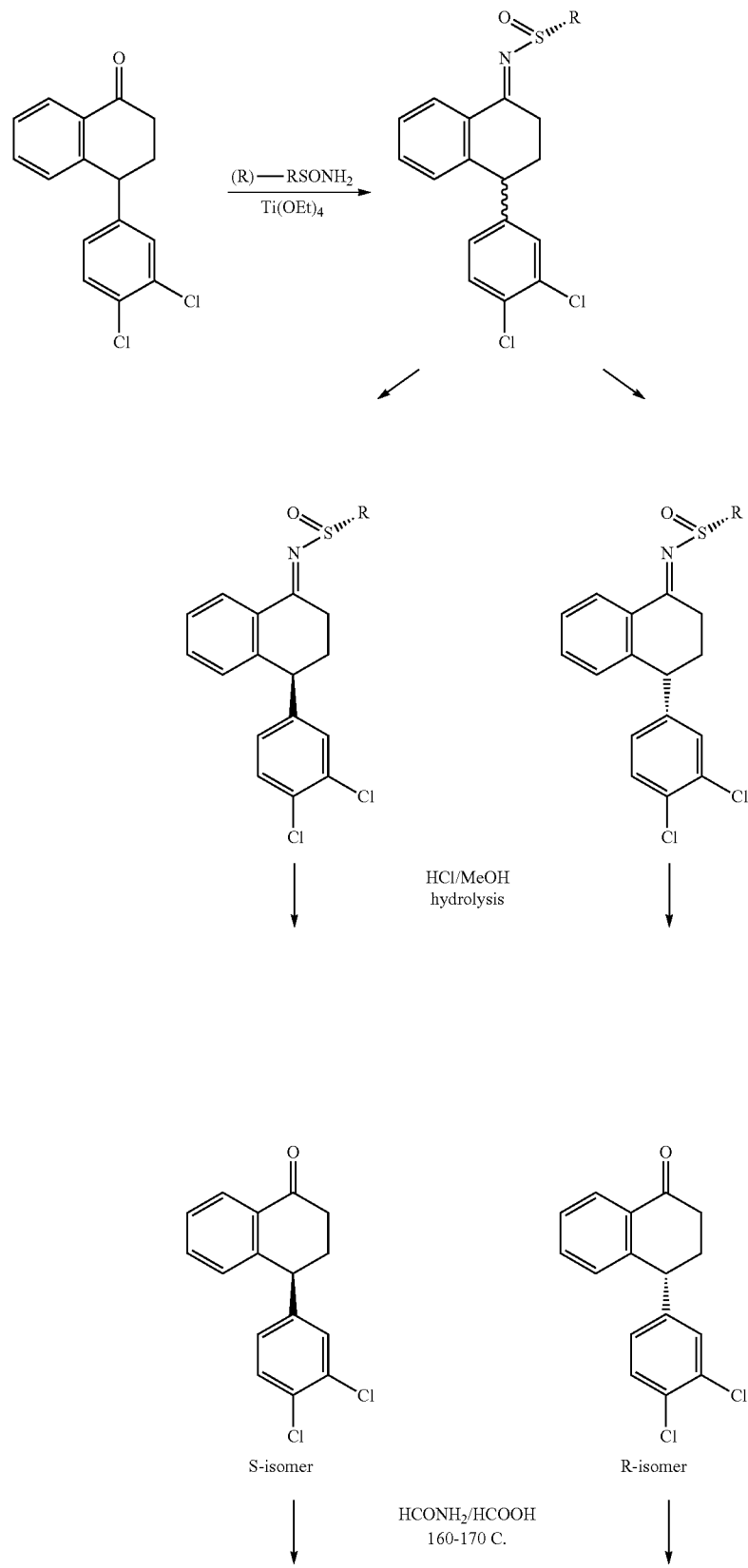

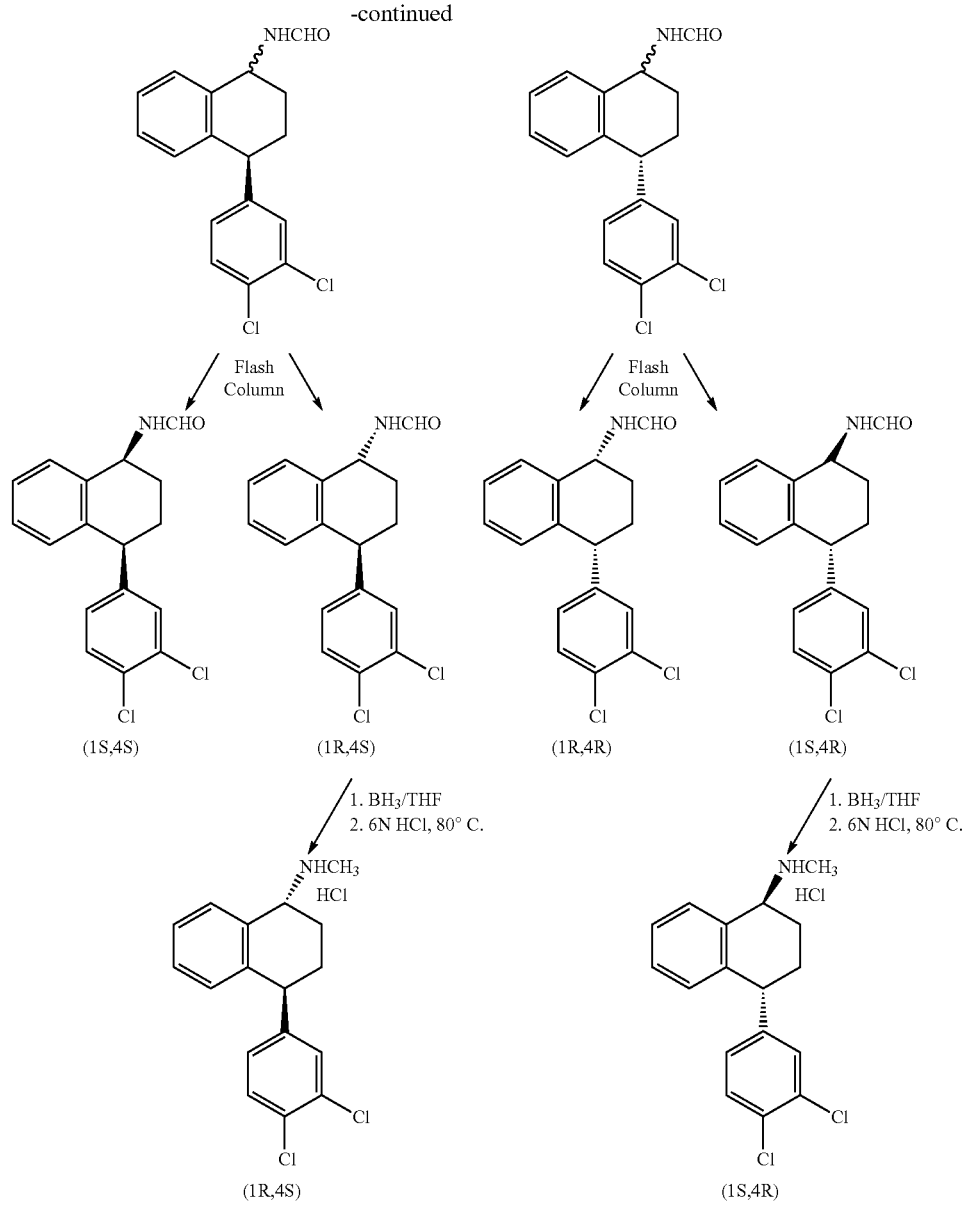

In the compound of Scheme 1, R is

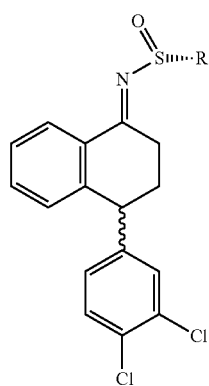

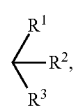

wherein $R^1$, $R^2$ and $R^3$ are each independently alkyl. In a preferred embodiment of the compounds, R is t-butyl.

Synthesis of 2-methyl-propane-2-sulfinic acid [4-(3,4-dichloro phenyl)-1,2,3,4-tetrahydro-naphthalen-y-yl]-amide (Tetralone t-butanesulfinimine): To a solution of 4((3,4-dicholorophenyl)-3,4-dihydro-1-naphthalenone (12 g) in THF (40 mL) was added (R)-t-butanesulfinamide (5.2 g) and Ti(OEt)$_4$ (85 mL 20%) in EtOH. The reaction mixture was heated to 60° C. for 13 h. The reaction mixture was cooled to rt, and poured to a brine solution (100 mL) with stirring. The suspension was then added EtOAc (300 mL) and stirred to 10 min. The suspension was filtered and the filtrate was concentrated to ca 50 mL. It was then added EtOAc (100 mL), the organic phase was then separated and concentrated to give a crude reaction mixture. The final products were isolated from the crude products by careful flash column using EtOAc and hexane (3:7 to 1:1) to give ca 3 g starting ketone, and (1R, 4S)-4-(3,4-dichlorophenyl)-3,4-dihydro-1-naphthalenone tert-butanesulfinimine (2.5 g, first product) as an oil that solidified on standing. $^1$H NMR (CDCl$_3$) δ 1.33 (S, 9H), 2.10-2.20 (m, 1H), 2.28-2.38 (m, 1H) 2.88-2.98 (m, 1H), 3.34-3.44 (m 1H), 4.12-4.24 (m, 1H), 6.84-6.88 (m, 2H), 7.20 (s, 1H), 7.25-7.40 (m, 3H), 8.22-8.28 (m, 1H).

The other product (1R,4R)-4-(3,4-dichloro phenyl)-3-4-dihydro-1-naphthalenone t-butanesulfinimine (3.0 g, second product, lower R$_f$) was isolated also as oil that solidified on standing. $^1$H NMR (CDCl$_3$) δ 1.34 (S, 9H), 2.05-2.18 (m, 1H), 2.28-2.38 (m, 1H), 3.15-3.25 (m, 2H), 4.16-4.22 (m, 1H), 6.84-6.88 (m, 2H), 7.20 (s, 1H), 7.25-7.40 (m, 3H), 8.22-8.28 (m, 1H).

Synthesis of (R)-4-(3,4-dichlorophenyl)-3,4-dihydro-1-naphthalenone: (1R,4R)-4-(3,4-dichlorophenyl)3,4-dihydro-1-naphthalenone t-butanesulfinimine (3.0 g, second product) was dissolved in MeOH (20 mL) and concentrated HCl (4 mL) at rt. The reaction mixture was stirred at rt to give a suspension. It was filtered and the solids were washed with hexane to give 1.2 g product. The enantiomeric purity was determined to be >99.3% by HPLC analysis with a ChiralPak AS10:m, 4.6×250 mm, Hexane/IPA (90:10), UV 220 nm, R-isomer 8.23 min. S-isomer 12.25 min. $^1$H NMR (CDCl$_3$) δ 2.20-2.32 (m, 1H), 2.42-2.53 (m, 1H) 2.57-2.78 (m, 2H), 4.28 (dd=4.6, 8.1 Hz, 1H), 6.95 (dd, J=2.1, 7.6 Hz, 2H), 7.23 (d J=2.0 Hz, 1H), 7.37-50 (m, 3H), 8.13 (d, J=7.6 Hz, 1H). [α]=−66° (c=1, acetone).

Synthesis of (S)-4-(3,4-dichlorophenyl)-3,4-dihydro-1-naphthalenone The previous procedure was used, starting from (1R,4S)-4-(3,4-dichlorophenyl)-3,4-dihydro-1-naphthalenone t-butanesulfinimine. 1.7 g of product (>99% ee) was obtained. [α]=+62, c=1, acetone). $^1$H NMR spectrum of the product is the same as that of its enantiomer.

Synthesis of (1S,4R) and (1R,4R)—N-[4-(3,4-dichlorophenyl)-1,2,3,4-tetrahydro-naphthalen-1-yl]-formamide: (R)-4-(3,4-dichlorophenyl)-3,4-dihydro-1-naphthalenone (1.2 g) was added formic acid (3 mL) and formamide (3 mL). The reaction mixture was heated to 160-165° C. for 15 h under nitrogen atmosphere. The reaction mixture was cooled to rt and decanted the solvent. The residue solids was passed through flash column using EtOAc:Hexane (3:7 to 1:1) to give and (1R,4R)—Norsertralaine formamide (400 mg, first spot), and (1S,4R)—Norsertraline formamide (360 mg). $^1$H NMR of the first product [(1R,4R)-isomer]: (CDCl$_3$) δ 1.80-2.10 (m, 3H), 2.10-2.20 (m, 1H), 4.00-4.10 (m, 1H), 5.22-5.30 (m, 1H), 6.10-6.20 (m, 1H), 6.80-6.90 (M, 1H), 6.90-6.96 (m, 1H), 7.10-7.40 (m, 5H), 8.22 (s, 1H). M+320. $^1$H NMR of the second product [(1S,4R)-isomer: δ 1.64-1.90 (m, 2H), 2.10-2.28 (m, 1H), 4.10 (m, 1H), 5.38-5.42 (m, 1H), 5.82-6.05 (m, 1H), 6.80-6.90 (m, 2H), 7.10-40 (m, 5H), 8.28 (s, 1H). Mass Spec. M$^+$320.

The products were reduced to the corresponding A and B by borane.

Synthesis of (1S*,4R*)-trans 4-(3,4-dichlorophenyl)-1,2, 3,4-tetrahydro-N-methyl-1-napthalenamine HCl (racemic mixture of A and B HCl): (1S*,4R*) formamide (1.0 g) was dissolved in THF (7 mL), and added BH$_3$ THF (1M, 9.3 mL, 3 eq. The reaction mixture was heated to 75-80° C. for 3 h and stirred at rt overnight. The reaction mixture was quenched with MeOH (20 mL). The mixture was concentrated to give a residue, which was dissolved in 10% HCl (20 mL). The solution was heated to 80-90° C. for 9 h, and basified with potassium carbonate, and extracted with EtOAc (25 mL). The organic phase was separated and washed with water, brine, dried over Na$_2$SO$_4$. Concentrated to give the free base. It was converted to its HCl salt in TBME with HCl/Et20 to give the product (0.75 g). $^1$H MNR(CD$_3$OD) δ 1.86-1.96 (m, 1H), 2.04-2.12 (m, 1H), 2.18-2.28 (m, 1H), 2.30-2.42 (m, 1H), 2.78 (s, 3H), 4.34 (m, 1H), 4.60 (m, 1H), 6.93-7.00 (m, 2H), 7.15 (s, 1H), 7.34-7.44 (m, 3H), 7.57-7.59 (d, J=7.2 Hz, 1H). Mass Spec. M$^+$305.

Synthesis of (1S4R)-trans 4-(3,4-dichlorophenyl)-1,2,3,4-tetrahydro-N-methyl-1-napthalenamine HCl by Resolution with (S)-Mandelic Acid: Racemic trans-sertraline (3 g) was dissolved in anhydrous ethanol (30 g) and added (S)-mandelic acid (1.5 g). The reaction mixture was heated to reflux for 30 min. and cooled to rt. The reaction solution was concentrated to give oil (ca 3 mL ethanol left). To it was added EtOAc (30 mL) and stirred for 1 h at rt. The solid formed from the solution was collected by filtration and dried (1.73 g). The solid was dissolved in hot EtOAc (35 mL), and cooled to rt in 30 min, and stirred for 1 h. The solid was collected by filtration and dried to give (1S,4R)-sertraline-(S)-mandelate (1.3 g). Ee of the product was >99% by HPLC. The solid (1.1 g) was converted to its free base with potassium carbonate, and treated with HCl/ether in MeOH to give the HCl salt (0.73 g). $^1$H NMR spectrum was identical to its racemate. (1R,4S)-sertraline HCl was prepared from the mother liquor, after enriched with (R)-mandelic acid. Mass Spec M$^+$ 305.

The commercial form of sertraline [(S,S)-cis] and its isomeric analogues were tested for their inhibition of functional uptake of serotonin (5-HT), norepinephrine (NE), or dopamine (DA), in synaptosomes prepared from rat whole brain, hypothalamus, or corpus striatum, respectively. Compounds were tested initially at 10 μM in duplicate, and if ≧50% inhibition of uptake was observed, they were tested further at 10 different concentrations in duplicate in order to obtain full inhibition curves. IC$_{50}$ values (concentration inhibiting control activity by 50%) was then determined by nonlinear regression analysis of the inhibition curves and tabulated below in the Examples sections.

trans 4-(3,4-dichlorophenyl)-1,2,3,4-tetrahydro-1-napthalenamine (1R,4S)-trans 4-(3,4-dichlorophenyl)-1,2,3,4-tetrahydro-1-napthalenamine (P) and (1S,4R)-trans 4-(3,4-dichlorophenyl)-1,2,3,4-tetrahydro-1-napthalenamine (Q) are useful in the treatment of menopause, perimenopause, and mood, anxiety, and cognitive disorders. The magnitude of a prophylactic or therapeutic dose of P or Q will vary with the nature and severity of the condition to be treated and the route of administration. The dose, and perhaps the dose frequency, will also vary according to the age, body weight and response of the individual patient. In general, the total daily dose ranges of compounds P or Q will be from about 25 mg per day to about 1000 mg per day, preferably about 100 mg per day to about 600 mg per day, in single or divided doses.

Compounds P and Q are represented by the formulae:
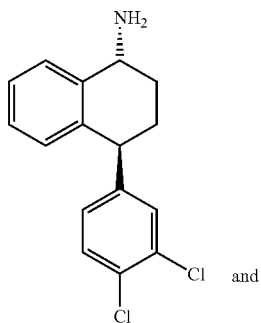
P
and
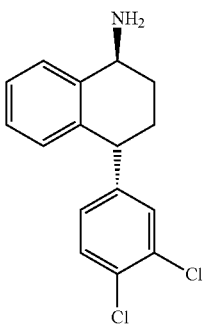
Q
Preparation of compounds P and Q is illustrated below in Scheme 2 and its accompanying narrative.
Scheme 2
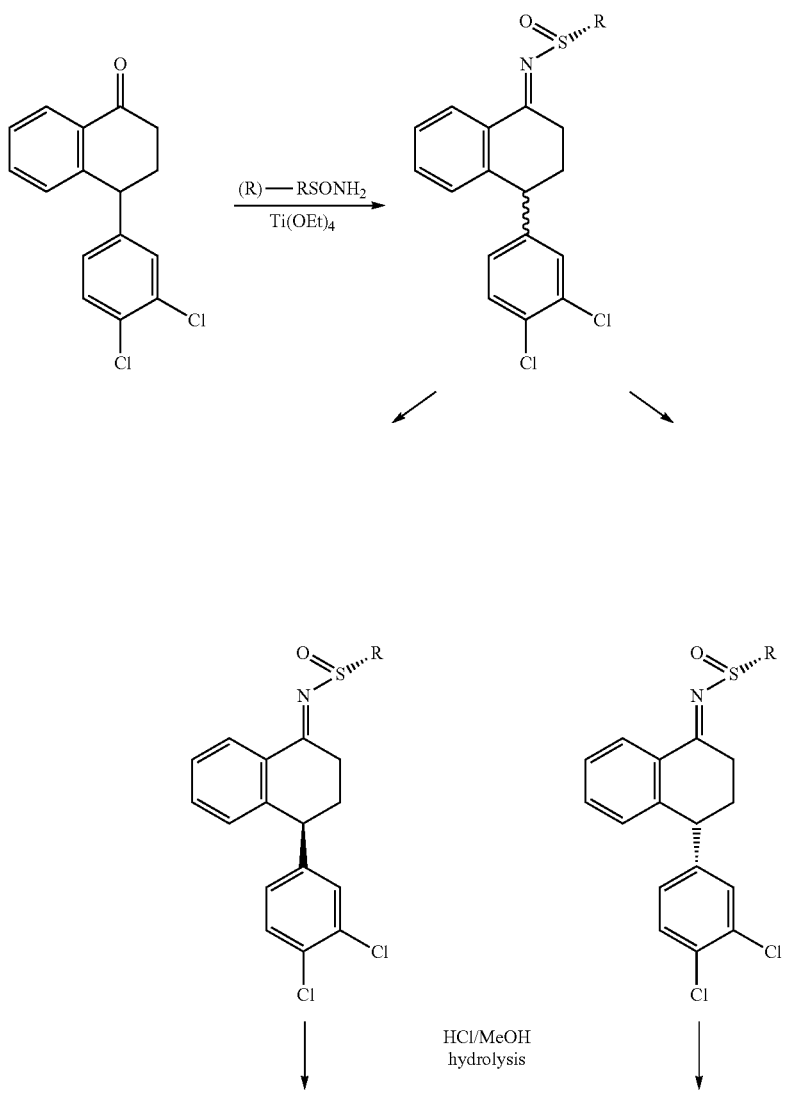
HCl/MeOH
hydrolysis -continued
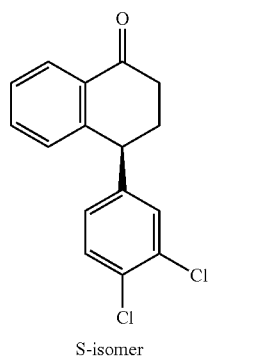
S-isomer
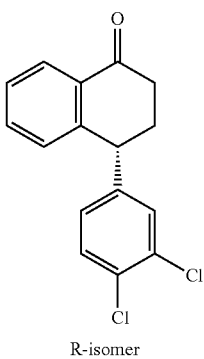
R-isomer
HCONH$_2$/HCOOH
160-170 C.
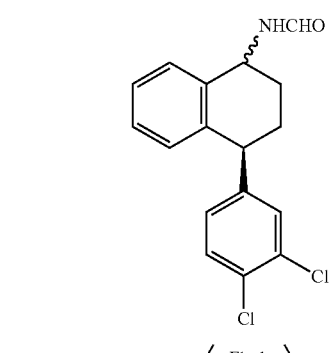
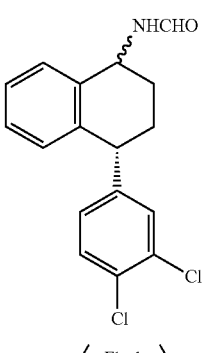
Flash Column
Flash Column
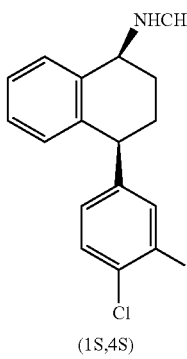
(1S,4S)
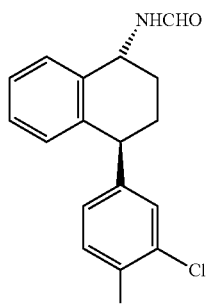
(1R,4S)
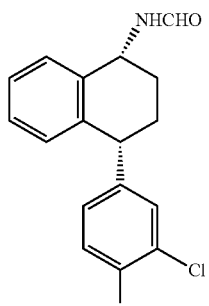
(1R,4R)
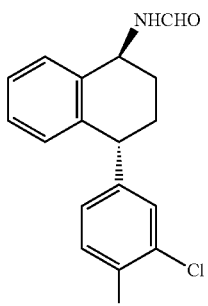
(1S,4R)
6N HCl, 80° C.
6N HCl, 80° C.
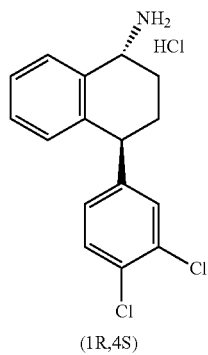
(1R,4S)
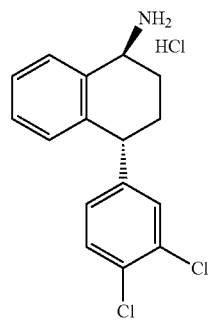
(1S,4R)

In the compound

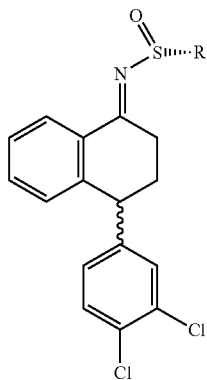

of Scheme 1,
R is

wherein $R^1$, $R^2$ and $R^3$ are each independently alkyl. In a preferred embodiment of the compounds, R is tert-butyl.

Synthesis of 2-methyl-propane-2-sulfinic acid [4-(3,4-dichlorophenyl)-1,2,3,4-tetrahydro-naphthalen-y-yl]-amide (tetralone t-butanesulfinimine): To a solution of 4((3,4-dicholorophenyl)-3,4-dihydro-1-naphthalenone (12 g) in THF (40 mL) was added (R)-t-butanesulfinamide (5.2 g) and Ti(OEt)$_4$ (85 mL 20%) in EtOH. The reaction mixture was heated to 60° C. for 13 h. The reaction mixture was cooled to rt, and poured into a brine solution (100 mL) with stirring. The suspension was then added to EtOAc (300 mL) and stirred for 10 min. The suspension was filtered and the filtrate was concentrated to ca 50 mL. One hundred milliliters of EtOAc was added and the organic phase was separated and concentrated to give a crude reaction mixture. The final products were isolated from the crude products by careful flash column chromatography using EtOAc and hexane (3:7 to 1:1) to give ca 3 g starting ketone, and (1R,4S)-4-(3,4-dichlorophenyl)-3,4-dihydro-1-naphthalenone tert-butanesulfinimine (2.5 g, first product) as an oil that solidified on standing. $^1$H NMR (CDCl$_3$) δ 1.33 (S, 9H), 2.10-2.20 (m, 1H), 2.28-2.38 (m, 1H) 2.88-2.98 (m, 1H), 3.34-3.44 (m 1H), 4.12-4.24 (m, 1H), 6.84-6.88 (m, 2H), 7.20 (s, 1H), 7.25-7.40 (m, 3H), 8.22-8.28 (m, 1H). The other product (1R,4R)-4-(3,4-dichloro phenyl)-3-4-dihydro-1-naphthalenone tert-butanesulfinimine (3.0 g, second product, lower R$_f$) was isolated also as an oil that solidified on standing. $^1$H NMR (CDCl$_3$) δ 1.34 (S, 9H), 2.05-2.18 (m, 1H), 2.28-2.38 (m, 1H), 3.15-3.25 (m, 2H), 4.16-4.22 (m, 1H), 6.84-6.88 (m, 2H), 7.20 (s, 1H), 7.25-7.40 (m, 3H), 8.22-8.28 (m, 1H).

Synthesis of (R)-4-(3,4-dichlorophenyl)-3,4-dihydro-1-naphthalenone: (1R,4R)-4-(3,4-dichlorophenyl)3,4-dihydro-1-naphthalenone t-butanesulfinimine (3.0 g, second product) was dissolved in MeOH (20 mL) and concentrated HCl (4 mL) at rt. The reaction mixture was stirred at rt to give a suspension. It was filtered and the solids were washed with hexane to give 1.2 g product. The enantiomeric purity was determined to be >99.3% by HPLC analysis with a ChiralPak AS10 µm, 4.6×250 mm, Hexane/IPA (90:10), UV 220 nm, R-isomer 8.23 min. S-isomer 12.25 min. $^1$H NMR (CDCl$_3$) δ 2.20-2.32 (m, 1H), 2.42-2.53 (m, 1H) 2.57-2.78 (m, 2H), 4.28 (dd=4.6, 8.1 Hz, 1H), 6.95 (dd, J=2.1, 7.6 Hz, 2H), 7.23 (d J=2.0 Hz, 1H), 7.37-50 (m, 3H), 8.13 (d, J=7.6 Hz, 1H). [α]=−66° (c=1, acetone).

Synthesis of (S)-4-(3,4-dichlorophenyl)-3,4-dihydro-1-naphthalenone The previous procedure was used, starting from (1R,4S)-4-(3,4-dichlorophenyl)-3,4-dihydro-1-naphthalenone tert-butanesulfinimine. 1.7 g of product (>99% ee) was obtained. [α]=+62 (c=1, acetone). $^1$H NMR spectrum of the product is the same as that of its enantiomer.

Synthesis of (1S,4R) and (1R,4R)—N-[4-(3,4-dichlorophenyl)-1,2,3,4-tetrahydro-naphthalen-1-yl]-formamide: (R)-4-(3,4-dichlorophenyl)-3,4-dihydro-1-naphthalenone (1.2 g) was added formic acid (3 mL) and formamide (3 mL). The reaction mixture was heated to 160-165° C. for 15 h under nitrogen atmosphere. The reaction mixture was cooled to rt and decanted the solvent. The residue solids was passed through flash column using EtOAc:Hexane (3:7 to 1:1) to give the (1R,4R)-formamide (400 mg, first spot), and the (1S,4R)-formamide (360 mg). $^1$H NMR of the first product [(1R,4R)-isomer]: (CDCl$_3$) δ 1.80-2.10 (m, 3H), 2.10-2.20 (m, 1H), 4.00-4.10 (m, 1H), 5.22-5.30 (m, 1H), 6.10-6.20 (m, 1H), 6.80-6.90 (M, 1H), 6.90-6.96 (m, 1H), 7.10-7.40 (m, 5H), 8.22 (s, 1H). M+320. $^1$H NMR of the second product [(1S,4R)-isomer: δ 1.64-1.90 (m, 2H), 2.10-2.28 (m, 2H), 4.10 (m, 1H), 5.38-5.42 (m, 1H), 5.82-6.05 (m, 1H), 6.80-6.90 (m, 2H), 7.10-40 (m, 5H), 8.28 (s, 1H). Mass Spec. M$^+$ 320.

Synthesis of (1S,4R)-trans 4-(3,4-dichlorophenyl)-1,2,3,4-tetrahydro-1-napthalenamine HCl: (1S,4R) formamide (ca 300 mg) was dissolved in MeOH (5 mL) followed by addition of 6N HCl (6 mL). The reaction mixture was heated to 80° C. for 2 h. The reaction mixture was cooled to rt for 1 h and filtered to collect the solid. It was washed with acetone (3 mL) and dried to give the product (280 mg). Enantiomeric purity was determined to be >99.8% by HPLC analysis with a ChiralPak AD 10 µm, 4.6×250 mm, Hexane/IPA/DEA (99:1:0.1), UV 220 nm, (1R,4S)-isomer, 11.00 min. (1S,4R)-isomer 11.70 min [α]=−51° (C.=1, MeOH). $^1$H NMR (CD$_3$OD) δ 1.86-1.97 (m, 2H), 2.20-2.42 (m, 2H), 4.30 (broad s, 1H), 4.67 (broad s, 1H), 4.87 (s, 3H), 6.95-6.99 (m, 2H), 7.18 (s, 1H), 7.28-7.50 (m, m, 4H). M$^+$ 293.

Synthesis of (1R,4S)-trans 4-(3,4-dichlorophenyl)-1,2,3,4-tetrahydro-1-napthalenamine HCl: It was obtained similarly from (1R,4S) formamide with HCl hydrolysis. Ee of the product is >99.8% based on HPLC analysis with a ChiralPak AD 10 µm, 4.6×250 mm, Hexane/IPA/DEA (99:1:0.1), UV 220 nm, (1R,4S)-isomer 11.00 min. (1S,4R)-isomer 11.70 min.

Synthesis of (1R,4R)-cis 4-(3,4-dichlorophenyl)-1,2,3,4-tetrahydro-1-napthalenamine HCl: It was obtained similarly from (1R,4R) formamide with HCl hydrolysis. Enantiomeric purity was determined to be 96.8% by HPLC analysis with a ChiralPak AD 10 µm, 4.6×250 mm, Hexane/IPA/DES (99:1:0.1), UV 220 nm, (1R,4R)-isomer 11.84 min. (1S,4S)-isomer 9.80 min. $^1$H NMR (CD$_3$OD) δ 1.96-2.26 (m, 4H), 4.14-4.22 (m, 1H), 4.54-4.63 (m, 1H), 4.87 (s, 3H), 7.88-7.94 (m, 1H), 7.18-7.20 (m, 1H), 7.30-7.50 (m, 5H). Mass Spec M$^+$ 292.

Synthesis of (1S,4S)-cis 4-(3,4-dichlorophenyl)-1,2,3,4-tetrahydro-1-napthalenamine HCl: It was obtained similarly from (1S,4S) formamide. Ee of the product was 98.5% by HPLC analysis. $^1$H NMR spectrum is the same as the enantiomer. Mass Spec M$^+$ 292.

Alternatively, compound P may be prepared as illustrated below in Scheme 3 and its accompanying narrative.

Scheme 3
Production (1R,4S)-4-(3,4-dichloro-phenyl)-1,2,3,4-tetrahydro-naphthalen-1-ylamine HCl from 4-(S)-(3,4-dichloro-phenyl)-3,4-dihydro-2H-naphthalen-1-one.

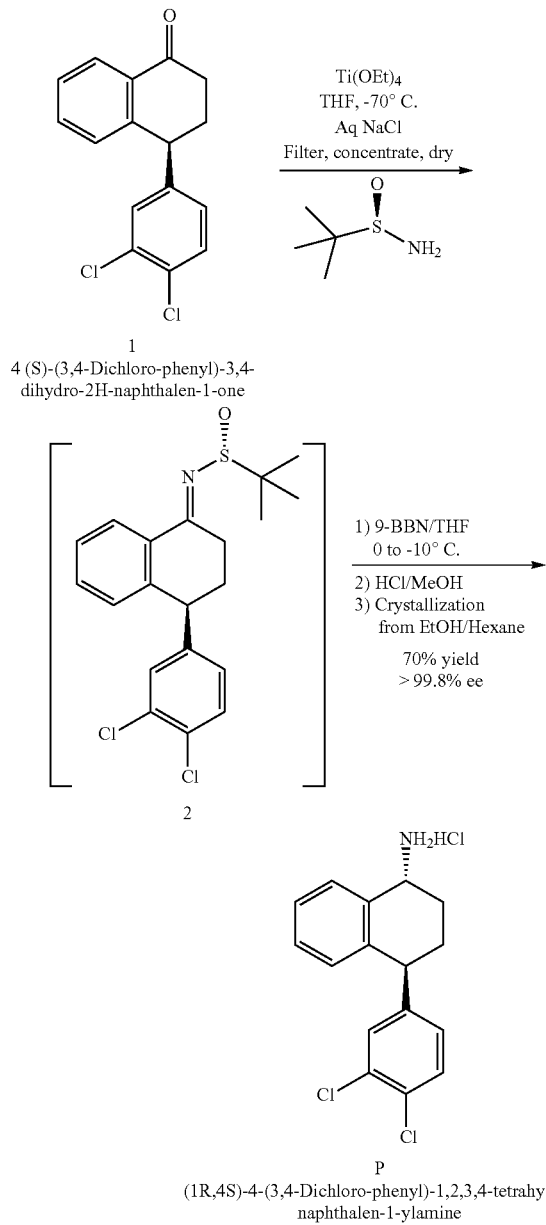

Charge 4-(S)-(3,4-dichloro-phenyl)-3,4-dihydro-2H-naphthalen-1-one (1 kg, 3.4 mol) and (R)-tert-butylsulphinamide (TBSA, 464 g, 3.8 mol) to a suitable reactor and dissolved in about 7 L THF. Add a 20% wt solution of Titanium ethoxide in ethanol (about 7.8 kg, 6.9 mol) and heat the mixture to about 70° C. for about 24 h. The reaction is monitored by HPLC, and after the reaction is complete, cool the mixture to room temperature and added a 24% wt aqueous solution of NaCl to the mixture. The resultant slurry was filtered and washed multiple times with about 1 L total of ethyl acetate. The mother liquors and washes were concentrated to a minimum volume. The aqueous phase was extracted with about 5 L of ethyl acetate and evaporated to dryness.

The contents were then dissolved in about 7 L of THF and cooled to about −10° C. About 9 kg, (~5 mol) of a 0.5 M solution of 9-borabicyclononane (9-BBN) in THF, was added slowly (about 3 h) and the mixture was stirred at 0° C. until reaction completion. A 6N HCl/methanol (~2 L) was added to the mixture and stirred until the hydrolysis reaction was complete. After neutralization with about 2 L of 6N aqueous NaOH, the mixture was distilled to remove THF and the residue (aqueous phase) was extracted twice with methyl t-butyl ether (2×6 L). The organic phase was then washed with water. The organic phase was concentrated, then cooled to 0° C. followed by addition of 2N HCl in methyl t-butyl ether (3 L). The product slowly precipitated as the HCl salt during the addition. The slurry was filtered and washed with methyl t-butyl ether (2×2 L). The product was dried under vacuum at about 45° C. to afford about 850 g of Re-Crystallization of crude (1R,4S)-4-(3,4-dichloro-phenyl)-1,2,3,4-tetrahydro-naphthalen-1-ylamine HCl.

The resulting (1R,4S)-4-(3,4-dichloro-phenyl)-1,2,3,4-tetrahydro-naphthalen-1-ylamine HCl (850 g) was charged to a suitable reactor and about 30 L of denatured ethanol was added. The mixture was heated to reflux, the volume was reduced to about 50% via distillation, and then cooled to 50° C. About 30 L of Hexane was added to the slurry to complete the product crystallization and then the slurry was cooled to about 0° C. The product was isolated by filtration, the cake was washed with about 2 L of ethanol/hexane (⅓ v/v) and then about 2 L of ethyl acetate, followed by about 3 L of hexane. The wet cake was dried under vacuum at about 45° C. to afford 630 g of product.

Another alternative process for preparation of compound P is presented below.

4-(S)-(3,4-dichloro-phenyl)-3,4-dichloro-2H-naphthalen-1-one (4.11 kg) and (R)-tert-butylsulphinamide (TBSA, 1.9 kg) were charged to a suitable reactor and dissolved in 29 L THF. A 20% wt solution of titanium ethoxide in ethanol (31.6 kg) was added and the mixture was heated to 70° C. with stirring. The reaction is monitored by HPLC, and after the reaction was complete (20-24 h) the mixture was cooled to room temperature and added to 20 L of a 24 wt % aqueous solution of NaCl. The resultant slurry was filtered and washed 3 times with ethyl acetate (4.1 L). The mother liquors and washes were concentrated to a minimum volume. The aqueous phase was extracted with about 20 L of a 1:1 mix of ethyl acetate and toluene. The organic phases were combined and concentrated to half volume to give a solution of 2. A purified sample of 2 was analyzed: m.p. 104° C., $^1$H NMR (400 MHz, CDCl$_3$) δ (ppm) 8.23 (dd, 1H, J=7.9, 0.9 Hz), 7.38 (ddd, 1H, J=14.7, 7.3, 1.5 Hz), 7.37 (d, 1H, J=8.4 Hz), 7.33 (d, 1H, J=7.7 Hz), 7.17 (d, 1H, J=1.8 Hz), 6.93 (d, 1H, J=7.7 Hz), 6.89 (dd, 1H, J=8.4, 2.2 Hz), 4.18 (dd, 1H, J=7.3, 4.8 Hz), 3.36 (ddd, 1H, J=17.5, 8.8, 4.4 Hz), 2.93 (ddd, 1H, J=17.6, 8.3, 4.2 Hz), 2.33 (m, 1H), 2.15 (m, 1H), 1.34 (s, 9H). $^{13}$C NMR (100 MHz, CDCl$_3$) δ 175.8, 144.2, 142.7, 132.6, 130.8, 130.7, 129.7, 128.1, 127.6, 127.4, 57.8, 44.3, 31.1, 29.4, 22.8. HRMS calc for $C_{20}H_{21}Cl_2NOS$ 394.0799, found 394.0767.

The solution of imine (2) was cooled to −10° C. and 36.3 kg of a 0.5 M solution of 9-borabicyclononane (9-BBN) in THF, was added slowly (over 3 h) and the mixture was stirred at 0° C. until reaction completion. A 4N HCl/methanol (8 L) was added to the mixture and stirred until the hydrolysis reaction was complete. After neutralization with about 15 kg of 6N aqueous NaOH (pH 8), the mixture was distilled to remove THF and methanol. The residue (aqueous phase) was extracted twice with methyl t-butyl ether (2×16 L). The organic phase was then washed with water. The organic phase was concentrated, then cooled to 0° C. followed by addition of 2N HCl in methyl t-butyl ether (5.4 kg). The product precipitated as the HCl salt. The slurry was filtered, washed with methyl t-butyl ether (2×8 L) and dried under vacuum at 45° C. to afford about 3.73 kg of crude (1R,4S)-4-(3,4-dichloro-phenyl)-1,2,3,4-tetrahydro-naphthalen-1-ylamine HCl (compound P). A purified sample of P was analyzed: m.p. 152-154° C., $^1$H NMR (400 MHz, CDCl$_3$) δ (ppm) 7.58 (d, 1H, J=7.7 Hz), 7.29 (m, 2H), 7.18 (br. t, 1H, J=7.5 Hz), 7.09 (d, 1H, J=1.8 Hz), 6.87 (d, 1H, J=7.7 Hz), 6.80 (dd, 1H, J=8.3, 2.0 Hz), 4.65 (dd, 1H, J=4.4, 4.4 Hz), 4.15 (t, 1H, J=5.5 Hz), 3.30 (d, 1H, J=3.7 Hz), 2.35 (m, 1H), 1.95 (m, 1H), 1.85 (m, 1H), 1.75 (m, 1H), 1.23 (s, 9H). $^{13}$C NMR (100 MHz, CDCl$_3$) δ 147.1, 138.4, 138.0, 132.6, 130.8, 130.6, 130.5, 129.8, 128.3, 127.9, 55.8, 53.3, 44.0, 28.2, 27.7, 22.9. HRMS calc for C$_{20}$H$_{23}$Cl$_2$NOS 396.0956, found 396.0968.

The crude (1R,4S)-4-(3,4-dichloro-phenyl)-1,2,3,4-tetrahydro-naphthalen-1-ylamine HCl (3.63 kg) was charged to a suitable reactor and 128 L of denatured ethanol was added. The mixture was stirred at reflux and polish filtered. The volume was reduced to about 50% via distillation, and then cooled to 50° C. 80 L of heptane was added to the slurry to complete the product crystallization and then the slurry was cooled to −5° C. The product was filtered, the cake was washed twice with 5.7 L of ethanol/heptane (1/1 v/v) and then washed with 6 L of hexane. The wet cake was dried under vacuum at about 45° C. to afford 2.57 kg of product. The product had a chemical purity of 99.65 A % and a diastereomeric purity in excess of 99%.

Thus, the invention is also directed to a novel method of preparation of compound P as a free base or as an acid addition salt. In one embodiment, the process for preparation of compound P comprises:

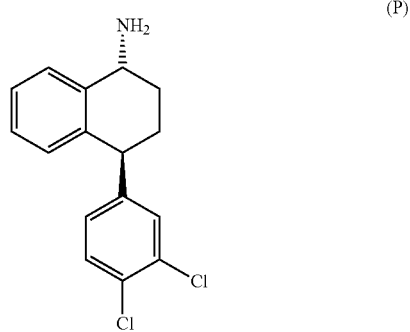
(P)

a) reacting a compound of formula 1

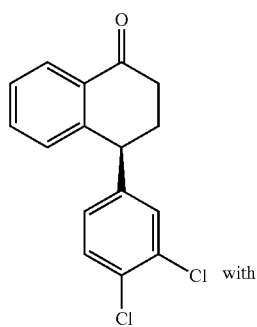
(1)

with

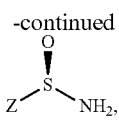

wherein Z is chosen from aryl, aryl substituted by alkyl, alkyl substituted by aryl, and —CR$^4$R$^5$R$^6$, wherein R$^4$ is C$_1$-C$_6$ alkyl, R$^5$ is C$_1$-C$_6$ alkyl, and R$^6$ is C$_1$-C$_6$ alkyl, in presence of a dehydrating agent to obtain compound of formula 2a

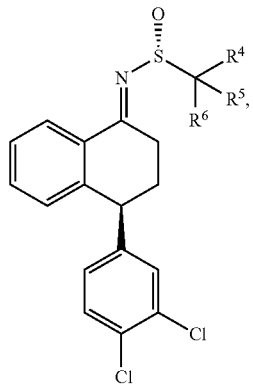
(2a)

and
b) reducing the compound of formula 2a with a hydride reducing agent followed by solvolysis.

In one embodiment, Z is tert-butyl, wherein each of R$^4$, R$^5$, and R$^6$ is methyl.

In one embodiment, the solvolysis is catalyzed by acid. In an optional further step, the process further comprises crystallizing an acid addition salt of the compound of formula P.

In another embodiment, the process further involves recrystallizing an acid addition salt of the compound of formula P from a solvent selected from an alcohol and a mixture of alcohol and hydrocarbon solvent. An example of hydrocarbon solvent is toluene.

At any point, when an acid addition salt of compound P is obtained, a further step may be performed of converting of an acid addition salt to a free base of compound P. The converting step may comprise treating with a base.

The dehydrating agent may be selected from titanium alkoxide, boron trifluoride etherate, boron trifluoride etherate with magnesium sulfate, and molecular sieves. The titanium alkoxide may be selected from titanium ethoxide and titanium isopropoxide.

The reducing agent may selected from 9-borabicyclononane, sodium borohydride, catechol borane, borane, and diisobutylaluminum hydride with zinc halide. The reducing step may be carried out in a solvent comprising tetrahydrofuran.

The acid that may be used in the solvolysis step may be a hydrochloric acid. The solvolysis step may be a hydrolysis reaction, or may be performed under non-aqueous conditions, for example, by use of methanol/acid mixture.

The compounds P and Q were tested for their inhibition of functional uptake of serotonin (5-HT), norepinephrine (NE), or dopamine (DA), in synaptosomes prepared from rat whole brain, hypothalamus, or corpus striatum, respectively. Compounds were tested initially at 10 μM in duplicate, and if ≧50% inhibition of uptake was observed, they were tested further at 10 different concentrations in duplicate in order to obtain full inhibition curves. $IC_{50}$ values (concentration inhibiting control activity by 50%) were then determined by nonlinear regression analysis of the inhibition curves and tabulated below in the Examples section.

Combination Therapy

One aspect of the present invention relates to combination therapy. This type of therapy is advantageous because the co-administration of active ingredients achieves a therapeutic effect that is greater than the therapeutic effect achieved by administration of only a single therapeutic agent. In one embodiment, the co-administration of two or more therapeutic agents achieves a synergistic effect, i.e., a therapeutic affect that is greater than the sum of the therapeutic effects of the individual components of the combination. In another embodiment, the co-administration of two or more therapeutic agents achieves an augmentation effect.

The active ingredients that comprise a combination therapy may be administered together via a single dosage form or by separate administration of each active agent. In certain embodiments, the first and second therapeutic agents are administered in a single dosage form. The agents may be formulated into a single tablet, pill, capsule, or solution for parenteral administration and the like.

Alternatively, the first therapeutic agent and the second therapeutic agents may be administered as separate compositions, e.g., as separate tablets or solutions. The first active agent may be administered at the same time as the second active agent or the first active agent may be administered intermittently with the second active agent. The length of time between administration of the first and second therapeutic agent may be adjusted to achieve the desired therapeutic effect. In certain instances, the second therapeutic agent may be administered only a few minutes (e.g., 1, 2, 5, 10, 30, or 60 min) after administration of the first therapeutic agent. Alternatively, the second therapeutic agent may be administered several hours (e.g., 2, 4, 6, 10, 12, 24, or 36 hr) after administration of the first therapeutic agent. In certain embodiments, it may be advantageous to administer more than one dosage of the second therapeutic agent between administrations of the first therapeutic agent. For example, the second therapeutic agent may be administered at 2 hours and then again at 10 hours following administration of the first therapeutic agent. Alternatively, it may be advantageous to administer more than one dosage of the first therapeutic agent between administrations of the second therapeutic agent. Importantly, it is preferred that the therapeutic effects of each active ingredient overlap for at least a portion of the duration of each therapeutic agent so that the overall therapeutic effect of the combination therapy is attributable in part to the combined or synergistic effects of the combination therapy.

The dosage of the active agents will generally be dependent upon a number of factors including pharmacodynamic characteristics of each agent of the combination, mode and route of administration of active agent(s), the health of the patient being treated, the extent of treatment desired, the nature and kind of concurrent therapy, if any, and the frequency of treatment and the nature of the effect desired. In general, dosage ranges of the active agents often range from about 0.001 to about 250 mg/kg body weight per day. For example, for a normal adult having a body weight of about 70 kg, a dosage in the range of from about 0.1 to about 25 mg/kg body weight is typically preferred. However, some variability in this general dosage range may be required depending upon the age and weight of the subject being treated, the intended route of administration, the particular agent being administered and the like. Since two or more different active agents are being used together in a combination therapy, the potency of each agent and the interactive effects achieved using them together must be considered. Importantly, the determination of dosage ranges and optimal dosages for a particular mammal is also well within the ability of one of ordinary skill in the art having the benefit of the instant disclosure.

In certain embodiments, it may be advantageous for the pharmaceutical combination to have a relatively large amount of the first component compared to the second component. In certain instances, the ratio of the first active agent to second active agent is 30:1, 20:1, 15:1, 10:1, 9:1, 8:1, 7:1, 6:1, or 5:1. In certain embodiments, it may be preferable to have a more equal distribution of pharmaceutical agents. In certain instances, the ratio of the first active agent to the second active agent is 4:1, 3:1, 2:1, 1:1, 1:2, 1:3, or 1:4. In certain embodiments, it may be advantageous for the pharmaceutical combination to have a relatively large amount of the second component compared to the first component. In certain instances, the ratio of the second active agent to the first active agent is 30:1, 20:1, 15:1, 10:1, 9:1, 8:1, 7:1, 6:1, or 5:1. Importantly, a composition comprising any of the above-identified combinations of first therapeutic agent and second therapeutic agent may be administered in divided doses 1, 2, 3, 4, 5, 6, or more times per day or in a form that will provide a rate of release effective to attain the desired results. In a preferred embodiment, the dosage form contains both the first and second active agents. In a more preferred embodiment, the dosage form only has to be administered one time per day and the dosage form contains both the first and second active agents.

For example, a formulation intended for oral administration to humans may contain from 0.1 mg to 5 g of the first therapeutic agent and 0.1 mg to 5 g of the second therapeutic agent, both of which are compounded with an appropriate and convenient amount of carrier material varying from about 5 to about 95 percent of the total composition. Unit dosages will generally contain between from about 0.5 mg to about 1500 mg of the first therapeutic agent and 0.5 mg to about 1500 mg of the second therapeutic agent. In a preferred embodiment, the dosage comprises 0.5 mg, 1 mg, 2 mg, 3 mg, 4 mg, 5 mg, 10 mg, 25 mg, 50 mg, 100 mg, 200 mg, 300 mg, 400 mg, 500 mg, 600 mg, 800 mg, or 1000 mg, etc., up to 1500 mg of the first therapeutic agent. In a preferred embodiment, the dosage comprises 0.5 mg, 1 mg, 2 mg, 3 mg, 4 mg, 5 mg, 10 mg, 25 mg, 50 mg, 100 mg, 200 mg, 300 mg, 400 mg, 500 mg, 600 mg, 800 mg, or 1000 mg, etc., up to 1500 mg of the second therapeutic agent. The optimal ratios of the first and second therapeutic agent can be determined by standard assays known in the art.

The toxicity and therapeutic efficacy of compositions of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of RT production from infected cells compared to untreated control as determined in cell culture. Such information can be used to more accurately determine useful doses in humans. Levels in plasma may be measured, for example, by high performance liquid chromatography (HPLC).

Synergism and Augmentation

The term "synergistic" refers to a combination which is more effective than the additive effects of any two or more single agents. A synergistic effect permits the effective treatment of a disease using lower amounts (doses) of either individual therapy. The lower doses result in lower toxicity without reduced efficacy. In addition, a synergistic effect can result in improved efficacy, e.g., improved antidepressant activity. Finally, synergy may result in an improved avoidance or reduction of disease as compared to any single therapy.

Combination therapy can allow for the use of lower doses of the first therapeutic or the second therapeutic agent (referred to as "apparent one-way synergy" herein), or lower doses of both therapeutic agents (referred to as "two-way synergy" herein) than would normally be required when either drug is used alone.

In certain embodiments, the synergism exhibited between the second therapeutic agent and the first therapeutic agent is such that the dosage of the first therapeutic agent would be sub-therapeutic if administered without the dosage of the second therapeutic agent. Alternatively, the synergism exhibited between the second therapeutic agent and the first therapeutic agent is such that the dosage of the second therapeutic agent would be sub-therapeutic if administered without the dosage of the first therapeutic agent.

The terms "augmentation" or "augment" refer to combination where one of the compounds increases or enhances therapeutic effects of another compound or compounds administered to a patient. In some instances, augmentation can result in improving the efficacy, tolerability, or safety, or any combination thereof, of a particular therapy.

In certain embodiments, the present invention relates to a pharmaceutical composition comprising a therapeutically effective dose of a first therapeutic agent together with a dose of a second therapeutic agent effective to augment the therapeutic effect of the first therapeutic agent. In other embodiments, the present invention relates to methods of augmenting the therapeutic effect in a patient of a first therapeutic agent by administering the second therapeutic agent to the patient. In other embodiments, the present invention relates to a pharmaceutical composition comprising an therapeutically effective dose of a second therapeutic agent together with a dose of a first therapeutic agent effective to augment the therapeutic effect of the second therapeutic agent. In other embodiments, the present invention relates to methods of augmenting the therapeutic effect in a patient of a second therapeutic agent by administering the first therapeutic agent to the patient.

In certain preferred embodiments, the invention is directed in part to synergistic combinations of the first therapeutic agent in an amount sufficient to render a therapeutic effect together with a second therapeutic agent. For example, in certain embodiments a therapeutic effect is attained which is at least about 2 (or at least about 4, 6, 8, or 10) times greater than that obtained with the dose of the first therapeutic agent alone. In certain embodiments, the synergistic combination provides a therapeutic effect which is up to about 20, or 40 times greater than that obtained with the dose of first therapeutic agent alone. In such embodiments, the synergistic combinations display what is referred to herein as an "apparent one-way synergy", meaning that the dose of second therapeutic agent synergistically potentiates the effect of the first therapeutic agent, but the dose of first therapeutic agent does not appear to significantly potentiate the effect of the second therapeutic agent.

In certain embodiments, the combination of active agents exhibit two-way synergism, meaning that the second therapeutic agent potentiates the effect of the first therapeutic agent, and the first therapeutic agent potentiates the effect of the second therapeutic agent. Thus, other embodiments of the invention relate to combinations of a second therapeutic agent and a first therapeutic agent where the dose of each drug is reduced due to the synergism between the drugs, and the therapeutic effect derived from the combination of drugs in reduced doses is enhanced. The two-way synergism is not always readily apparent in actual dosages due to the potency ratio of the first therapeutic agent to the second therapeutic agent. For instance, two-way synergism can be difficult to detect when one therapeutic agent displays much greater therapeutic potency relative to the other therapeutic agent.

The synergistic effects of combination therapy may be evaluated by biological activity assays. For example, the therapeutic agents are be mixed at molar ratios designed to give approximately equipotent therapeutic effects based on the $EC_{90}$ values. Then, three different molar ratios are used for each combination to allow for variability in the estimates of relative potency. These molar ratios are maintained throughout the dilution series. The corresponding monotherapies are also evaluated in parallel to the combination treatments using the standard primary assay format. A comparison of the therapeutic effect of the combination treatment to the therapeutic effect of the monotherapy gives a measure of the synergistic effect. Further details on the design of combination analyses can be found in B E Korba (1996) Antiviral Res. 29:49. Analysis of synergism, additivity, or antagonism can be determined by analysis of the aforementioned data using the CalcuSyn™ program (Biosoft, Inc.). This program evaluates drug interactions by use of the widely accepted method of Chou and Talalay combined with a statistically evaluation using the Monte Carlo statistical package. The data are displayed in several different formats including median-effect and dose-effects plots, isobolograms, and combination index [CI] plots with standard deviations. For the latter analysis, a CI greater than 1.0 indicates antagonism and a CI less than 1.0 indicates synergism.

Compositions of the invention present the opportunity for obtaining relief from moderate to severe cases of disease. Due to the synergistic and/or additive effects provided by the inventive combination of the first and second therapeutic agent, it may be possible to use reduced dosages of each of therapeutic agent. By using lesser amounts of other or both drugs, the side effects associated with each may be reduced in number and degree. Moreover, the inventive combination avoids side effects to which some patients are particularly sensitive.

Formulations and Definitions

Pharmaceutical compositions of the present invention may be administered by any suitable route of administration that provides a patient with a therapeutically effective dosage of the active ingredients. Typically, the pharmaceutical compositions described herein will be formulated for oral administration or for inhalation. Suitable dosage forms include tablets, troches, cachets, caplets, capsules, including hard and soft gelatin capsules, and the like. Tablet forms, however, remain a preferred dosage form because of advantages afforded both the patient (e.g., accuracy of dosage, compactness, portability, blandness of taste and ease of administration) and to the manufacturer (e.g., simplicity and economy of preparation, stability and convenience in packaging, shipping and dispensing).

The pharmaceutical compositions may further include a "pharmaceutically acceptable inert carrier" and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques. In one embodiment, coating with hydroxypropylmethylcellulose (HPMC) is employed. "Pharmaceutically acceptable carrier" also encompasses controlled release means. Compositions of the present invention may also optionally include other therapeutic ingredients, anti-caking agents, preservatives, sweetening agents, colorants, flavors, desiccants, plasticizers, dyes, and the like. However, any such optional ingredient must be compatible with combination of active ingredients to insure the stability of the formulation.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. In one embodiment, eszopiclone is formulated as a succinate salt. In another embodiment, eszopiclone is formulated as a fumarate salt.

Eszopiclone, trans 4-(3,4-dichlorophenyl)-1,2,3,4-tetrahydro-N-methyl-1-napthalenamine, and trans 4-(3,4-dichlorophenyl)-1,2,3,4-tetrahydro-1-napthalenamine are chiral compounds that can exist as a racemic mixture, a non-equal mixture of enantiomers, or as a single enantiomer. Importantly, the recitation of a compound that can exist as a racemic mixture, a non-equal mixture of enantiomers, or a single enantiomer is meant to encompass all three aforementioned forms, unless stated otherwise. The term "enantiomeric excess" is well known in the art and is defined for a resolution of ab into a+b as:

$$ee_a = \left(\frac{conc. \ of \ a - conc. \ of \ b}{conc. \ of \ a + conc. \ of \ b}\right) \times 100$$

The term "enantiomeric excess" is related to the older term "optical purity" in that both are measures of the same phenomenon. The value of e.e. will be a number from 0 to 100, zero being racemic and 100 being pure, single enantiomer. A compound which in the past might have been called 98% optically pure is now more precisely described as 96% e.e.; in other words, a 90% e.e. reflects the presence of 95% of one enantiomer and 5% of the other in the material in question. In instances when a specific enantiomer is recited (e.g., eszopiclone) for use in the compositions or methods of the present invention, this indicates that the composition contains a significantly greater proportion of the specified enantiomer in relation to the non-specified enantiomer. In a preferred embodiment, compositions comprising a specified enantiomer contain the specified enantiomer in at least 90% e.e. More preferably, such compositions comprising a specified enantiomer contain the specified enantiomer in at least 95% e.e. Even more preferably, such compositions comprising a specified enantiomer contain the specified enantiomer in at least 98% e.e. Most preferably, such compositions comprising a specified enantiomer contain the specified enantiomer in at least 99% e.e.

For example, compositions comprising eszopiclone contain the S-enantiomer of zopiclone in at least 90% e.e. More preferably, compositions comprising eszopiclone contain the S-enantiomer of zopiclone in at least 95% e.e. Even more preferably, such compositions comprising eszopiclone contain the S-enantiomer of zopiclone in at least 98% e.e. Most preferably, such compositions comprising eszopiclone contain the S-enantiomer of zopiclone in at least 99% e.e.

The graphic representations of racemic, ambiscalemic and scalemic or enantiomerically pure compounds used herein are taken from Maehr, J. Chem. Ed., 62:114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

The term "antagonist" refers to a compound that binds to a receptor binding site, but does not activate the receptor, a compound that binds to a receptor and blocks receptor binding site, or a compound that binds to an allosteric site on a receptor (non-competitive antagonist) resulting in prevention of activation of the receptor by its ligand. The resulting inhibition of the receptor may vary in degree and duration.

The term "patient" refers to a mammal in need of a particular treatment. In a preferred embodiment, a patient is a primate, canine, feline, or equine. In another preferred embodiment, a patient is a human.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "solvate" refers to a pharmaceutically acceptable form of a specified compound, with one or more solvent molecules, that retains the biological effectiveness of such compound. Examples of solvates include compounds of the invention in combination with solvents such, for example, water (to form the hydrate), isopropanol, ethanol, methanol, dimethyl sulfoxide, ethyl acetate, acetic acid, ethanolamine, or acetone. Also included are formulations of solvate mixtures such as a compound of the invention in combination with two or more solvents.

The term "disorders" as used herein includes menopause, perimenopause, mood disorders, anxiety disorders, and cognitive disorders.

The term "menopause" as used herein includes various symptoms of menopause and perimenopause, such as hot flashes, awakenings due to hot flashes, nocturnal awakenings, and mood disorders associated with menopause or perimenopause, such as depression and anxiety.

The term "mood disorder" as used herein includes major depression, major depressive disorder, mild depression, severe depression without psychosis, severe depression with psychosis, melancholia (formerly endogenous depression), atypical depression, dysthymic disorder, manic depression, bipolar disorder, bipolar I disorder, bipolar II disorder, bipolar III disorder, cyclothymic disorder, and chronic hypomania.

The term "mood disorder" as used herein also includes premenstrual syndrome (PMS), premenstrual dysphoric disorder (PMDD), prenatal depression, and postpartum depression.

The term "anxiety disorder" as used herein refers to panic attacks, panic disorder, phobic disorders (such as agoraphobia, specific phobias, social phobia, avoidant personality disorder), obsessive-compulsive disorder (OCD), posttraumatic stress disorder, acute stress disorder, and generalized Anxiety Disorder.

The term "cognitive disorder" as used herein refers to delirium (acute confusional state), dementia, Alzheimer's Disease, Lewy body dementia, vascular dementia, Binswanger's dementia (subcortical arteriosclerotic encephalopathy), Parkinson's disease, progressive supranuclear palsy, Huntington's disease (chorea), Pick's disease, Klüver-Bucy syndrome, frontal lobe dementia syndromes, normal-pressure hydrocephalus, subdural hematoma, Creutzfeldt-Jakob disease, Gerstmann-Sträussler-Scheinker disease, general paresis, and AIDS dementia. The term "cognitive disorder" as used herein also includes decreased cognitive function and memory loss.

The term "treating" when used in connection with the disorders means amelioration, prevention or relief from the symptoms and/or effects associated with these disorders and includes the prophylactic administration of the compositions of the invention, or pharmaceutically acceptable salt thereof, to substantially diminish the likelihood or seriousness of the condition.

The invention now being generally described, it will be more readily understood by reference to the following examples, which are included merely for purposes of illustration of certain aspects and embodiments of the present invention, and are not intended to limit the invention.

EXAMPLES

Example 1

Formulations

The following formulations are exemplary of eszopiclone and trans 4-(3,4-dichlorophenyl)-1,2,3,4-tetrahydro-N-methyl-1-napthalenamine or trans 4-(3,4-dichlorophenyl)-1,2,3,4-tetrahydro-1-napthalenamine combination tablet or capsule formulations:

TABLE 1

Eszopiclone and trans 4-(3,4-dichlorophenyl)-1,2,3,4-tetrahydro-N-methyl-1-napthalenamine compositions

| Ingredient | Combo Strengths (Eszopiclone/trans 4-(3,4-dichlorophenyl)-1,2,3,4-tetrahydro-N-methyl-1-napthalenamine, mg/unit) | | |
|---|---|---|---|
| (Tablet and Capsule) | 3.0/25.0 | 3.0/50.0 | 3.0/100.0 |
| Eszopiclone | 3.00 | 3.00 | 3.00 |
| trans 4-(3,4-dichlorophenyl)-1,2,3,4-tetrahydro-N-methyl-1-napthalenamine HCl[1] | 28.00 | 56.00 | 112.00 |
| Microcrystalline Cellulose, NF (Avicel ® PH102) | 198.90 | 198.90 | 198.90 |
| Dibasic Calcium Phosphate Anhydrous USP | 90.00 | 90.00 | 90.00 |
| Croscarmellose Sodium, NF | 6.00 | 6.00 | 6.00 |
| Colloidal Silicon Dioxide, NF | 0.60 | 0.60 | 0.60 |
| Magnesium Stearate, NF | 1.50 | 1.50 | 1.50 |
| Total tablet wt. or capsule fill wt. | 328.00 | 356.00 | 412.00 |
| Empty Size 0 hard gelatin capsule wt. | 90.00 | 90.00 | 90.00 |
| Total weight of filled capsule | 418.00 | 446.00 | 502.00 |

[1]trans 4-(3,4-dichlorophenyl)-1,2,3,4-tetrahydro-N-methyl-1-napthalenamine HCl potency is expressed in terms of free base.
1.12 mg trans 4-(3,4-dichlorophenyl)-1,2,3,4-tetrahydro-N-methyl-1-napthalenamine HCl is equivalent to 1.00 mg of free base.

TABLE 2

Eszopiclone and trans 4-(3,4-dichlorophenyl)-1,2,3,4-tetrahydro-1-napthalenamine compositions

| Ingredient | Combo Strengths (Eszopiclone/trans 4-(3,4-dichlorophenyl)-1,2,3,4-tetrahydro-1-napthalenamine, mg/unit) | | |
|---|---|---|---|
| (Tablet and Capsule) | 3.0/25.0 | 3.0/50.0 | 3.0/100.0 |
| Eszopiclone | 3.00 | 3.00 | 3.00 |
| trans 4-(3,4-dichlorophenyl)-1,2,3,4-tetrahydro-1-napthalenamine HCl[1] | 28.00 | 56.00 | 112.00 |
| Microcrystalline Cellulose, NF (Avicel ® PH102) | 198.90 | 198.90 | 198.90 |
| Dibasic Calcium Phosphate Anhydrous USP | 90.00 | 90.00 | 90.00 |
| Croscarmellose Sodium, NF | 6.00 | 6.00 | 6.00 |
| Colloidal Silicon Dioxide, NF | 0.60 | 0.60 | 0.60 |
| Magnesium Stearate, NF | 1.50 | 1.50 | 1.50 |
| Total tablet wt. or capsule fill wt. | 328.00 | 356.00 | 412.00 |
| Empty Size 0 hard gelatin capsule wt. | 90.00 | 90.00 | 90.00 |
| Total weight of filled capsule | 418.00 | 446.00 | 502.00 |

[1]trans 4-(3,4-dichlorophenyl)-1,2,3,4-tetrahydro-1-napthalenamine HCl potency is expressed in terms of free base.
1.12 mg trans 4-(3,4-dichlorophenyl)-1,2,3,4-tetrahydro-1-napthalenamine HCl is equivalent to 1.00 mg of free base.

The above-presented formulations may be prepared by performing the following steps:
1. Screen eszopiclone through 80 mesh.
2. Screen trans 4-(3,4-dichlorophenyl)-1,2,3,4-tetrahydro-N-methyl-1-napthalenamine or trans 4-(3,4-dichlorophenyl)-1,2,3,4-tetrahydro-1-napthalenamine through 40 mesh.
3. Screen remaining ingredients through #20 or #30 mesh screen.
4. Blend eszopiclone with a portion of MCC (microcrystalline cellulose).
5. Blend trans 4-(3,4-dichlorophenyl)-1,2,3,4-tetrahydro-N-methyl-1-napthalenamine or trans 4-(3,4-dichlorophenyl)-1,2,3,4-tetrahydro-1-napthalenamine with the blend from Step 4.

6. Blend the mixture from Step 5 with remaining MCC in three steps.
7. Blend mixture from Step 6 with dicalcium phosphate.
8. Mix croscarmellose with silicon dioxide, then blend with the mixture from Step 7.
9. Blend mixture from Step 8 with magnesium stearate.
10. For tablets, compress on a suitable tablet press machine.
11. For capsules, fill into Size 0 hard gelatin capsules on a suitable capsule filling machine.
12. For tablets, coat the tablet cores from Step 10 with Opadry II in a suitable conventional tablet coating machine.

Example 2

Clinical Study on Treatment of Menopause or Perimenopause with Eszopiclone

The study was aimed at observing efficacy of eszopiclone 3 mg compared to placebo in the treatment of insomnia secondary to perimenopause or menopause.

The study was a multicenter, randomized, double-blind, placebo-controlled, parallel-group study. The study had a one-week single-blind placebo run-in period, followed by four weeks of double blind treatment, and one week of single blind placebo wash-out. The primary method of analysis compared the post-randomization results between the two treatment groups.

Subjects were women with insomnia secondary to perimenopause or menopause. Subjects were perimenopausal or menopausal and had insomnia symptoms including ≧45 minutes sleep latency (SL) and total sleep time (TST)≦6 hours. Perimenopausal/menopausal symptoms predated the onset of sleep disturbance symptoms. The patient population was predominately Caucasian (77.2%). The mean age was 49, with a range of 40-60.

A total of 410 subjects were randomized. Among them, 201 received 3 mg of eszopiclone (ESZ) nightly (at bedtime) for four weeks and 209 received matching placebo (PBO). The discontinuation rates were moderate, 11.9% in the ESZ group and 12.9% in the PBO group.

The ESZ group had significantly fewer nocturnal awakenings due to hot flashes during Week 1 compared with PBO (LS means of 0.3 and 0.5 per night for ESZ and PBO, respectively; p=0.0016). This effect was not significant for the other weeks, but was marginally significant for the DB average (p=0.059). When change from baseline was analyzed, ESZ significantly reduced the number of nocturnal awakenings due to hot flashes in Week 1 compared with PBO (p<0.0001). The difference was not significant for Week 2, but was marginally significant for Weeks 3 and 4 (p=0.094 and 0.055, respectively) and was significant for the DB average (p=0.0045). See Table 3.

TABLE 3

Number of Nocturnal Awakenings due to Hot Flashes (Intent-to-Treat Population)

| Time Point | Statistic | Placebo Observed Value | Placebo Change from Baseline [1] | Eszopiclone 3 mg Observed Value | Eszopiclone 3 mg Change from Baseline [1] |
|---|---|---|---|---|---|
| Baseline | N | 171 | | 150 | |
| | Mean (SD) | 1.1 (1.2) | | 1.3 (1.2) | |
| | 25th Percentile | 0.0 | | 0.3 | |
| | Median | 1.0 | | 1.0 | |
| | 75th Percentile | 1.5 | | 2.0 | |
| | Minimum, Maximum | 0.0, 10.0 | | 0.0, 6.0 | |
| Week 1 | N | 179 | 157 | 175 | 140 |
| | Mean (SD) | 0.8 (1.0) | −0.2 (0.9) | 0.5 (0.7) | −0.7 (1.0) |
| | 25th Percentile | 0.0 | −0.7 | 0.0 | −1.2 |
| | Median | 0.5 | 0.0 | 0.2 | −0.5 |
| | 75th Percentile | 1.3 | 0.2 | 1.0 | 0.0 |
| | Minimum, Maximum | 0.0, 5.0 | −5.0, 2.3 | 0.0, 3.0 | −6.0, 0.8 |
| | Least Squares Means (SE) [2] | 0.8 (0.1) | | 0.5 (0.1) | |
| | p-value vs. placebo [2] | | | <.0001 | |
| | Least Squares Means (SE) [3] | | −0.3 (0.1) | | −0.7 (0.1) |
| | p-value vs. placebo [3] | | | | <.0001 |
| Week 2 | N | 174 | 153 | 170 | 139 |
| | Mean (SD) | 0.6 (0.8) | −0.5 (1.0) | 0.5 (0.7) | −0.7 (1.0) |
| | 25th Percentile | 0.0 | −1.0 | 0.0 | −1.0 |
| | Median | 0.3 | −0.4 | 0.0 | −0.6 |
| | 75th Percentile | 1.0 | 0.0 | 1.0 | 0.0 |
| | Minimum, Maximum | 0.0, 4.3 | −6.8, 1.3 | 0.0, 3.0 | −6.0, 2.0 |
| | Least Squares Means (SE) [2] | 0.6 (0.1) | | 0.5 (0.1) | |
| | p-value vs. placebo [2] | | | 0.2137 | |
| | Least Squares Means (SE) [3] | | −0.5 (0.1) | | −0.6 (0.1) |
| | p-value vs. placebo [3] | | | | 0.1963 |
| Week 3 | N | 162 | 147 | 164 | 129 |
| | Mean (SD) | 0.6 (0.8) | −0.5 (1.0) | 0.5 (0.7) | −0.7 (1.1) |
| | 25th Percentile | 0.0 | −0.8 | 0.0 | −1.0 |
| | Median | 0.3 | −0.3 | 0.0 | −0.4 |
| | 75th Percentile | 1.0 | 0.0 | 1.0 | 0.0 |
| | Minimum, Maximum | 0.0, 4.6 | −6.2, 2.7 | 0.0, 3.0 | −6.0, 1.5 |
| | Least Squares Means (SE) [2] | 0.6 (0.1) | | 0.5 (0.1) | |
| | p-value vs. placebo [2] | | | 0.1583 | |
| | Least Squares Means (SE) [3] | | −0.5 (0.1) | | −0.6 (0.1) |
| | p-value vs. placebo [3] | | | | 0.2408 |

TABLE 3-continued

Number of Nocturnal Awakenings due to Hot Flashes (Intent-to-Treat Population)

| Time Point | Statistic | Placebo Observed Value | Placebo Change from Baseline [1] | Eszopiclone 3 mg Observed Value | Eszopiclone 3 mg Change from Baseline [1] |
|---|---|---|---|---|---|
| Week 4 | N | 151 | 135 | 154 | 121 |
| | Mean (SD) | 0.6 (0.9) | −0.5 (1.0) | 0.4 (0.7) | −0.8 (1.2) |
| | 25th Percentile | 0.0 | −1.0 | 0.0 | −1.3 |
| | Median | 0.0 | −0.3 | 0.0 | −0.7 |
| | 75th Percentile | 1.0 | 0.0 | 1.0 | 0.0 |
| | Minimum, Maximum | 0.0, 5.3 | −4.8, 4.0 | 0.0, 3.6 | −6.0, 2.1 |
| | Least Squares Means (SE) [2] | 0.6 (0.1) | | 0.4 (0.1) | |
| | p-value vs. placebo [2] | | | 0.0786 | |
| | Least Squares Means (SE) [3] | | −0.5 (0.1) | | −0.7 (0.1) |
| | p-value vs. placebo [3] | | | | 0.0683 |
| DB Average | N | 192 | 165 | 188 | 146 |
| | Mean (SD) | 0.7 (0.8) | −0.4 (0.9) | 0.5 (0.6) | −0.7 (1.0) |
| | 25th Percentile | 0.0 | −0.8 | 0.0 | −1.1 |
| | Median | 0.4 | −0.2 | 0.2 | −0.5 |
| | 75th Percentile | 1.0 | 0.0 | 0.9 | 0.0 |
| | Minimum, Maximum | 0.0, 4.6 | −6.0, 1.5 | 0.0, 2.7 | −6.0, 1.5 |
| | Least Squares Means (SE) [2] | 0.7 (0.1) | | 0.5 (0.1) | |
| | p-value vs. placebo [2] | | | 0.0057 | |
| | Least Squares Means (SE) [3] | | −0.4 (0.0) | | −0.7 (0.1) |
| | p-value vs. placebo [3] | | | | 0.0016 |

[1] Week 1 = First week of double-blind treatment, Week 2 = Second week of double-blind treatment, etc. DB Average includes all scheduled assessments obtained after Visit 3 up to and including Visit 5. Baseline is the average of all pre-DB observations.
[2] The pairwise comparison is a two-sided test performed using an ANOVA model, using the MIXED procedure with treatment and site as fixed effects.
[3] The pairwise comparison is a two-sided test performed using an ANCOVA model, using the MIXED procedure with treatment and site as fixed effects and baseline as the covariate.

A Physician Global Assessment was administered at Week 4, the end of the double-blind treatment period. ESZ patients had significantly better scores at this time compared with PBO (LS means of 2.7 and 3.3 for ESZ and PBO, respectively; p<0.0001). See Table 4.

The results of the study will change slightly because data from one site, consisting of 11 of the 410 subjects analyzed above will be excluded due to negative findings during a site audit. It is expected that the conclusions of the study will not change after exclusion of these 11 subjects.

TABLE 4

Menopause and Perimenopause Study, Physician Global Assessment (Intent-to-Treat Population)

| Visit (Week) | Statistic | Placebo Observed Value | Placebo Change from Baseline | Eszopiclone 3 mg Observed Value | Eszopiclone 3 mg Change from Baseline |
|---|---|---|---|---|---|
| 3 (Baseline) | N | 202 | | 195 | |
| | Mean (SD) | 3.6 (1.0) | | 3.7 (1.0) | |
| | 25th Percentile | 3.0 | | 4.0 | |
| | Median | 4.0 | | 4.0 | |
| | 75th Percentile | 4.0 | | 4.0 | |
| | Minimum, Maximum | 0.0, 6.0 | | 0.0, 7.0 | |
| 5 (Week 4) | N | 191 | 188 | 189 | 185 |
| | Mean (SD) | 3.3 (1.1) | −0.3 (1.4) | 2.6 (1.2) | −1.0 (1.4) |
| | 25th Percentile | 2.0 | −1.0 | 2.0 | −2.0 |
| | Median | 4.0 | 0.0 | 2.0 | −1.0 |
| | 75th Percentile | 4.0 | 0.0 | 4.0 | 0.0 |
| | Minimum, Maximum | 1.0, 6.0 | −4.0, 5.0 | 1.0, 6.0 | −4.0, 6.0 |
| | Least Squares Means (SE) [1] | 3.3 (0.1) | | 2.7 (0.1) | |
| | p-value vs. placebo [1] | | | <.0001 | |
| | Least Squares Means (SE) [2] | | −0.3 (0.1) | | −0.9 (0.1) |
| | p-value vs. placebo [2] | | | | <.0001 |

[1] The pairwise comparison is a two-sided test performed using an ANOVA model, using the MIXED procedure with treatment and site as fixed effects.
[2] The pairwise comparison is a two-sided test performed using an ANCOVA model, using the MIXED procedure with treatment and site as fixed effects and baseline as the covariate.
Note(s):
The responses to the assessment question: Overall the subject's perimenopausal or menopausal symptoms since the last assessment are:
0 = Not assessed, 1 = Very much improved, 2 = Much improved, 3 = Minimally improved, 4 = No change, 5 = Minimally worse, 6 = Much worse, 7 = Very much worse.

Example 3 trans 4-(3,4-dichlorophenyl)-1,2,3,4-tetrahydro-N-methyl-1-napthalenamine Activity Assays Experimental Conditions for Monoamine Uptake Assays
Serotonin Functional Uptake Assay Characterization of serotonin uptake is performed using synaptosomes isolated in a 0.32 M sucrose buffer from a male Wistar rat cortex. The uptake of radiolabelled serotonin by synaptosomes (100 µg of proteins/point) is allowed by incubating them in a deep well for 15 minutes at 37° C. in presence of test compounds and [3H]5-hydroxytryptamin (0.1 µCi/point).

Synaptosomes and [$^3$H]5-hydroxytryptamine are prepared in a Krebs buffer pH 7.4 containing 25 mM $NaHCO_3$, 11 mM glucose and 50 µM ascorbic acid. This incubation buffer is oxygenated during 5 minutes before incubation. Basal control is incubated for 15 minutes at 4° C. in order to avoid any uptake. Following this incubation the uptake is stopped by filtration through an "unifilter 96-wells GFB "Packard plate washed with Krebs buffer containing 25 mM $NaHCO_3$ in order to eliminate the free [$^3$H]5-hydroxytryptamine. The radioactivity associated to the synaptosomes retained onto the unifilter corresponding to the uptake is then measured with a microplate scintillation counter Topcount, Packard using a scintillation liquid microscint 0, Packard.

The reference compound is imipramine tested at 10 concentrations ranging from $10^{-11}$ M to $10^{-5}$ M in order to obtain an $IC_{50}$ value. See, Perovics and Müller, "Pharmacological profile of hypericum extract: effect on serotonin uptake by postsynaptic receptors," *Arzeim. Forsch./Drug Res.*, 45:1145-1148 (1995).

Dopamine Functional Uptake Assay

Characterization of dopamine uptake is performed using synaptosomes isolated at Cerep in a 0.32 M sucrose buffer from a male Wistar rat striatum. The uptake of radiolabelled dopamine by synaptosomes (20 µg of proteins/point) is allowed by incubating them in a deep well for 15 minutes at 37° C. in presence of test compounds and [$^3$H]-dopamine (0.1 µCi/point).

Synaptosomes and [$^3$H]-dopamine are prepared in a Krebs buffer pH 7.4 containing 25 mM $NaHCO_3$, 11 mM glucose and 50 µM ascorbic acid. This incubation buffer is oxygenated during 5 minutes before incubation. Basal control is incubated for 15 minutes at 4° C. in order to avoid any uptake. Following this incubation the uptake is stopped by filtration through an "unifilter 96-wells GFB "Packard plate washed with Krebs buffer containing 25 mM $NaHCO_3$ in order to eliminate the free [$^3$H]-dopamine. The radioactivity associated to the synaptosomes retained onto the unifilter corresponding to the uptake is then measured with a microplate scintillation counter Topcount, Packard using a scintillation liquid microscint 0, Packard. The reference compound is GRB12909 tested at 8 concentrations ranging from $10^{-11}$ M to $10^{-6}$ M in order to obtain an $IC_{50}$ value. Jankowsky et al., "Characterization of sodium-dependent [$^3$H] GBR-12935 binding in brain: a radioligand for selective labeling of the dopamine transport complex," *J. Neurochem.*, 46:1272-1276 (1986).

Norepinephrine Functional Uptake Assay

Characterization of norepinephrine uptake is performed using synaptosomes isolated at Cerep in a 0.32 M sucrose buffer from a male Wistar rat hypothalamus. The uptake of radiolabeled norepinephrine by synaptosomes (100 µg of proteins/point) is allowed by incubating them in a deep well for 20 minutes at 37° C. in presence of test compounds and [$^3$H]-norepinephrine (0.1 µCi/point).

Synaptosomes and [$^3$H]-norepinephrine are prepared in a Krebs buffer pH 7.4 containing 25 mM $NaHCO_3$, 11 mM glucose and 50 µM ascorbic acid. This incubation buffer is oxygenated during 5 minutes before incubation. Basal control is incubated for 20 minutes at 4° C. in order to avoid any uptake. Following this incubation the uptake is stopped by filtration through an "unifilter 96-wells GFB "Packard plate washed with Krebs buffer containing 25 mM $NaHCO_3$ in order to eliminate the free [$^3$H]-norepinephrine. The radioactivity associated to the synaptosomes retained onto the unifilter corresponding to the uptake is then measured with a microplate scintillation counter Topcount, Packard using a scintillation liquid microscint 0, Packard.

The reference compound is imipramine tested at 13 concentrations ranging from $10^{-11}$ M to $10^{-5}$ M in order to obtain an $IC_{50}$ value. See, Perovics and Müller, "Pharmacological profile of hypericum extract: effect on serotonin uptake by postsynaptic receptors," *Arzeim. Forsch./Drug Res.*, 45:1145-1148 (1995).

TABLE 5

$IC_{50}$ Values (µM) for Sertraline and Analogues in Functional Monoamine Uptakes Assays

|  | 5-HT | NE | DA |
| --- | --- | --- | --- |
| sertraline | 0.0016 | 0.31 | 0.048 |
| (R,R) cis | 0.11 | 0.11 | 0.039 |
| A* | 0.0075 | 0.012 | 0.0046 |
| B** | 0.33 | 0.024 | 0.026 |
| A + B | 0.0070 | 0.0056 | 0.0073 |
| imipramine | 0.054/0.051 | — | — |
| protriptyline | — | 0.0036 | — |
| GBR 12909 | — | — | 0.0028/0.0051/0.0034 |

*A (1R,4S)-trans 4-(3,4-dichlorophenyl)-1,2,3,4-tetrahydro-N-methyl-1-napthalenamine
**B (1S,4R)-trans 4-(3,4-dichlorophenyl)-1,2,3,4-tetrahydro-N-methyl-1-napthalenamine
/ separates multiple determinations
— <50% inhibition The $IC_{50}$ value for (R,R) had to be estimated because the lowest plateau of the inhibition curve (corresponding to 100% inhibition) was not reached at the highest concentration tested or 100% or control activity was not apparent with the lowest concentration.

As shown in Table 5, A and B exhibit similar inhibitory potency on the neuronal uptake of NE, DA, and 5HT. Currently, the therapeutic approach to treating affective disorders in man is the selective inhibition of a single monoamine uptake mechanism or the dual inhibition of two of these molecular targets. The equipotent inhibition of neuronal uptake of NE, DA and 5HT provides the clinician with the ability to more effectively treat the disorders mentioned specifically herein by elevating all of the monoamine levels in the brain simultaneously and over the same dose-range without the need to titrate separate drugs.

Example 4 trans 4-(3,4-dichlorophenyl)-1,2,3,4-tetrahydro-1-napthalenamine Activity Assays Monoamine uptake assays were performed according to protocols provided in Example 3 above. Results are tabulated below.

TABLE 6

IC$_{50}$ Values (μM) for Compounds of the Invention in Functional Monoamine Uptake Assays

| | 5-HT | NE | DA |
|---|---|---|---|
| sertraline | 0.0016 | 0.31 | 0.048 |
| P | 0.0077 | 0.0096 | 0.0064 |
| Q | 0.088 | 0.035 | 0.019 |
| P + Q | 0.041 | 0.0088 | 0.0071 |
| imipramine (standard) | 0.054/0.051 | — | — |
| protriptyline (standard) | — | 0.0036 | — |
| GBR 12909 (standard) | — | — | 0.0028/0.0051/0.0034 |

/ separates multiple determinations
— <50% inhibition

As shown in Table 6, P and Q exhibit similar inhibitory potency on the neuronal uptake of NE, DA, and 5HT. Currently, the therapeutic approach to treating affective disorders in man is the selective inhibition of a single monoamine uptake mechanism or the dual inhibition of two of these molecular targets. The equipotent inhibition of the neuronal uptake of NE, DA and 5HT provides the clinician with the ability to more effectively treat affective disorders and eating disorders by elevating all of the monoamine levels in the brain simultaneously and over the same dose-range without the need to titrate separate drugs. For those CNS disorders that are presently treated with dopaminergic, norepinephrine or mixed DA-NE uptake inhibitors (e.g. OCD, ADD, ADHD, sexual dysfunction and substance abuse), the equipotent inhibition of the neuronal uptake of NE, DA and 5HT provides more effective treatment by adding the serotonergic effect.

Table 7 below presents data on effect of intraperitoneal administration of (1R,4S)—N-[4-(3,4-dichlorophenyl-1,2,3,4-tetrahydro-1-naphthalenamine (Compound P) in the Behavioral Despair Test in mice.

TABLE 7

Effect of Intraperitoneal Administration of (1R,4S)-N-[4-(3,4-dichlorophenyl-1,2,3,4-tetrahydro-1naphthalenamine (P) in the Behavioral Despair Test[1] in Mice (N = 10)

| Compound | Vehicle | Imipramine 10 mg/kg | P 0.03 mg/kg | P 0.1 mg/kg | P 0.3 mg/kg | P 1 mg/kg | P 3 mg/kg |
|---|---|---|---|---|---|---|---|
| Immobility | 130 | 63 | 128 | 119 | 114 | 29 | 12 |
| Duration | 82 | 28 | 120 | 96 | 109 | 66 | 49 |
| (sec) | 129 | 33 | 96 | 85 | 115 | 87 | 0 |
| | 172 | 89 | 129 | 100 | 93 | 34 | 3 |
| | 162 | 85 | 99 | 103 | 23 | 51 | 17 |
| | 148 | 73 | 107 | 76 | 102 | 35 | 5 |
| | 154 | 37 | 159 | 109 | 110 | 51 | 0 |
| | 118 | 74 | 102 | 56 | 106 | 19 | 40 |
| | 133 | 95 | 115 | 98 | 98 | 81 | 0 |
| | 153 | 5 | 122 | 62 | 120 | 50 | 26 |
| Mean ± sem | 138 | 58 | 118 | 90 | 99 | 50 | 15 |
| | 8 | 10 | 6 | 6 | 9 | 7 | 6 |
| Dunnett | P < 0.05 | * | ns | * | * | * | * |

[1]The Behavioral Despair Test is also known as the Porsolt swim test (Porsolt, et al., 1977. Nature 266: 730-732).
[2]Vehicle = saline
* indicates a significant difference vs vehicle for P < 0.05 (Dunnett test)

The contents of each of the references cited herein, including the contents of the references cited within the primary references, are herein incorporated by reference in their entirety.

The invention being thus described, it is apparent that the same can be varied in many ways. Such variations are not to be regarded as a departure from the spirit and scope of the present invention, and all such modifications and equivalents as would be obvious to one skilled in the art are intended to be included within the scope of the following claims.

We claim:
1. A process for preparation of a compound of formula P

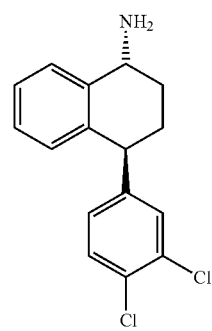

(P)

comprising:
a) reacting a compound of formula 1

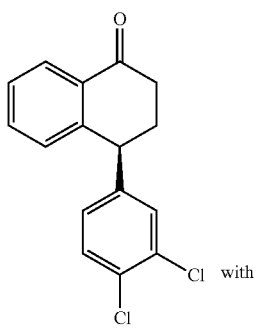

(1)

with

-continued

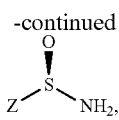

wherein Z is —CR⁴R⁵R⁶, wherein R⁴ is $C_1$-$C_6$ alkyl, R⁵ is $C_1$-$C_6$ alkyl, and R⁶ is $C_1$-$C_6$ alkyl, to obtain compound of formula 2a

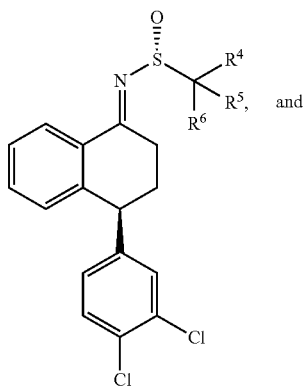

(2a)

and b) reducing the compound of formula 2a with a hydride reducing agent followed by solvolysis.

2. The process according to claim 1 wherein solvolysis is catalyzed by acid, whereby an acid addition salt of the compound of formula P is formed.

3. The process according to claim 2 further comprising crystallizing an acid addition salt of the compound of formula P.

4. The process according to either of claim 2 or 3 further comprising a step of converting said acid addition salt of the compound of formula P to a free base of compound P.

5. A process of claim 1, wherein reacting a compound of formula 1 with

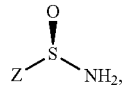

further comprises the presence of a dehydrating agent.

6. The process according to claim 5 wherein the dehydrating agent is selected from titanium alkoxide, boron trifluoride etherate, boron trifluoride etherate with magnesium sulfate, and molecular sieves.

7. The process according to claim 6 wherein the titanium alkoxide is selected from titanium ethoxide and titanium isopropoxide.

8. The process according to claim 1 wherein the reducing agent is selected from 9-borabicyclononane, sodium borohydride, catechol borane, borane, and diisobutylaluminum hydride with zinc halide.

9. The process according to claim 2 wherein the acid is hydrochloric acid.

10. The process according to claim 1 wherein each of R⁴, R⁵, and R⁶ is methyl.

11. The process according to claim 4 wherein the converting step comprises treating with a base.

12. The process according to claim 3 further comprising recrystallizing an acid addition salt of the compound of formula P from a solvent selected from an alcohol and a mixture of alcohol and hydrocarbon solvent.

13. The process according to claim 8 wherein the reducing step is carried out in a solvent comprising tetrahydrofuran.

* * * * *